US009539020B2

(12) United States Patent
Conlon et al.

(10) Patent No.: US 9,539,020 B2
(45) Date of Patent: Jan. 10, 2017

(54) COUPLING FEATURES FOR ULTRASONIC SURGICAL INSTRUMENT

(71) Applicant: Ethicon Endo-Surgery, Inc., Cincinnati, OH (US)

(72) Inventors: Sean P. Conlon, Loveland, OH (US); David J. Cagle, Cincinnati, OH (US); David A. Monroe, Cincinnati, OH (US); John A. Hibner, Mason, OH (US); Cole Constantineau, Cambridge, MA (US); Saeed Sokhanvar, Belmont, MA (US); Michel Bruehwiler, Newton, MA (US); Daniel Yasevac, Somerville, MA (US); Mohammadreza Ramezanifard, Watertown, MA (US); Judy Walish, Brighton, MA (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 195 days.

(21) Appl. No.: 14/142,216

(22) Filed: Dec. 27, 2013

(65) Prior Publication Data

US 2015/0182250 A1    Jul. 2, 2015

(51) Int. Cl.
*A61B 17/32*    (2006.01)
*A61B 17/00*    (2006.01)

(52) U.S. Cl.
CPC .......... *A61B 17/320092* (2013.01); *A61B 17/320068* (2013.01); *A61B 2017/0046* (2013.01);
(Continued)

(58) Field of Classification Search
CPC ............ A61B 17/320092; A61B 17/320068; A61B 2090/031; A61B 2017/00477; A61B 2017/00473
See application file for complete search history.

(56) References Cited

U.S. PATENT DOCUMENTS 5,322,055 A    6/1994 Davison et al.
5,582,617 A *  12/1996 Klieman ............... A61B 17/29
                                                                606/170
(Continued)

FOREIGN PATENT DOCUMENTS

EP    2055243 A2    5/2009
EP    2581055 A2    4/2013

OTHER PUBLICATIONS

U.S. Appl. No. 13/657,553, filed Oct. 22, 2012.
(Continued)

*Primary Examiner* — Richard Louis
(74) *Attorney, Agent, or Firm* — Frost Brown Todd LLC

(57) ABSTRACT

A surgical apparatus comprises a body, an ultrasonic transducer, a shaft, and an end effector. The ultrasonic transducer is operable to convert electrical power into ultrasonic vibrations. The body comprises a pivotal trigger. The shaft couples the end effector and the body together. The end effector comprises a clamp arm and an ultrasonic blade in acoustic communication with the ultrasonic transducer. The ultrasonic blade is operable to deliver ultrasonic vibrations to tissue. Pivotal movement of the trigger causes movement of the clamp arm. The shaft is operable to be selectively coupled and decoupled from the ultrasonic transducer. The apparatus comprises electro-mechanical means for coupling and decoupling the shaft from the ultrasonic transducer, and may further comprise means for preventing movement of the shaft as it is coupled to the ultrasonic transducer.

20 Claims, 67 Drawing Sheets

(52) U.S. Cl.
CPC ............... *A61B 2017/00473* (2013.01); *A61B 2017/00477* (2013.01); *A61B 2090/031* (2016.02)

(56) References Cited

U.S. PATENT DOCUMENTS

| | | | |
|---|---|---|---|
| 5,776,155 | A | 7/1998 | Beaupre et al. |
| 5,873,873 | A | 2/1999 | Smith et al. |
| 5,980,510 | A | 11/1999 | Tsonton et al. |
| 6,325,811 | B1 | 12/2001 | Messerly |
| 6,695,782 | B2 | 2/2004 | Ranucci et al. |
| 6,773,444 | B2 | 8/2004 | Messerly |
| 6,783,524 | B2 | 8/2004 | Anderson et al. |
| 8,461,744 | B2 | 6/2013 | Wiener et al. |
| 8,486,096 | B2 | 7/2013 | Robertson et al. |
| 8,591,536 | B2 | 11/2013 | Robertson |
| 8,623,027 | B2 | 1/2014 | Price et al. |
| 8,800,838 | B2 | 8/2014 | Shelton |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0069940 | A1 | 3/2010 | Miller et al. |
| 2011/0087212 | A1 | 4/2011 | Aldridge et al. |
| 2011/0087218 | A1* | 4/2011 | Boudreaux ........ A61B 18/1445 606/41 |
| 2011/0196375 | A1* | 8/2011 | Li .................... H02K 7/116 606/80 |
| 2012/0112687 | A1 | 5/2012 | Houser et al. |
| 2012/0116265 | A1 | 5/2012 | Houser et al. |
| 2013/0095077 | A1* | 4/2013 | Wang .................. C12N 5/0607 424/93.7 |
| 2013/0324998 | A1* | 12/2013 | Kimball ......... A61B 17/320068 606/41 |
| 2014/0005701 | A1 | 1/2014 | Olson et al. |

OTHER PUBLICATIONS

U.S. Appl. No. 61/410,603, filed Nov. 5, 2010.
International Search Report and Written Opinion re Application No. PCT/US2014/072040 dated Jun. 10, 2015.

\* cited by examiner

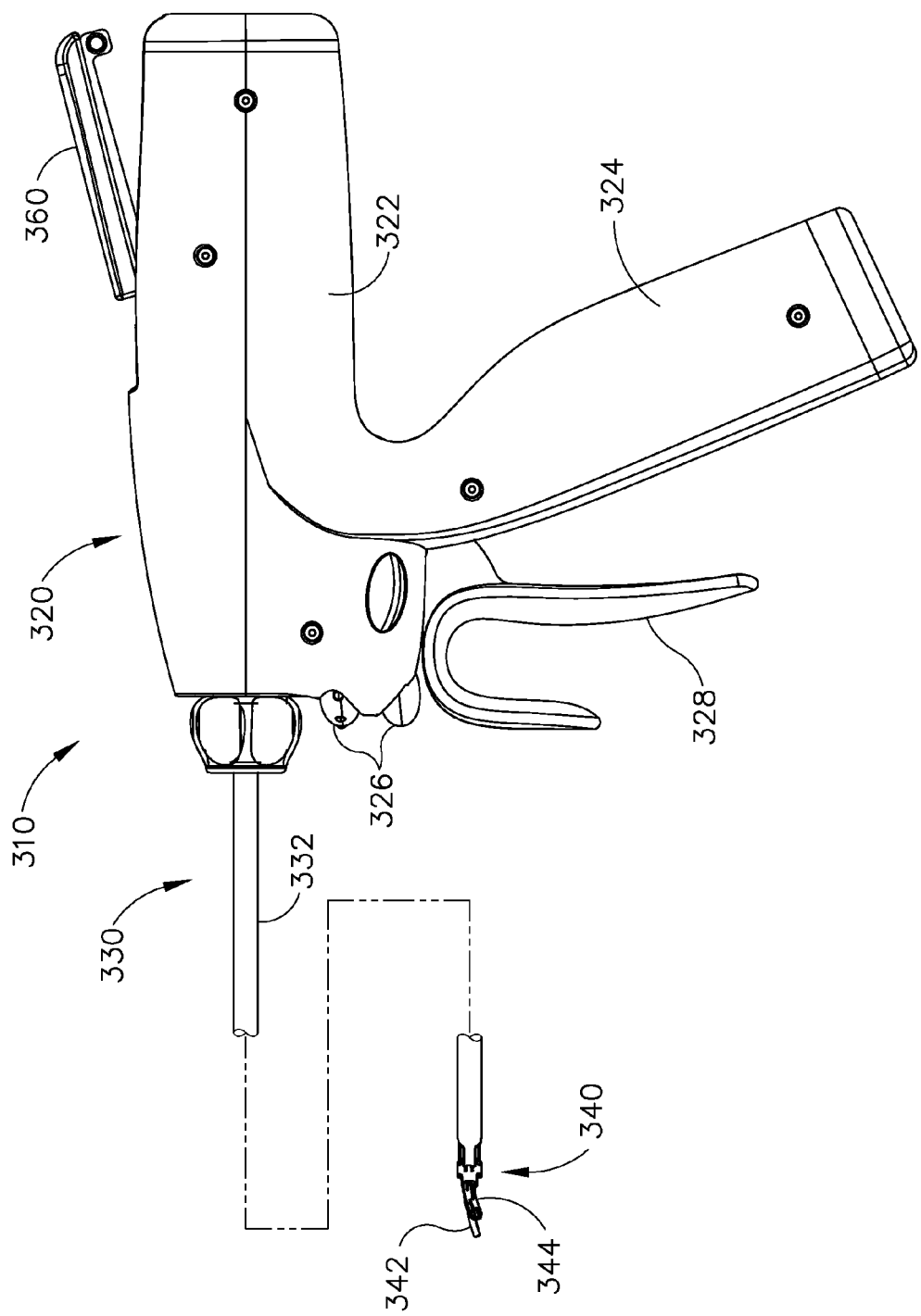

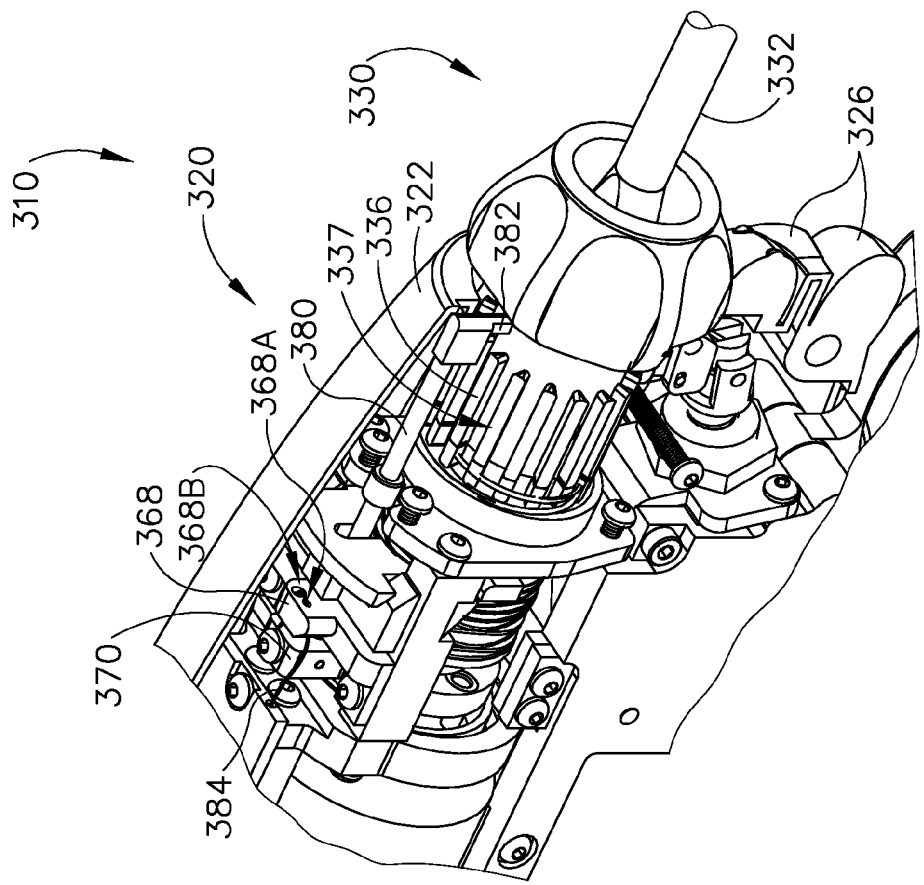
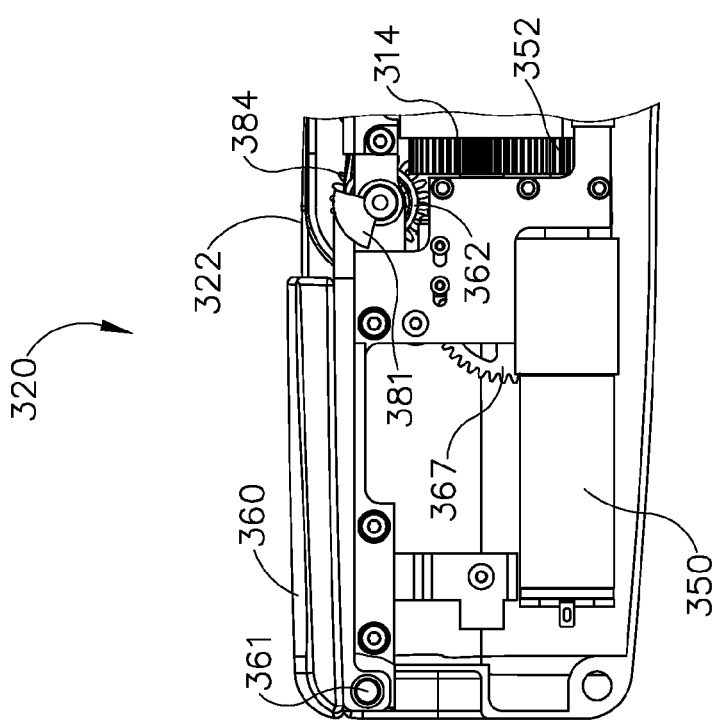
Fig.24D
Fig.24C

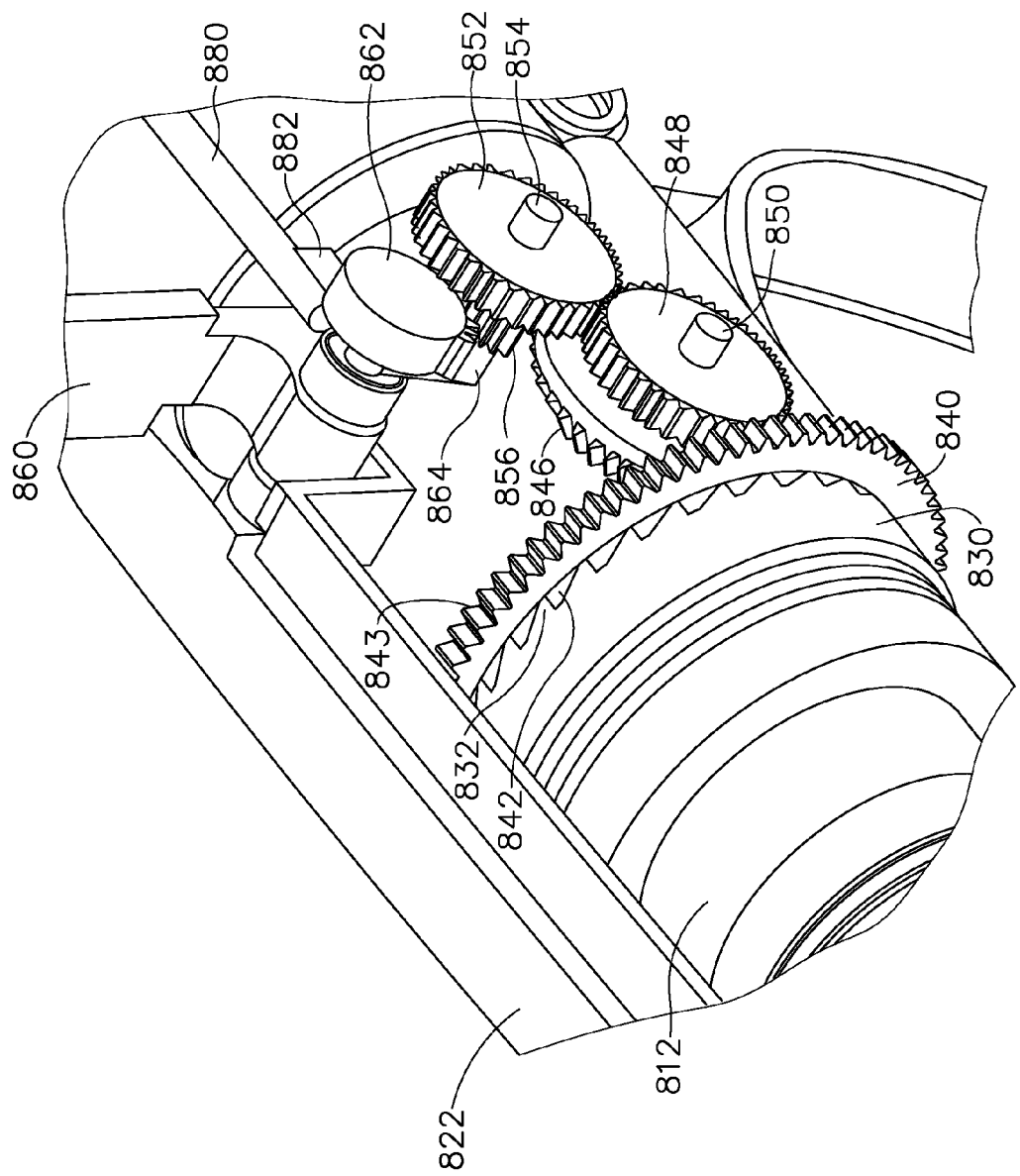

COUPLING FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15 depicts a side elevational view of another exemplary alternative surgical instrument;

FIG. 24C depicts a side elevational view of the lever arm of the handle assembly of FIG. 16 in the fourth rotational position;

FIG. 24D depicts a perspective view of a locking mechanism of the handle assembly of FIG. 16 moved into a second longitudinal position correlating to the lever arm of the handle assembly in the fourth rotational position;

FIG. 54 depicts a perspective view of an exemplary alternative assembly for coupling an acoustic waveguide with an ultrasonic transducer, suitable for incorporation into the instrument of FIG. 1;

Figure 1:
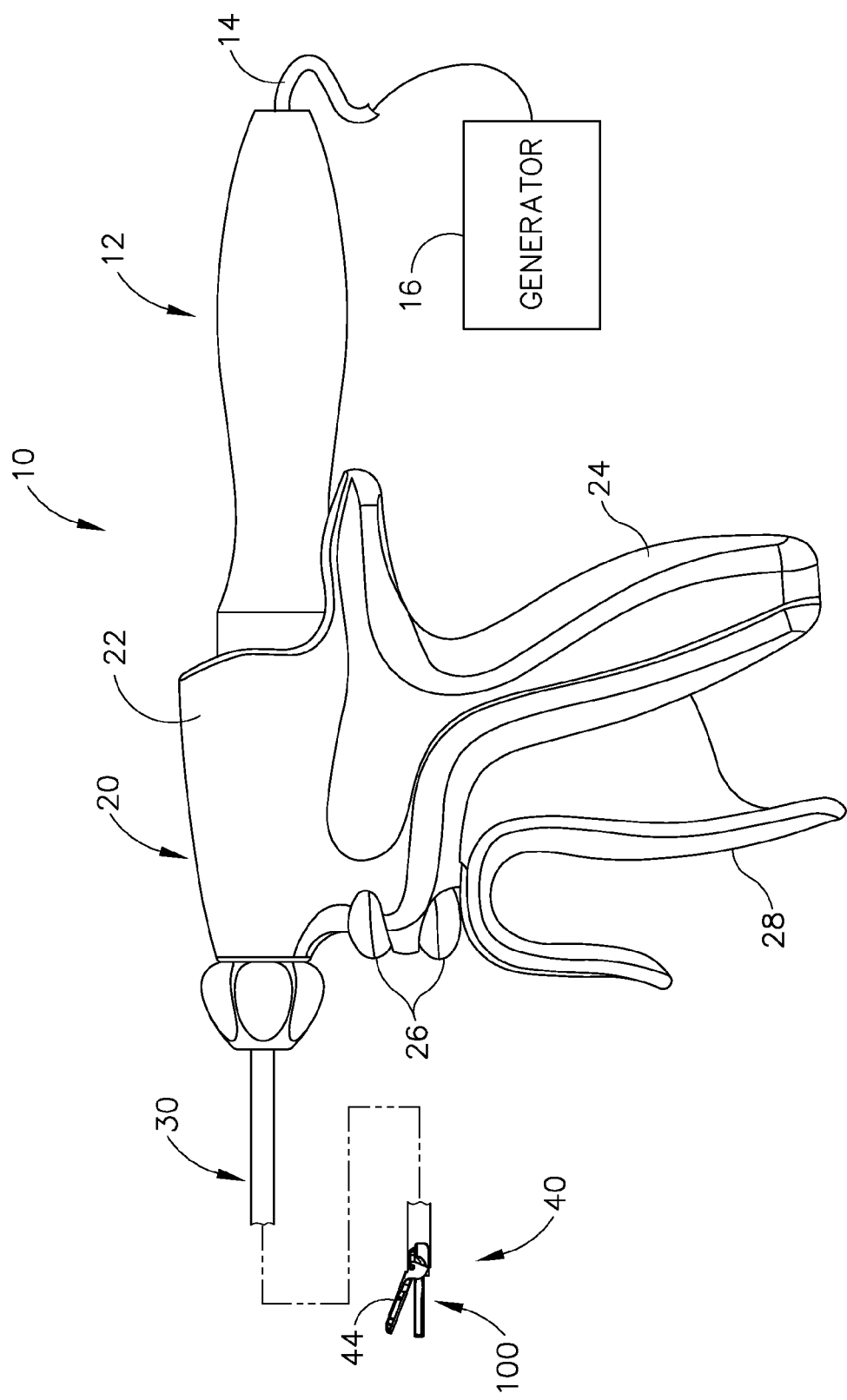
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027, issued Jan. 7, 2014; U.S. Pub. No. 2010/0069940, now U.S. Pat. No. 9,023,071, issued May 5, 2015; U.S. Pub. No. 2011/0015660, now U.S. Pat. No. 8,461,744, issued Jun. 11, 2013; U.S. Pub. No. 2012/0112687, now U.S. Pat. No. 9,381,058, issued Jul. 5, 2016; U.S. Pub. No. 2012/0116265; U.S. patent application Ser. No. 13/538,588, now U.S. Pat. No. 9,393,037, issued Jul. 19, 2016; U.S. patent application Ser. No. 13/657,553, now U.S. Pat. No. 9,095,367, issued Aug. 4, 2015; U.S. Pat. App. No. 61/410,603; and/or U.S. patent application Ser. No. 14/028,717, now U.S. Pub. No. 2015/0080924, published Mar. 19, 2015. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
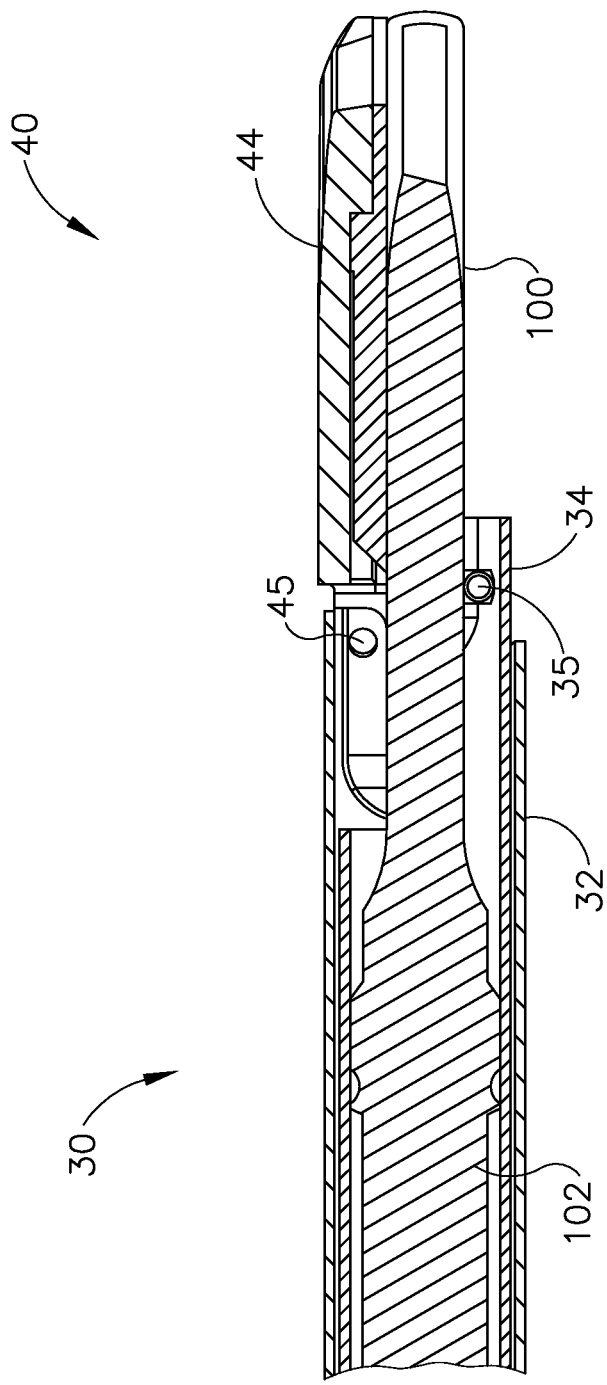
FIG. 2 depicts a side cross-sectional view of an end effector of the instrument of FIG. 1, with a clamp arm in a closed position.
Figure 3:
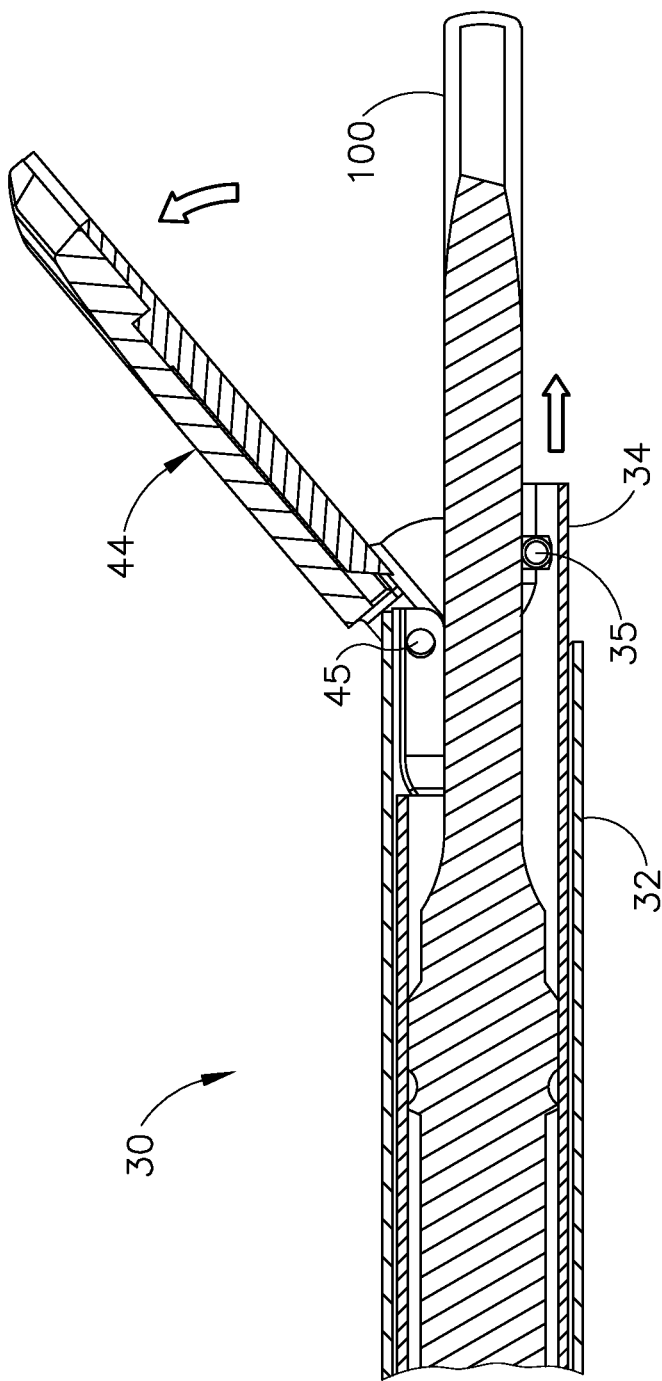
FIG. 3 depicts a side cross-sectional view of the end effector of FIG. 2, with the clamp arm moved to an open position.
Figure 4:
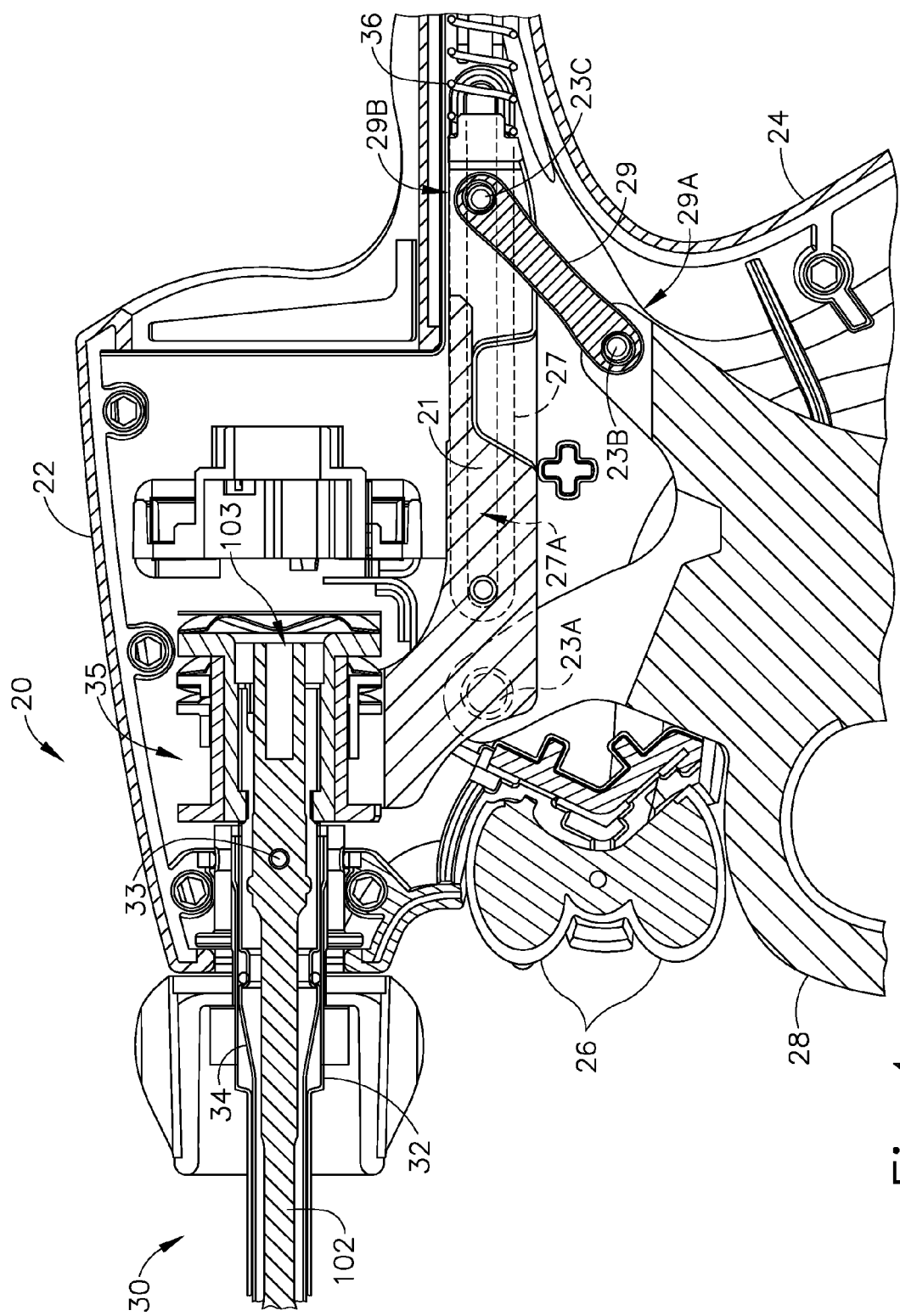
FIG. 4 depicts a cross-sectional view of a handle assembly of the instrument of FIG. 1.
Figure 5:
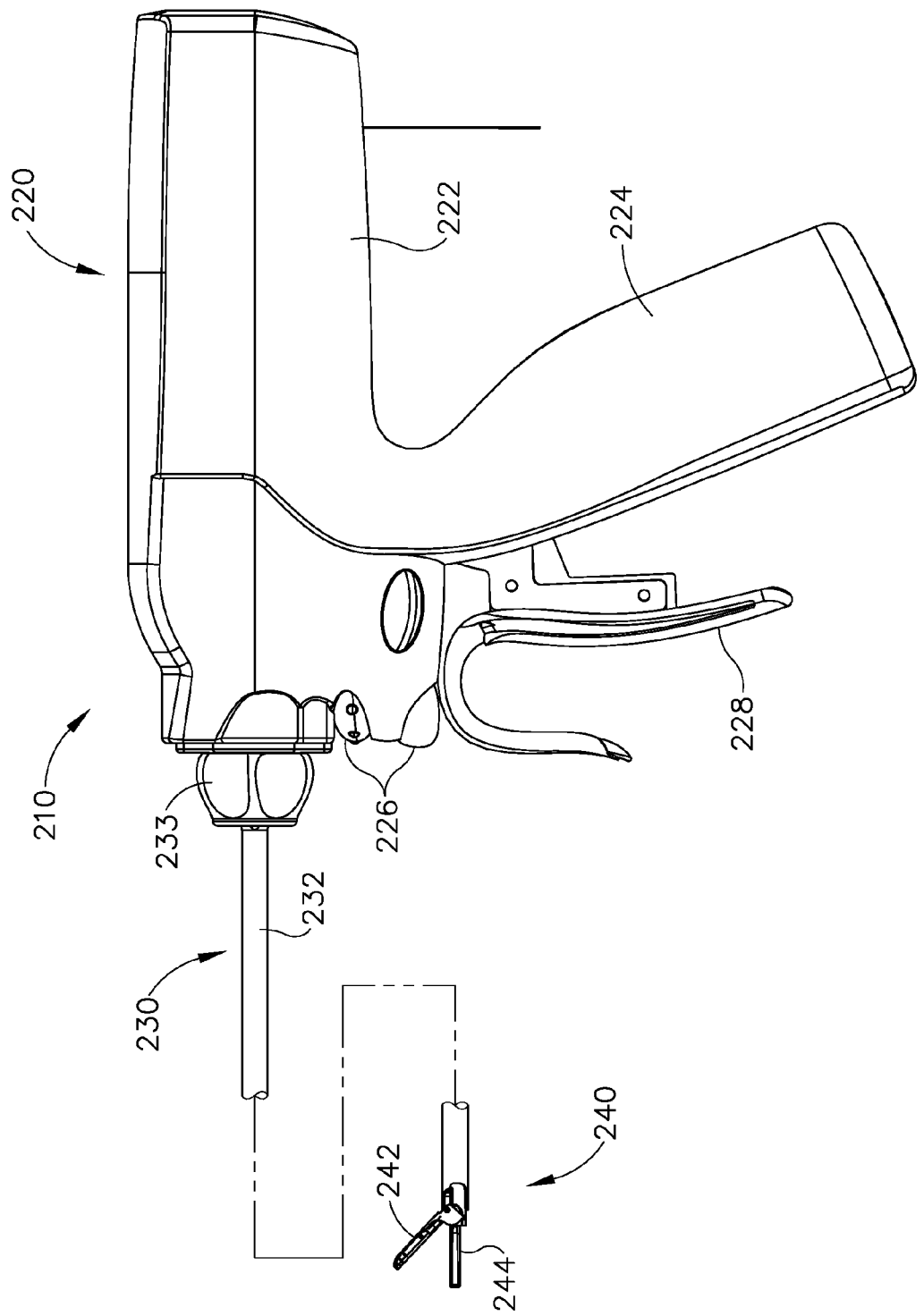
FIG. 5 depicts a side elevational view of an exemplary alternative surgical instrument.

Instrument (10) of the present example comprises a handle assembly (20), a shaft assembly (30), and an end effector (40). As shown in FIGS. 2-4, shaft assembly (30) comprises an outer sheath (32), an inner tube (34) slidably disposed within outer sheath (32), and a waveguide (102) disposed within inner tube (34). As will be discussed in more detail below, longitudinal translation of inner tube (34) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. As shown in FIG. 4, trigger (28) is pivotably coupled to handle assembly (20) via a pin (23A) such that trigger (28) rotates about an axis located below shaft assembly (30).

Trigger (28) is coupled with a yoke (25) via a linkage (29) such that rotation of trigger (28) about pin (23A) causes longitudinal translation of yoke (25). A first end (29A) of linkage (29) is rotatably coupled with a proximal portion of trigger (28) via a pin (23B). A second end (29B) of linkage (29) is rotatably coupled with a proximal portion of yoke (25) via a pin (23C). A pair of elongate oval-shaped projections (27) extend inwardly from interior surfaces of body (22). An interior surface of each oval-shaped projection (27) defines an elongate oval-shaped slot (27A). Pin (23C) passes completely through the proximal portion of yoke (25) and second end (29B) of linkage (29) such that ends of pin (23C) extend from opposite sides of yoke (25). These ends of pin (23C) are slidably and rotatably disposed within oval-shaped slots (27A). A pin (23D) passes completely through a distal portion of yoke (25) such that ends of pin (23D) extend from opposite sides of yoke (25). These ends of pin (23D) are slidably and rotatably disposed within oval-shaped slots (27A). It should therefore be understood that yoke (25) is longitudinally translatable via pins (23C, 23D) within oval-shaped slots (27A) between a proximal longitudinal position and a distal longitudinal position. Furthermore, because the proximal portion of trigger (28) is coupled with yoke (25) via linkage (29), it should be understood that pivoting of trigger (28) toward pistol grip (24) will cause proximal longitudinal translation of yoke (25) within oval-shaped slots (27A); and that pivoting of trigger (28) away from pistol grip (24) will cause distal longitudinal translation of yoke (25) within oval-shaped slots (27A).

A distal portion of yoke (25) is coupled with inner tube (34) of shaft assembly (30) via a coupling assembly (35). As discussed above, inner tube (34) is longitudinally translatable within outer sheath (32), such that inner tube (34) is configured to longitudinally translate concurrently with yoke (25). Furthermore, because pivoting of trigger (28) toward pistol grip (24) causes proximal longitudinal translation of yoke (25), it should be understood that pivoting of trigger (28) toward pistol grip (24) will cause proximal longitudinal translation of inner tube (34) relative to outer sheath (32) and handle assembly (20). Finally, because pivoting of trigger (28) away from pistol grip (24) causes distal longitudinal translation of yoke (25), it should be understood that and that pivoting of trigger (28) away from pistol grip (24) will cause distal longitudinal translation of inner tube (34) relative to outer sheath (32) and handle assembly (20). As shown in FIG. 4, a spring (36) is positioned within a proximal end of body (22) of handle assembly (20). Spring (36) bears against a portion of body (22) and a proximal end of yoke (25) to thereby bias yoke (25) toward the distal position. Biasing of yoke (25) toward the distal position causes inner tube (34) to be biased distally and further causes trigger (28) to be biased away from pistol grip (24).

As shown in FIGS. 2 and 3, end effector (40) includes an ultrasonic blade (100) and a pivoting clamp arm (44). Clamp arm (44) is pivotably coupled with a distal end of outer sheath (32) of shaft assembly (30) above ultrasonic blade (100) via a pin (45). As best seen in FIG. 3, a distal end of inner tube (34) is rotatably coupled with a proximal end of clamp arm (44) below ultrasonic blade (100) via a pin (35) such that longitudinal translation of inner tube (34) causes rotation of clamp arm (44) about pin (45) toward and away from ultrasonic blade (100) to thereby clamp tissue between clamp arm (44) and ultrasonic blade (100) to cut and/or seal the tissue. In particular, proximal longitudinal translation of inner tube (34) relative to outer sheath (32) and handle assembly (20) causes clamp arm (44) to move toward ultrasonic blade (100); and distal longitudinal translation of inner tube (34) relative to outer sheath (32) and handle assembly (20) causes clamp arm (44) to move away from ultrasonic blade (100). It should therefore be understood that pivoting of trigger (28) toward pistol grip (24) will cause clamp arm (44) to move toward ultrasonic blade (100); and that pivoting of trigger (28) away from pistol grip (24) will cause clamp arm (44) to move away from ultrasonic blade (100). In some versions, one or more resilient members are used to bias clamp arm (44) and/or trigger (28) to the open position shown in FIG. 4.

An ultrasonic transducer assembly (12) extends proximally from body (22) of handle assembly (20). While transducer assembly (12) is shown in FIG. 1, transducer assembly (12) is omitted from FIG. 4. Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (102), which extends through shaft assembly (30) to reach ultrasonic blade (100). As shown in FIG. 4, the proximal end of waveguide (102) includes a threaded recess (103), which is removably coupled with a threaded stud (not shown) that extends distally from transducer assembly (12). This provides a secure mechanical and acoustic coupling between transducer assembly (12) and waveguide (102). Waveguide (102) is secured within shaft assembly (30) via a pin (33), which passes through waveguide (102) and shaft assembly (30). Pin (33) is located at a position along the length of waveguide (102) corresponding to a node associated with resonant ultrasonic vibrations communicated through waveguide (102). As noted above, when ultrasonic blade (100) is in an activated state (i.e., vibrating ultrasonically), ultrasonic blade (100) is operable to effectively cut through and seal tissue, particularly when the tissue is being clamped between clamp arm (44) and ultrasonic blade (100). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of ultrasonic blade (100) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (12) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide (102) to reach ultrasonic blade (100), thereby providing oscillation of ultrasonic blade (100) at the resonant ultrasonic frequency. Thus, when tissue is secured between ultrasonic blade (100) and clamp arm (44), the ultrasonic oscillation of ultrasonic blade (100) may simultaneously sever the tissue and denature the proteins in adjacent tissue cells, thereby providing a coagulative effect with relatively little thermal spread. In some versions, an electrical current may also be provided through ultrasonic blade (100) and clamp arm (44) to also seal the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively activate transducer assembly (12) to activate ultrasonic blade (100). In the present example, two buttons (26) are provided—one for activating ultrasonic blade (100) at a low power and another for activating ultrasonic blade (100) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued May 5, 2015; U.S. Pub. No. 2011/0015660, now U.S. Pat. No. 8,461,744, issued Jun. 11, 2013; U.S. Pub. No. 2012/0112687, now U.S. Pat. No. 9,381,058, issued Jul. 5, 2016; U.S. Pub. No. 2012/0116265; U.S. patent application Ser. No. 13/538,588, now U.S. Pat. No. 9,393,037, issued Jul. 19, 2016; and/or U.S. patent application Ser. No. 13/657,553, now U.S. Pat. No. 9,095,367, issued Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

II. Exemplary Alternative Ultrasonic Surgical Instruments with Electromechanical Features for Coupling Transducer with Waveguide As noted above, waveguide (102) is mechanically and acoustically coupled with transducer assembly (12) by a threaded stud of transducer assembly (12), which is threaded into a threaded recess (103) formed in the proximal end of waveguide (102). Instrument (10) may be provided to the operator in a state where shaft assembly (30) is decoupled from handle assembly (20) and transducer assembly (12). In some such versions, the operator grasps shaft assembly (30) with one hand and transducer assembly (12) with the other hand; then rotates shaft assembly (30) relative to transducer assembly (12) in order to threadably couple the threaded stud of transducer assembly (12) in threaded recess (103) of waveguide (102). In some such versions, a torque wrench may be used to adjust this coupling with an appropriate amount of torque.

It may be desirable in some instances to replace the above described manual coupling procedure with a coupling procedure that is motorized or otherwise automated. In particular, it may be desirable to include integrated coupling features that provide electro-mechanical coupling and/or decoupling of shaft assembly (30) with handle assembly (20) and transducer assembly (12). Several merely illustrative examples of such features are described in greater detail below, while other examples of such features will be apparent to those of ordinary skill in the art in view of the teachings herein.

A. Exemplary Ultrasonic Surgical Instrument with Coupling Via Motor and Lug Drive FIGS. 5-14D show an exemplary instrument (210) having a shaft assembly (230) that is configured to selectively couple with a handle assembly (220) and transducer assembly (12) through activation of a motor (250). Instrument (210) of the present example is configured to operate substantially similar to instrument (10) discussed above except for the differences discussed below. In particular, instrument (210) is configured to clamp tissue between a pivoting clamp arm (244) and an ultrasonic blade (242) of an end effector (240); and cut/seal the tissue by ultrasonically activating blade (242).

Instrument (210) of the present example comprises a handle assembly (220), a shaft assembly (230), and an end effector (240). Shaft assembly (230) comprises an outer sheath (232), an inner tube (not shown) slidably disposed within outer sheath (232), and a waveguide (not shown) disposed within the inner tube. As with inner tube (34) of instrument (10) discussed above, longitudinal translation of the inner tube of the present example causes actuation of clamp arm (244) of end effector (240). Handle assembly (220) comprises a body (222) including a pistol grip (224) and a pair of buttons (226). Handle assembly (220) also includes a trigger (228) that is pivotable toward and away from pistol grip (224). Trigger (228) is pivotably coupled to handle assembly (220). Pivotal movement of trigger (228) causes longitudinal translation of the inner tube to thereby cause pivotal movement of clamp arm (244) toward and away from ultrasonic blade (242).

Figure 6:
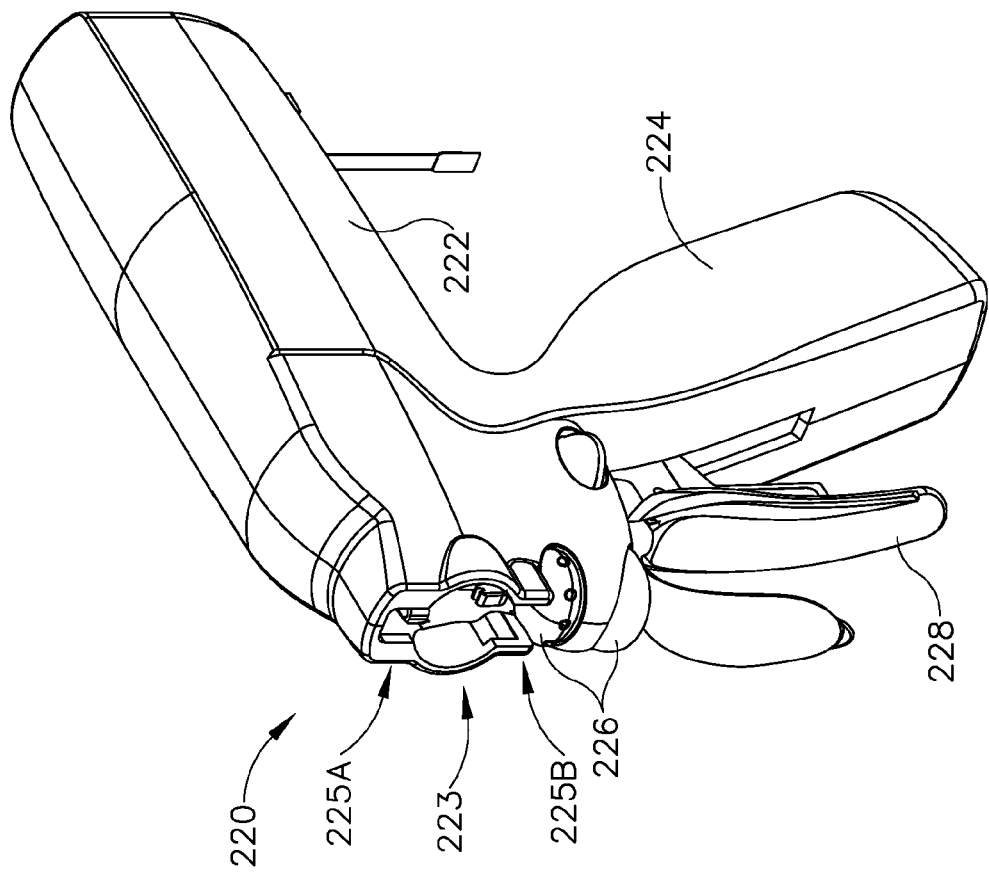
FIG. 6 depicts a perspective view of a handle assembly of the instrument of FIG. 5.
Figure 7:
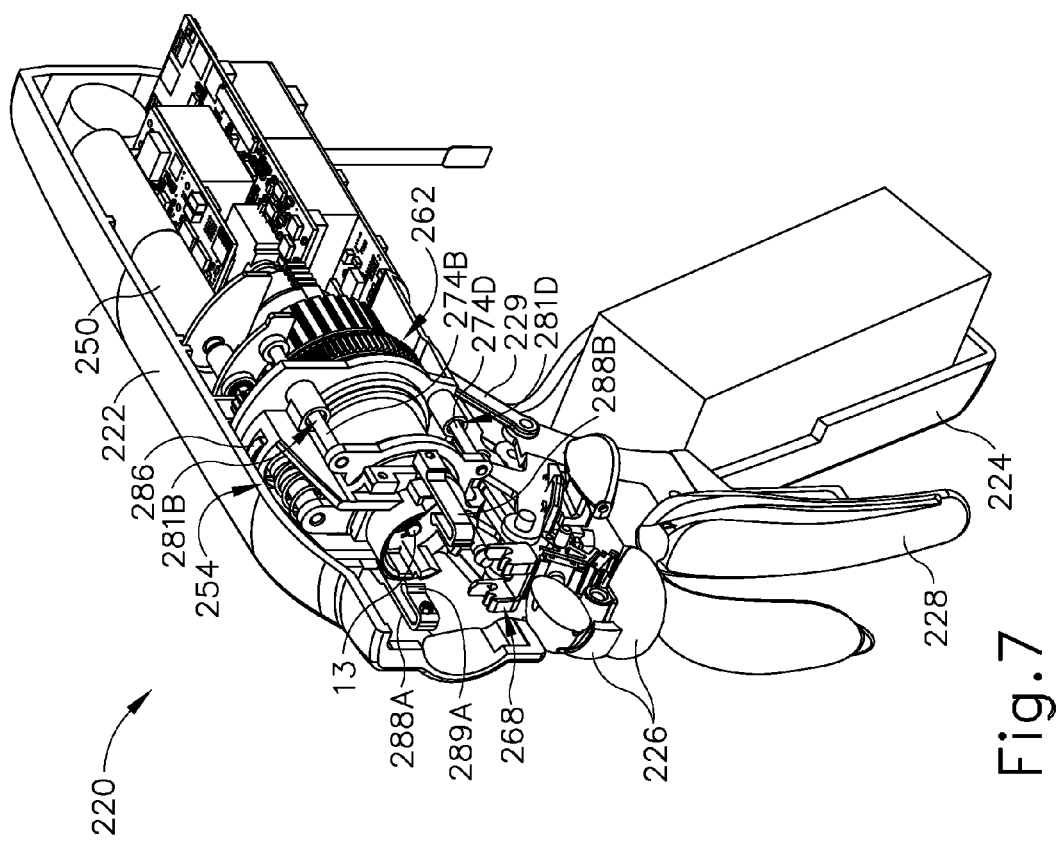
FIG. 7 depicts a perspective view the handle assembly of FIG. 6, with a portion of the handle assembly removed to reveal internal components of the handle assembly.

As will be discussed in more detail below, handle assembly (220) is configured to receive and selectively secure shaft assembly (230) therein. As shown in FIG. 6, a distal portion of body (222) of handle assembly (220) defines a keyed bore (223) defining a pair of longitudinal slots (225A, 225B). Keyed bore (223) of body (222) provides access to the interior of handle assembly (220) and is configured to receive a proximal engagement housing (231) of shaft assembly (230). As best seen in FIGS. 8-11, proximal engagement housing (231) of shaft assembly (230) defines a pair of longitudinal projections (236A, 236B). Longitudinal slots (225A, 225B) are configured to receive longitudinal projections (236A, 236B) of proximal engagement housing (231) as shaft assembly (230) is inserted into keyed bore (223) of body (222) to thereby prevent rotation of shaft assembly (230) as shaft assemble (230) is secured to handle assembly (220); and to ensure proper alignment of features at proximal engagement housing (231) of shaft assembly (230) with corresponding components at the distal portion of handle assembly (220).

Figure 11:
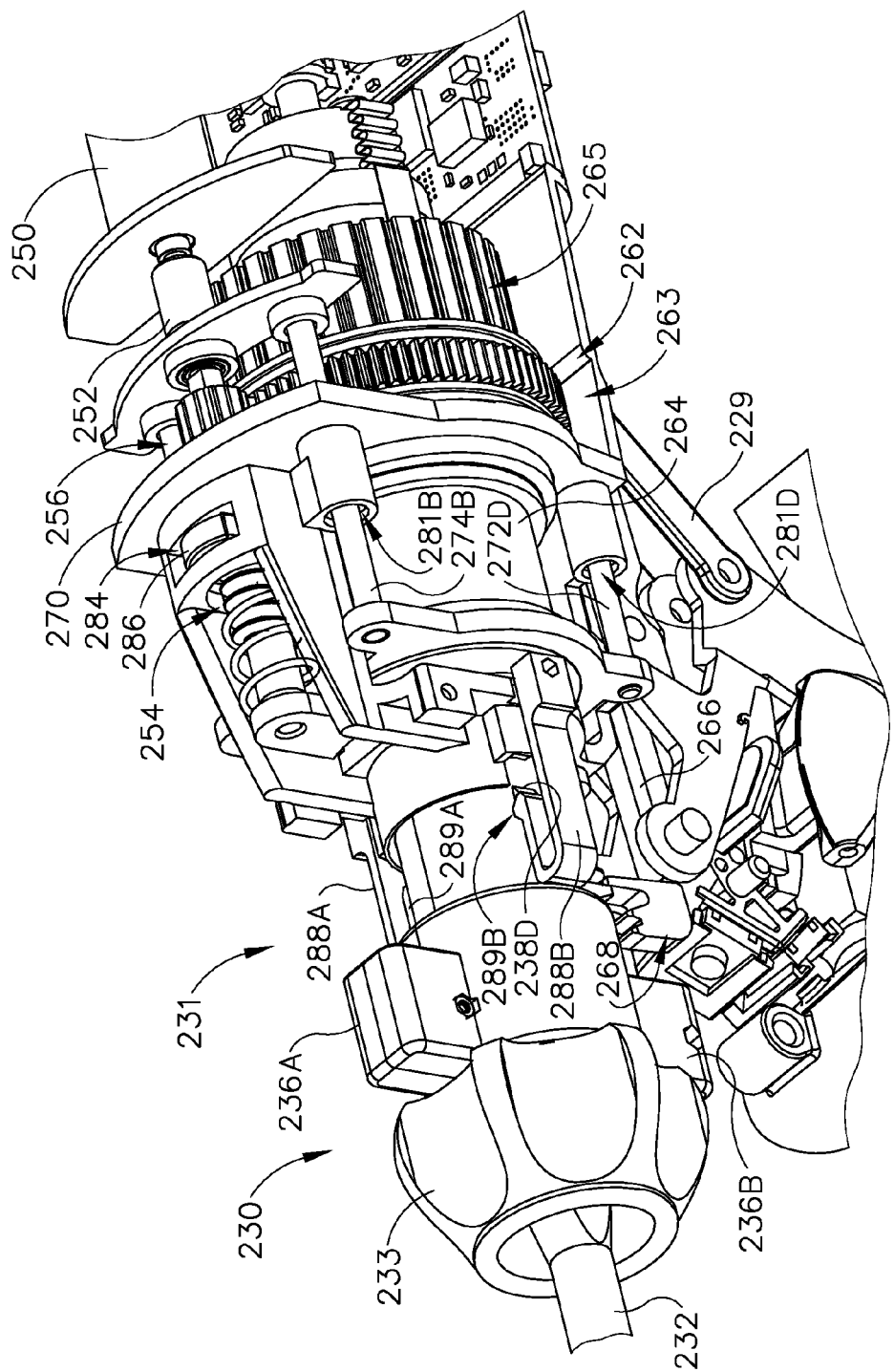
FIG. 11 depicts a detailed perspective view of the internal components of the handle assembly of FIG. 6 engaged with the shaft assembly of FIG. 8.
Figure 12:
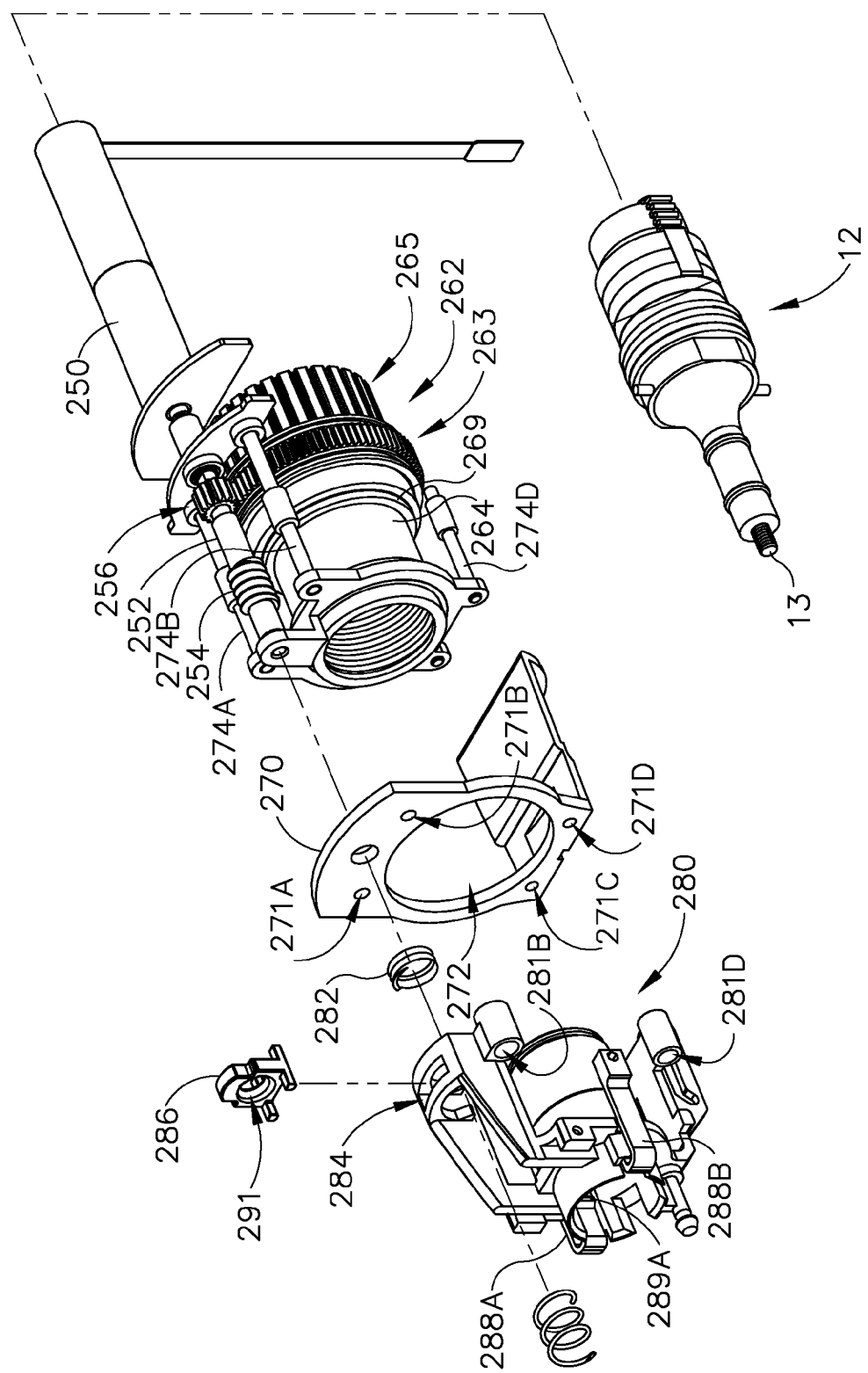
FIG. 12 depicts an exploded perspective view of the internal components of the handle assembly of FIG. 6.

As will be discussed in more detail below, handle assembly (220) comprises a plurality of internal components configured to selectively secure shaft assembly (230) within handle assembly (220). As best seen in FIGS. 11-12, handle assembly (220) comprises a support member (270) that is configured to provide structural support for the internal components of handle assembly (220). Support member (270) defines an opening (272). A rotatable housing (264) is rotatably disposed within opening (272) of support member (270) and is secured therein such that housing (264) is operable to rotate relative to support member (270). A pair of bushings (269) provide further structural support to housing (264) in body (222), while allowing housing (264) to rotate freely within body (222).

Transducer assembly (12) is disposed within housing (264) and is secured therein such that rotation of housing (264) relative to body (222) causes concurrent rotation of transducer assembly (12) relative to body (222). The proximal portion of housing (264) defines an angularly spaced array of longitudinally extending spline recesses (265). A ring gear (262) is coaxially disposed about the proximal portion of housing (264). Ring gear (262) includes an angular array of inner splines (not shown) that are disposed in spline recesses (265) of housing (264). It should therefore be understood that ring gear (262) and housing (264) rotate concomitantly; yet housing (264) may translate longitudinally relative to ring gear (262). The exterior of ring gear (262) includes a plurality of outwardly projecting teeth (263).

Handle assembly (220) further comprises a motor (250), which is fixedly secured within the interior of body (222). Motor (250) is operable to rotate a drive axle (252), which rotatably supported by support member (270). Axle (252) comprises a threaded region (254) and plurality of teeth (256) extending from an exterior of axle (252). Teeth (256) of axle (252) engage teeth (263) of ring gear (262) such that rotation of axle (252) causes rotation ring gear (262). As noted above, rotation of ring gear (262) provides rotation of housing (264) due to splined engagement with spline recesses (265) of housing (264). It should therefore be understood that motor (250) is operable to rotate transducer assembly (12) via axle (252), ring gear (262), and housing (264). As described in greater detail below, this motor activated rotation of transducer assembly (12) will thread the threaded stud (13) (see FIGS. 7 and 12) of transducer assembly (12) into a threaded bore defined in the proximal end of the waveguide (e.g., similar to threaded bore (103) of waveguide (102)), such that transducer assembly (12) may be mechanically and acoustically coupled with the waveguide.

Support member (270) defines a plurality of openings (271A, 271B, 271C, 271D). A plurality of guide posts (274A, 274B, 274C, 274D) are disposed within openings (271A, 271B, 271C, 271D) and secured therein. Handle assembly (220) further comprises a longitudinally translatable housing (280). Housing (280) defines a plurality of through bores (281A, 281B, 281C, 281D). Guide posts (274A, 274B, 274C, 274D) are slidably disposed in bores (281A, 281B, 281C, 281D) such that housing (280) is operable to translate between a proximal position and a distal position along guide posts (274A, 274B, 274C, 274D). As best seen in FIG. 12, housing (280) is positioned along guide posts (274A, 274B, 274C, 274D) distal to support member (270). A spring (282) is positioned between a distal face of support member (270) and a proximal face of housing (280) such that housing (280) is resiliently biased distally away from support member (270). Housing (280) defines a vertical slot (284). A threaded member (286) is positioned within vertical slot (284). An interior bore (291) of threaded member (286) defines an internal threading that is configured to threadably engage threaded region (254) of axle (252). Thus, rotation of axle (252) causes longitudinal translation of threaded member (286) and housing (280) along axle (252). As will be discussed in more detail below, as axle (252) rotates, axle (252) rotates transducer assembly (12) while simultaneously driving housing (280) proximally.

Figure 8:
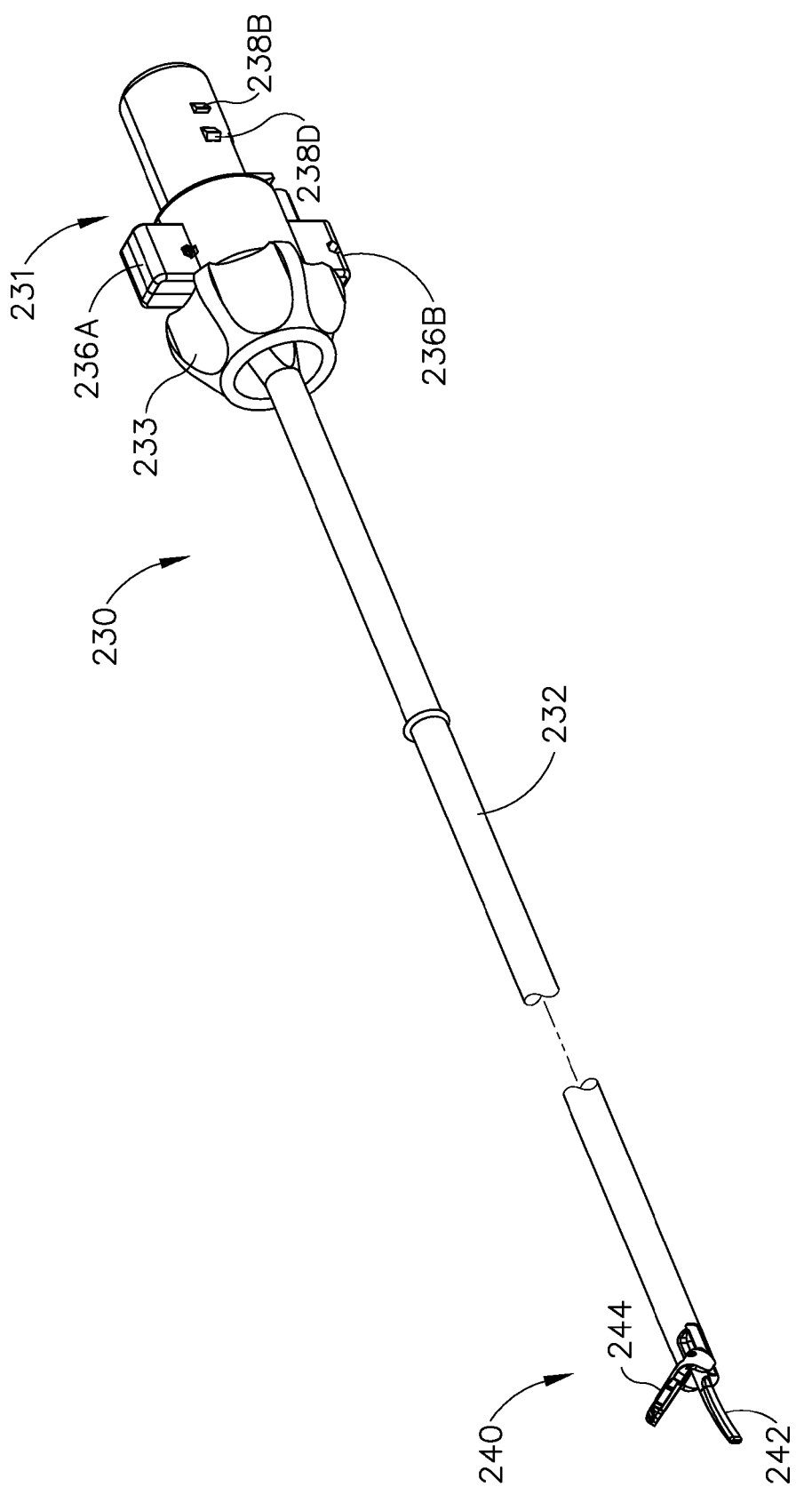
FIG. 8 depicts a perspective view of a shaft assembly of the instrument of FIG. 5.
Figure 9:
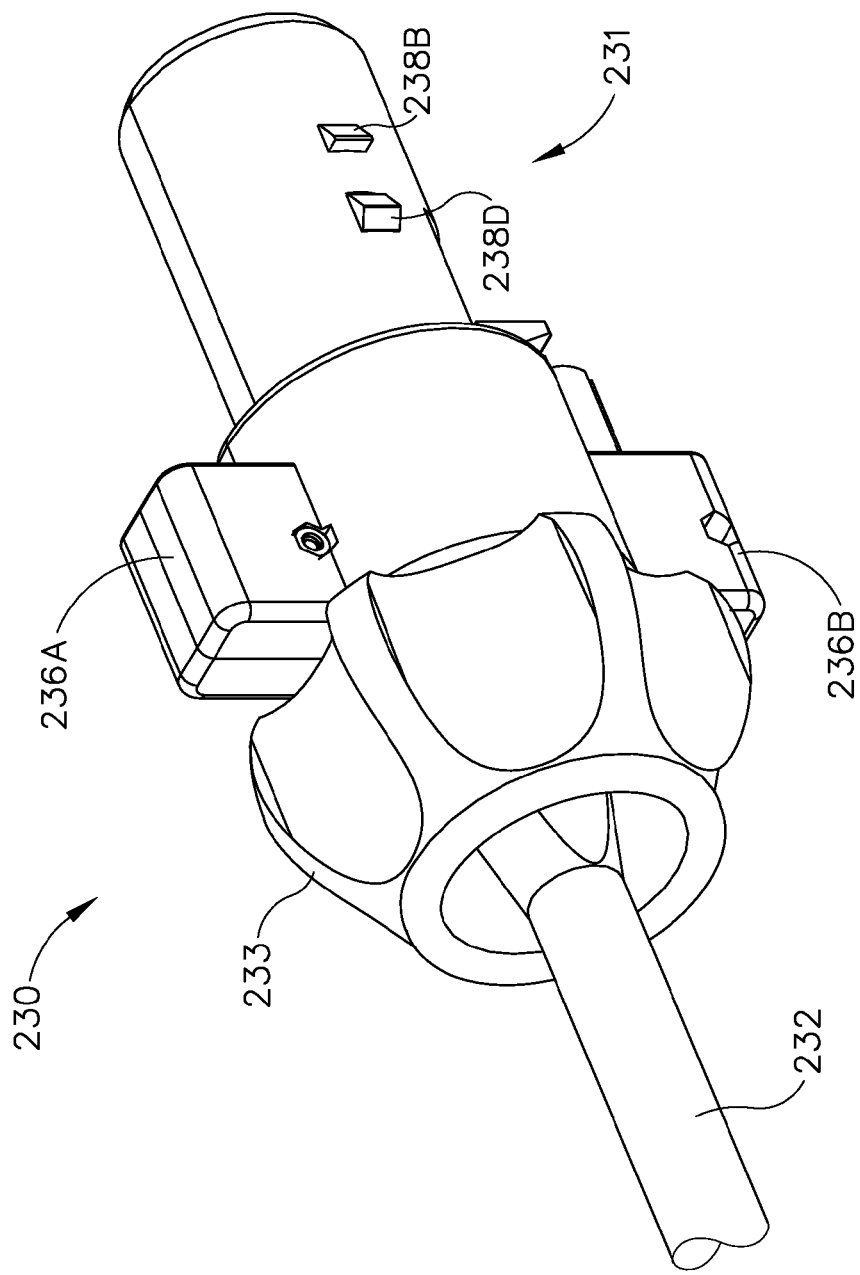
FIG. 9 depicts a detailed perspective view of a proximal end of the shaft assembly of FIG. 8.
Figure 10:
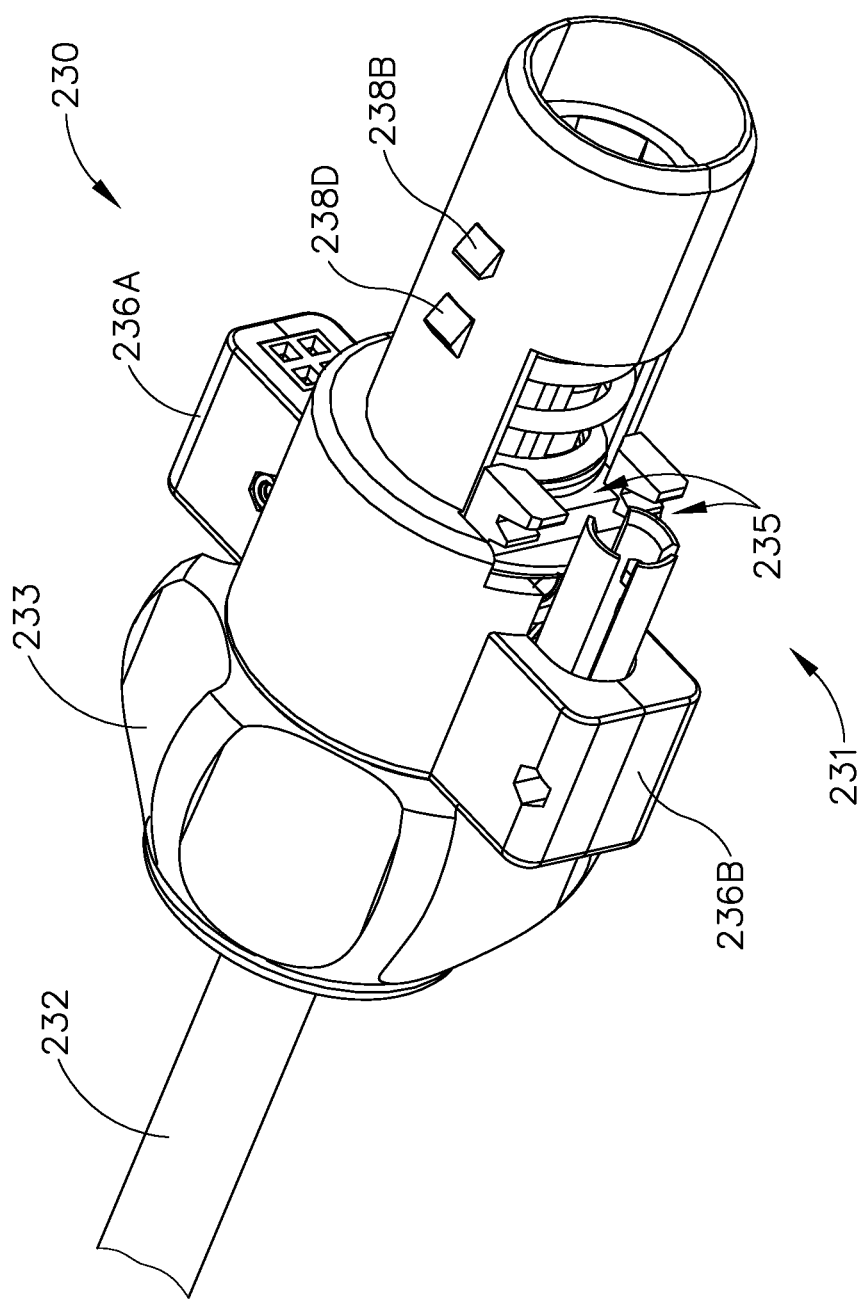
FIG. 10 depicts another detailed perspective view of the proximal end of the shaft assembly of FIG. 8.

As best seen in FIGS. 11-12, housing (280) further comprises a pair of distally extending resilient members (288A, 288B), each comprising a respective inwardly extending tab (289A, 289B). As best seen in FIGS. 8-10, proximal engagement housing (231) of shaft assembly (230) defines a plurality of outwardly extending tabs (238A, 238B, 238C, 238D). Tabs (238A, 238B, 238C, 238D) are configured to engage inwardly extending tabs (289A, 289B) as shaft assembly (230) is inserted into handle assembly (220) via keyed bore (223) of body (222). This, as housing (280) is driven proximally via rotation of axle (252), shaft assembly (230) is driven proximally as well due to engagement between inwardly extending tabs (289A, 289B) of resilient members (288A, 288B) and outwardly extending tabs (238A, 238B, 238C, 238D) of shaft assembly (230). It should be understood that this proximal movement will accommodate threading of stud (13) of transducer assembly (12) into the proximal end of the waveguide.

Figure 13:
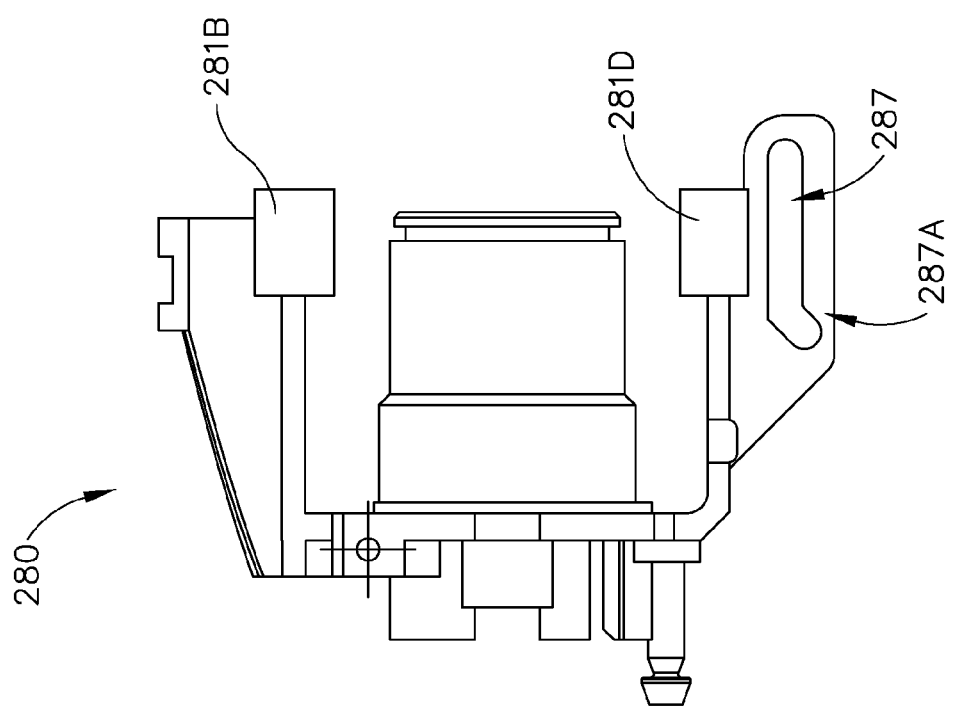
FIG. 13 depicts a side elevational view of a housing of the handle assembly of FIG. 6.

As best seen in FIGS. 11 and 14A-14D, handle assembly (220) comprises a locking member (266) that is slidably and rotatably coupled to housing (280) via a pin (267) passing through a slot (287) formed in a bottom of housing (280). Slot (287) is best seen in FIG. 13. Pin (267) is best seen in FIGS. 14A-14D. A distal portion of locking member (266) comprises a pair of teeth (268) that are configured to engage a pair of teeth (235) extending from the proximal portion of shaft assembly (230) as best seen in FIG. 10. As will be discussed in more detail below, pivotal movement of trigger (228) causes teeth (268) of locking member (266) to engage teeth (235) of shaft assembly (230). In particular, pivotal movement of trigger (228) toward pistol grip (224) causes proximal longitudinal translation of locking member (266) and vice versa. Trigger (228) is coupled with locking member (266) via a linkage (229) such that rotation of trigger (228) causes longitudinal translation of locking member (266). A first end of linkage (229) is rotatably coupled with a proximal portion of trigger (228). A second end of linkage (229) is rotatably coupled with a proximal portion of locking member (266). As best seen in FIG. 13, A distal portion (287A) of slot (287) is angled such that as locking member (266) is driven longitudinally proximally via pivotal movement of trigger (228) toward pistol grip (224), the angled portion of slot (287) causes the proximal portion of locking member (266) to be driven upward via pin (267) to thereby engage teeth (235) of shaft assembly (230).

Figure 14A:
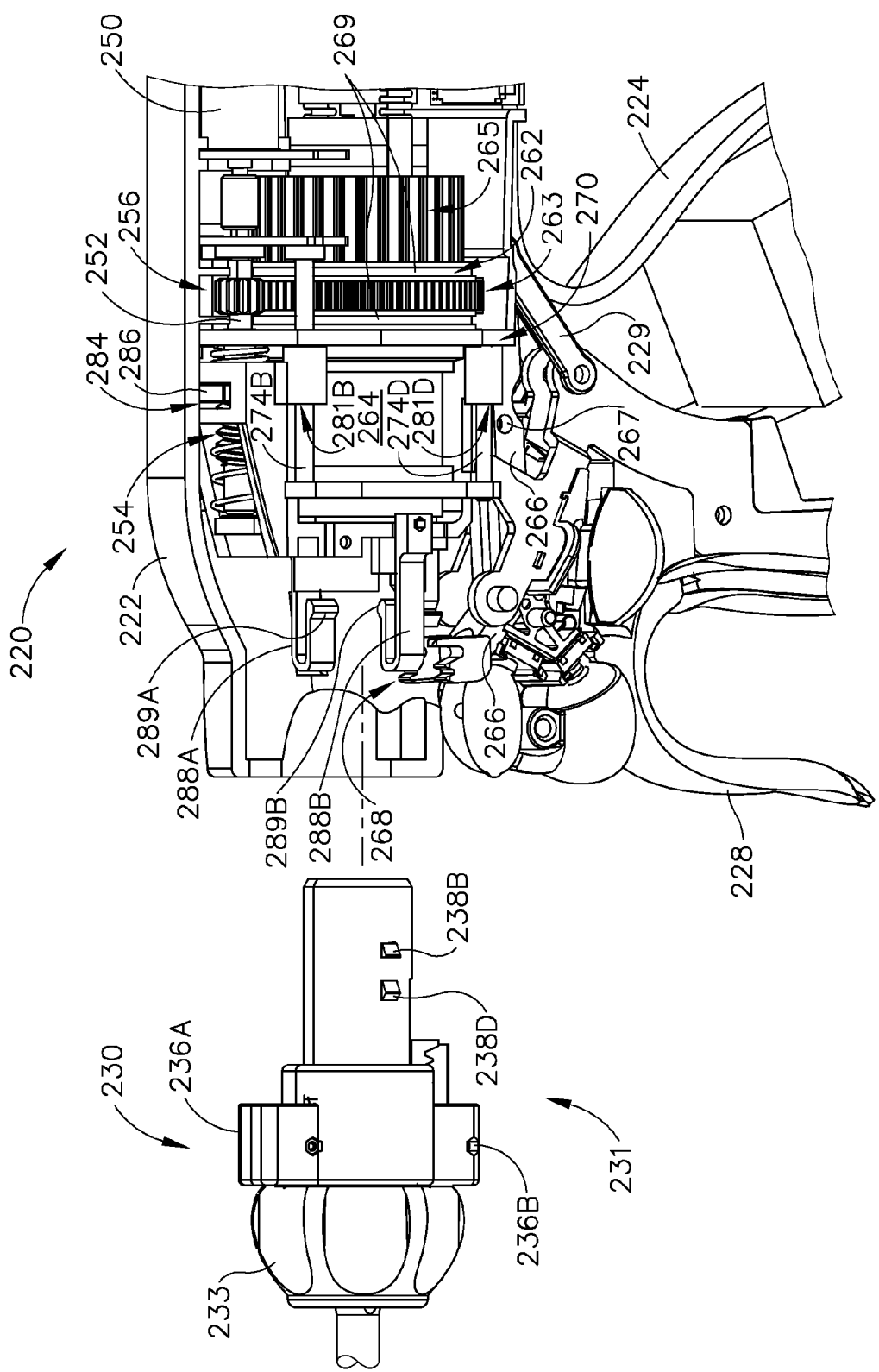
FIG. 14A depicts a side elevational view of the instrument of FIG. 5, with a portion of the handle assembly removed to reveal internal components of the handle assembly, and with the shaft assembly decoupled from the handle assembly.
Figure 14B:
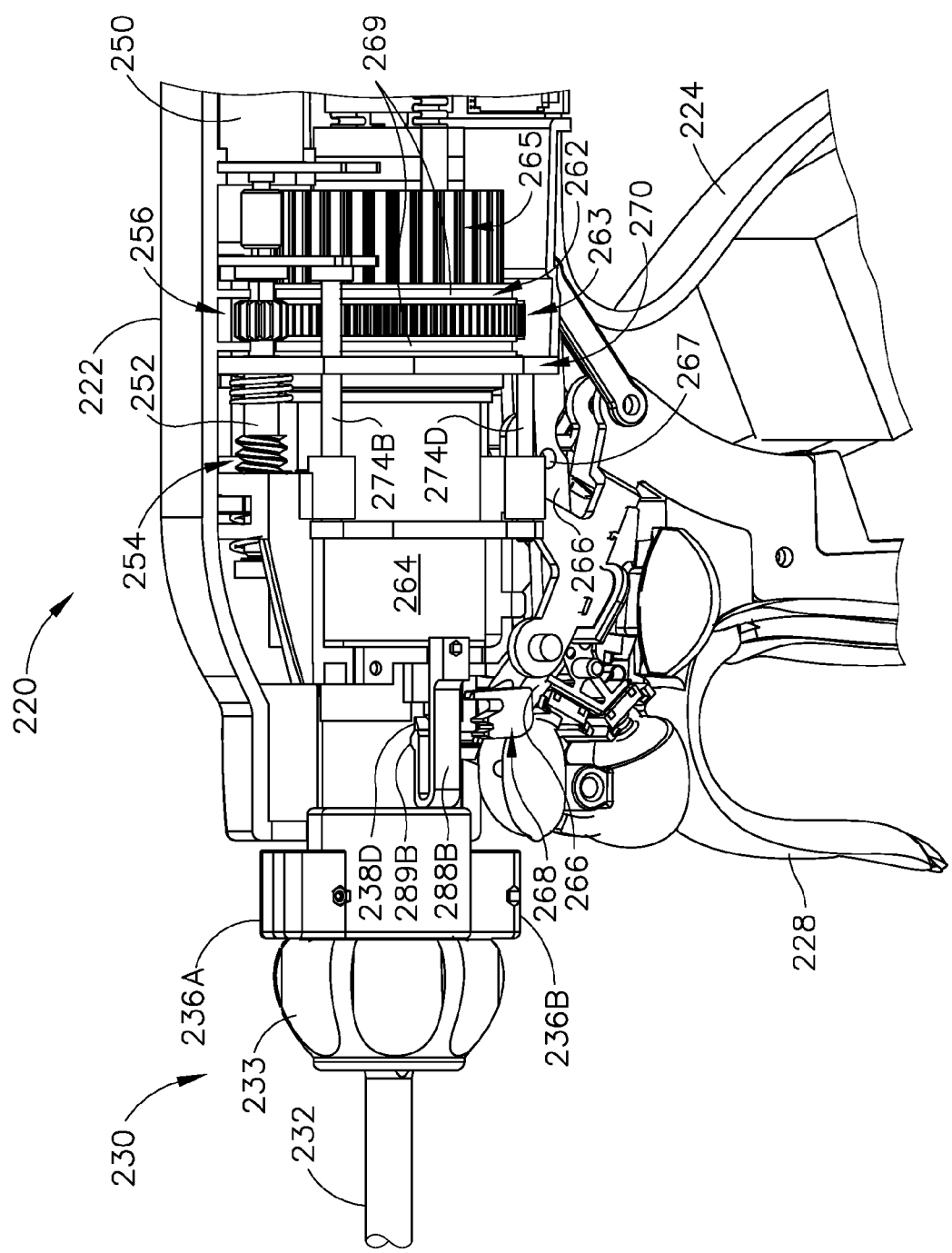
FIG. 14B depicts a side elevational view of the instrument of FIG. 5, with a portion of the handle assembly removed to reveal internal components of the handle assembly, and with the shaft assembly positioned within the handle assembly.

FIGS. 14A-14D show the steps of securing shaft assembly (230) within handle assembly (220). Shaft assembly (230) is moved proximally from a position distal of handle assembly (220) (FIG. 14A) such that inwardly extending tabs (289A, 289B) of resilient members (288A, 288B) have engaged outwardly extending tabs (238A, 238B, 238C, 238D) of shaft assembly (230) as shown in FIG. 14B. In this position, a proximal end of the waveguide contacts threaded stud (13) of transducer assembly (12). Also in this position, housing (280) is in a distal position along guide posts (274A, 274B, 274C, 274D). Motor (250) is then activated. By way of example only, motor (250) may be automatically activated by a sensor that detects the positioning of shaft assembly (230) as shown in FIG. 14B. Alternatively, motor (250) may be manually activated by the operator depressing a button or other input feature. As yet another merely illustrative example, motor (250) may be activated by a combination of conditions including a sensor detecting the positioning of shaft assembly (230) as shown in FIG. 14B and an operator depressing a button, etc. Other suitable ways in which motor (250) may be activated will be apparent to those of ordinary skill in the art in view of the teachings herein.

Figure 14C:
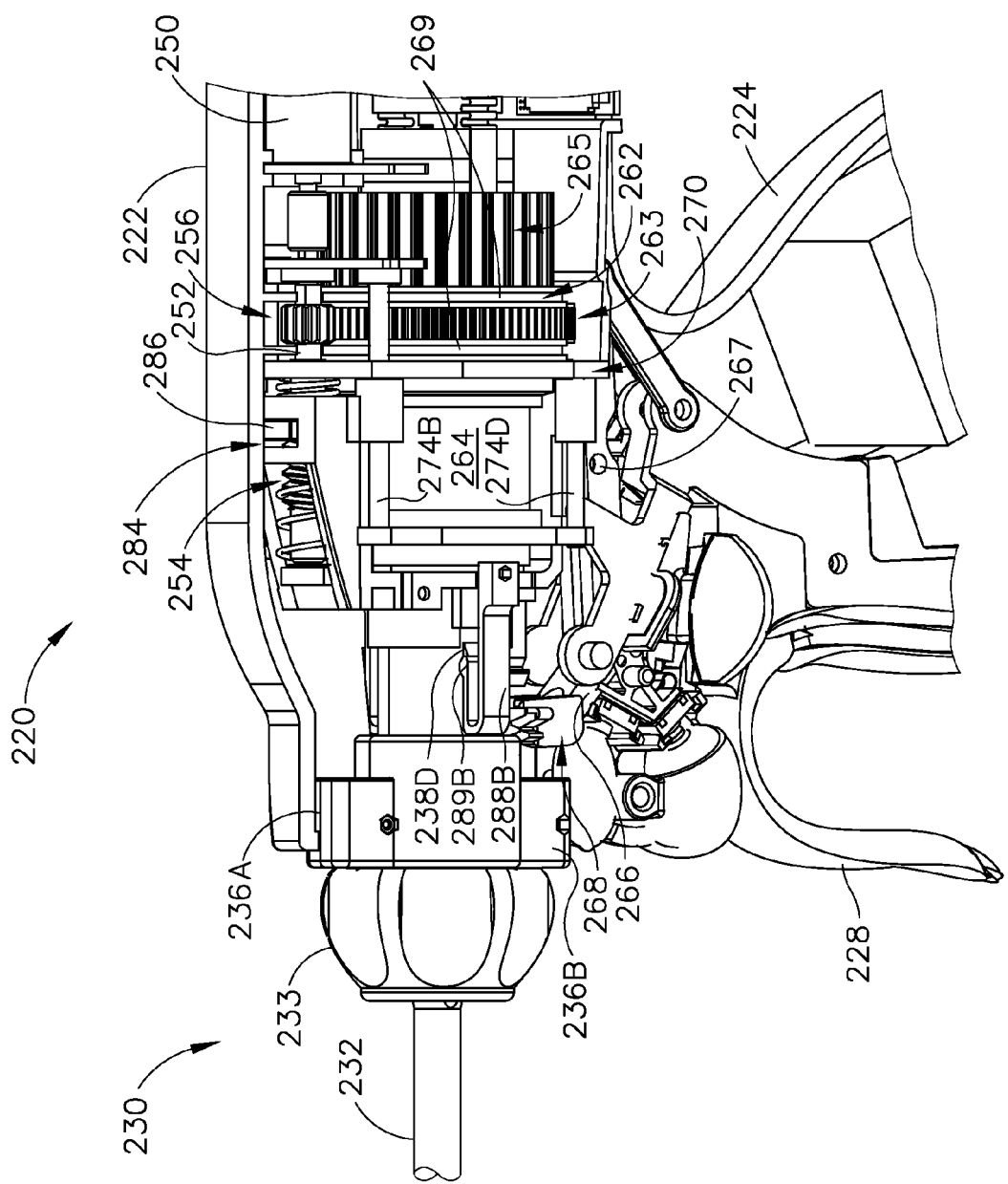
FIG. 14C depicts a side elevational view of the instrument of FIG. 5, with a portion of the handle assembly removed to reveal internal components of the handle assembly, and with the shaft assembly acoustically coupled with a transducer assembly in the handle assembly.
Figure 14D:
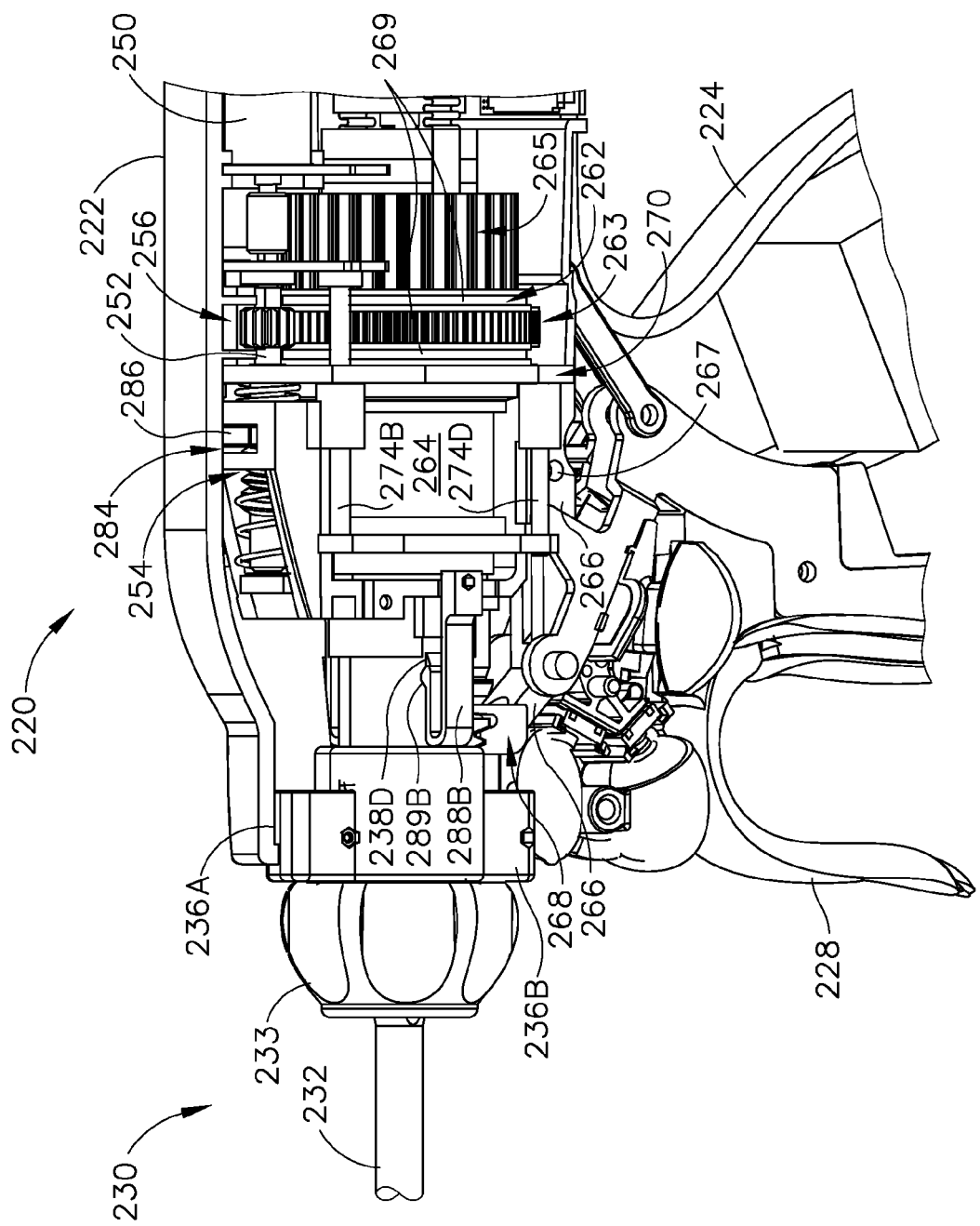
FIG. 14D depicts a side elevational view of the instrument of FIG. 5, with a portion of the handle assembly removed to reveal internal components of the handle assembly, and with the shaft assembly mechanically coupled with a trigger of the handle assembly.
Figure 16:
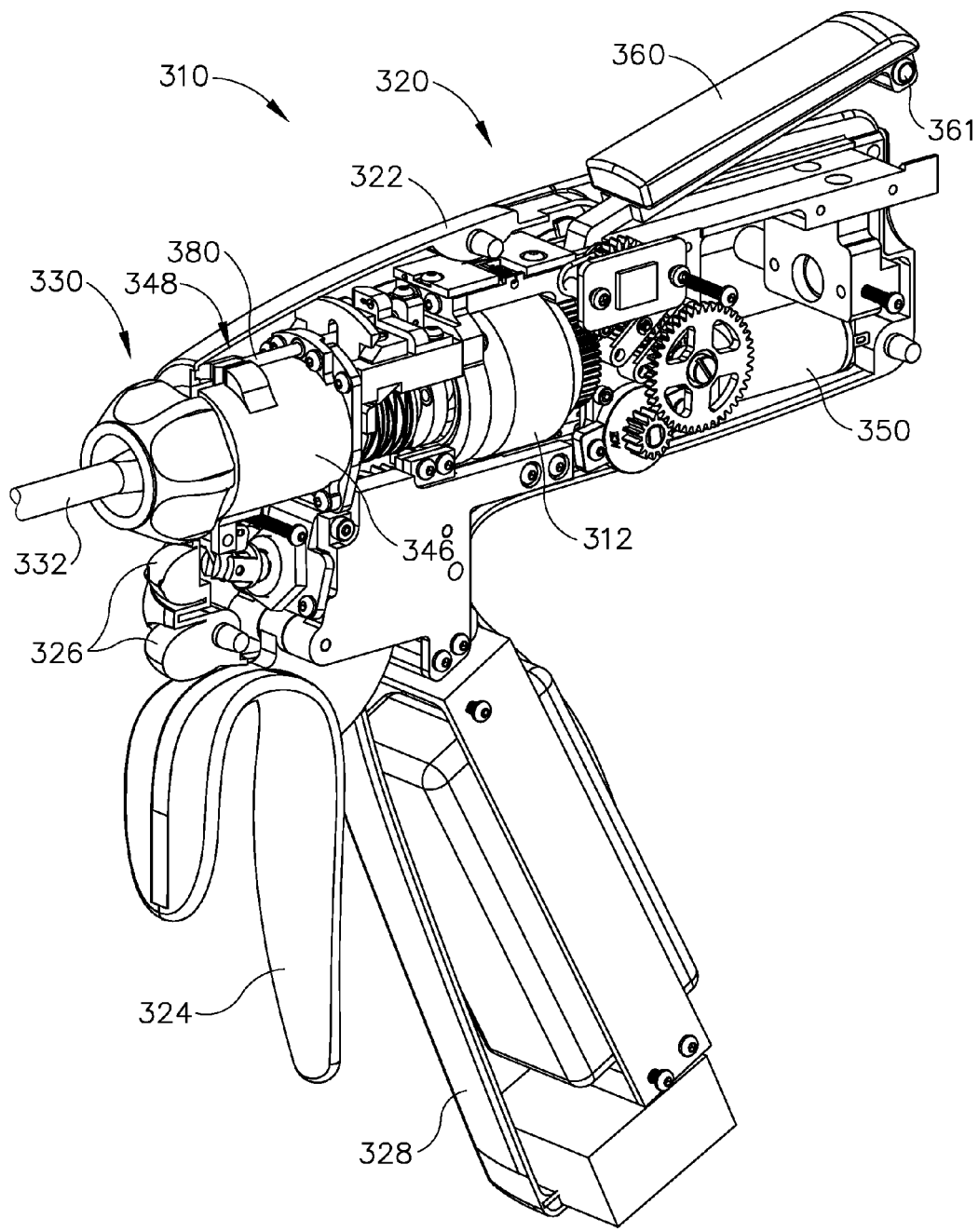
FIG. 16 depicts a perspective view of a handle assembly of the instrument of FIG. 15, with a portion of a handle assembly of the instrument removed to reveal internal components of the handle assembly.

As motor (250) rotates, axle (252) is rotated such that ring gear (262), housing (264), and transducer assembly (12) also rotate relative to body (222). Shaft assembly (230) remains rotationally stationary relative to body (222) such that stud (12) of transducer assembly (12) is threaded onto the threaded bore defined in the proximal end of the waveguide. The splined engagement between ring gear (262) and housing (264) allows housing (264) and transducer assembly (12) to translate distally within body (222) as stud (13) threadably advances into the proximal end of the waveguide. In some versions, a coil spring, leaf spring, or other resilient member provides a distal bias to housing (264), further promoting distal advancement of housing (264) and transducer assembly (12) as stud (13) threadably advances into the proximal end of the waveguide. Also as axle (252) rotates, threaded region (254) of axle (252) engages threaded interior bore of threaded member (286) such that rotation of axle (252) causes proximal longitudinal translation of threaded member (286) and housing (280) toward a proximal position as shown in FIG. 14C. In this proximal position, housing (280) drives shaft assembly (230) proximally such that proximal engagement housing (231) of shaft assembly (230) is positioned within keyed bore (223) of handle assembly (220). Also in this proximal position, stud (13) of transducer assembly (12) has been completely threaded into the waveguide. FIG. 14D shows locking member (266) engaged with housing (280) via pivotal movement of trigger (228) toward pistol grip (224).

In some versions, a portion of shaft assembly (230) (e.g., one of longitudinal projections (236A, 236B), etc.) includes an RFID chip and/or other identifying feature that identifies the operating modality of shaft assembly (230). Handle assembly (220) may include a reader and a control logic that are operable to detect such an identifying feature and react accordingly. By way of example only, handle assembly (220) may be configured to operate with shaft assemblies (230) that include an ultrasonic blade (242) at end effector (240) and shaft assemblies that include RF electrosurgical features at the end effector. In some such versions, the reader may detect that a shaft assembly (230) that includes an ultrasonic blade (242) is being coupled with handle assembly (220). The control logic may activate motor (250) accordingly to couple transducer assembly (12) with the waveguide of shaft assembly (230). Alternatively, the reader may detect that a shaft assembly that includes RF electrosurgical features at the end effector is being coupled with handle assembly (220). The control logic may refrain from activating motor (250) accordingly. Even in instances where handle assembly (220) is unable to couple with shaft assemblies that use different operating modalities, an identifier or other feature of shaft assembly (230) may nevertheless activate a complementary feature in handle assembly (220), which may in turn activate motor (250) in response to detection of shaft assembly (230) at the distal end of handle assembly (220).

In addition or in the alternative, handle assembly (220) may include a user input feature that is operable to eject shaft assembly (230) from handle assembly (220). For instance, this user input feature may cause motor (250) to operate in reverse to decouple the waveguide from transducer assembly (12) and to decouple shaft assembly (250) from housing (280). As yet another merely illustrative example, handle assembly (220) may include one or more motion sensors (e.g., accelerometers, etc.) that may be used to manage energy conservation based on whether and/or how an operator is using instrument (210).

It should also be understood that handle assembly (220) may include one or more features configured to ensure that an appropriate amount of torque (e.g., between approximately 5 inch-pounds and approximately 10 inch-pounds, etc.) is applied to the coupling of stud (13) with the waveguide. For instance, an encoder, one or more hall effect sensors, one or more reed switches, and/or various other kinds of components may be used to track the turns of stud (13); and a control logic may stop motor (250) when stud (13) as turned through an angular range associated with an appropriate torque value. As another merely illustrative example, a control module may track a back electromotive force (EMF) associated with motor (250); and stop motor (250) when the back EMF has reached a value associated with an appropriate torque value.

As yet another merely illustrative example, a clutch feature such as a ratcheting assembly described below, a one-way bearing assembly, and/or some other feature may provide slipping of drive features when an appropriate torque value is achieved at the coupling of the threaded stud of the transducer and the waveguide. This slipping may cause a sudden drop in the back EMF associated with motor (250), a sudden increase in the rotation speed of a now "freewheeling" drive component, and/or some other detectable condition. This drop in the back EMF, increase in rotation speed, or other change in condition may be detected by a control module to trigger deactivation of motor (250). Other suitable ways in which one or more sensors may be used, as well as other suitable ways in which motor (350)

may be controlled (e.g., to deactivate motor (250) upon a certain torque value being achieved, etc.), will be apparent to those of ordinary skill in the art in view of the teachings herein. Furthermore, other suitable features, components, and functionalities that may be incorporated into handle assembly (220) will be apparent to those of ordinary skill in the art in view of the teachings herein.

It should also be understood that shaft assembly (230) may be varied in numerous ways. By way of example only, in some versions of shaft assembly (230), shaft assembly (230) is operable to selectively transition between a first configuration where outer sheath (232), the inner tube, the waveguide, and end effector (240) are rotatable relative to proximal engagement housing (231); and a second configuration where outer sheath (232), the inner tube, the waveguide, and end effector (240) are not rotatable relative to proximal engagement housing (231). For instance, a rotation knob (233) of shaft assembly (230) may be keyed to outer sheath (232) may be configured to translate between a proximal position and a distal position along outer sheath (232). When rotation knob (233) is in the proximal position, features within proximal engagement housing (231) may lock the rotational position of outer sheath (232), the inner tube, the waveguide, and end effector (240) relative to proximal engagement housing (231). When rotation knob (233) is in the distal position, features within proximal engagement housing (231) may allow outer sheath (232), the inner tube, the waveguide, and end effector (240) to rotate relative to proximal engagement housing (231). Moreover, a resilient feature may bias rotation knob (233) to the proximal position, such that the operator must overcome this bias in order to move rotation knob (233) distally to provide rotation of shaft assembly (230). This may ensure that outer sheath (232), the inner tube, the waveguide, and end effector (240) are only rotatable relative to proximal engagement housing (231) after shaft assembly (230) has been coupled with handle assembly (220) as described above. This may also prevent the waveguide from rotating during the coupling operation as described above.

In some versions where shaft assembly (230) is operable to selectively transition between a first configuration where outer sheath (232), the inner tube, the waveguide, and end effector (240) are rotatable relative to proximal engagement housing (231); and a second configuration where outer sheath (232), the inner tube, the waveguide, and end effector (240) are not rotatable relative to proximal engagement housing (231); housing (280) may be operable to selectively transition shaft assembly (230) between the first configuration and the second configuration. For instance, when housing (280) is in a distal position within body (222), housing (280) may place shaft assembly (230) in a configuration where outer sheath (232), the inner tube, the waveguide, and end effector (240) are not rotatable relative to proximal engagement housing (231). Conversely, when housing (280) is in a proximal position within body (222), housing (280) may place shaft assembly (230) in a configuration where outer sheath (232), the inner tube, the waveguide, and end effector (240) are rotatable relative to proximal engagement housing (231). It should be understood that threaded region (254) of axle (252) may drive housing (280) between the distal and proximal positions. Thus, motor (250) may be operable to transition shaft assembly (230) between rotationally locked and rotationally unlocked configurations, in coordination with the threaded coupling of transducer assembly (12) with the waveguide. In other words, the above noted components may provide shaft assembly (230) in a rotationally locked configuration while transducer assembly (12) is being threadably coupled with the waveguide; then provide shaft assembly (230) in a rotationally unlocked configuration once transducer assembly (12) has been suitably coupled with the waveguide. Other suitable features, components, and functionalities that may be incorporated into shaft assembly (230) will be apparent to those of ordinary skill in the art in view of the teachings herein.

B. Exemplary Ultrasonic Surgical Instrument with Coupling Via Motor and Lever

FIGS. 15-24D show another exemplary instrument (310) having a shaft assembly (330) that is configured to selectively couple with a handle assembly (320) and transducer assembly (12) through activation of a motor (350). Instrument (310) of the present example is configured to operate substantially similar to instruments (10, 210) discussed above except for the differences discussed below. In particular, instrument (310) is configured to clamp tissue between a pivoting clamp arm (344) and an ultrasonic blade (342) of an end effector (340); and cut/seal the tissue by ultrasonically activating blade (342).

Instrument (310) of the present example comprises handle assembly (320), a shaft assembly (330), and an end effector (340). Shaft assembly (330) comprises an outer sheath (332), an inner tube (not shown) slidably disposed within outer sheath (332), and a waveguide (not shown) disposed within the inner tube. As with inner tube (34) of instrument (10) discussed above, longitudinal translation of the inner tube of the present example causes actuation of clamp arm (344) of end effector (340). Handle assembly (320) comprises a body (322) including a pistol grip (324) and a pair of buttons (326). Handle assembly (320) also includes a trigger (328) that is pivotable toward and away from pistol grip (324). Trigger (328) is pivotably coupled to handle assembly (320). Pivotal movement of trigger (328) causes longitudinal translation of the inner tube to thereby cause pivotal movement of clamp arm (344) toward and away from ultrasonic blade (342).

Figure 17:
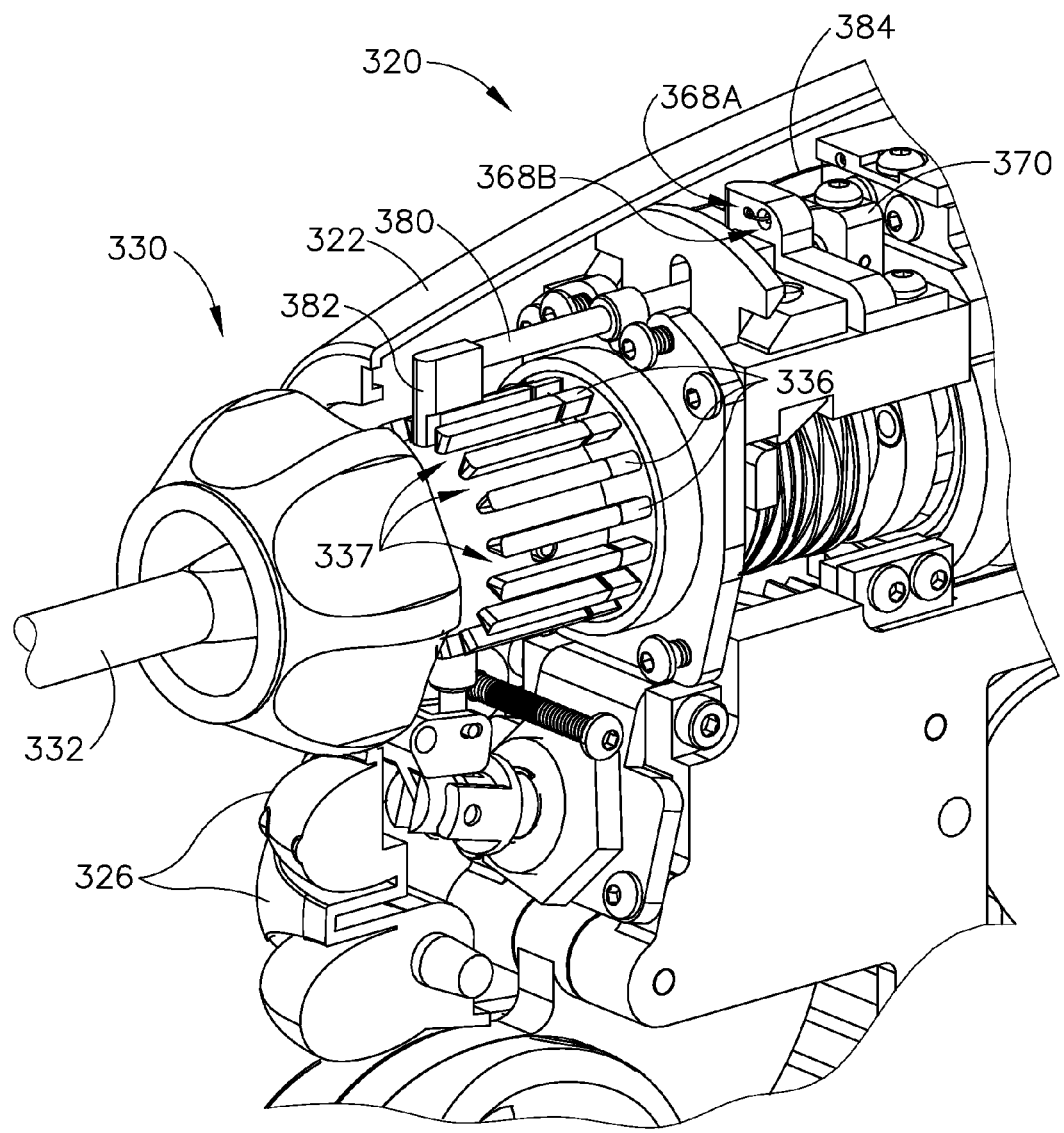
FIG. 17 depicts a detailed perspective view of a distal portion of the handle assembly of FIG. 16.
Figure 18:
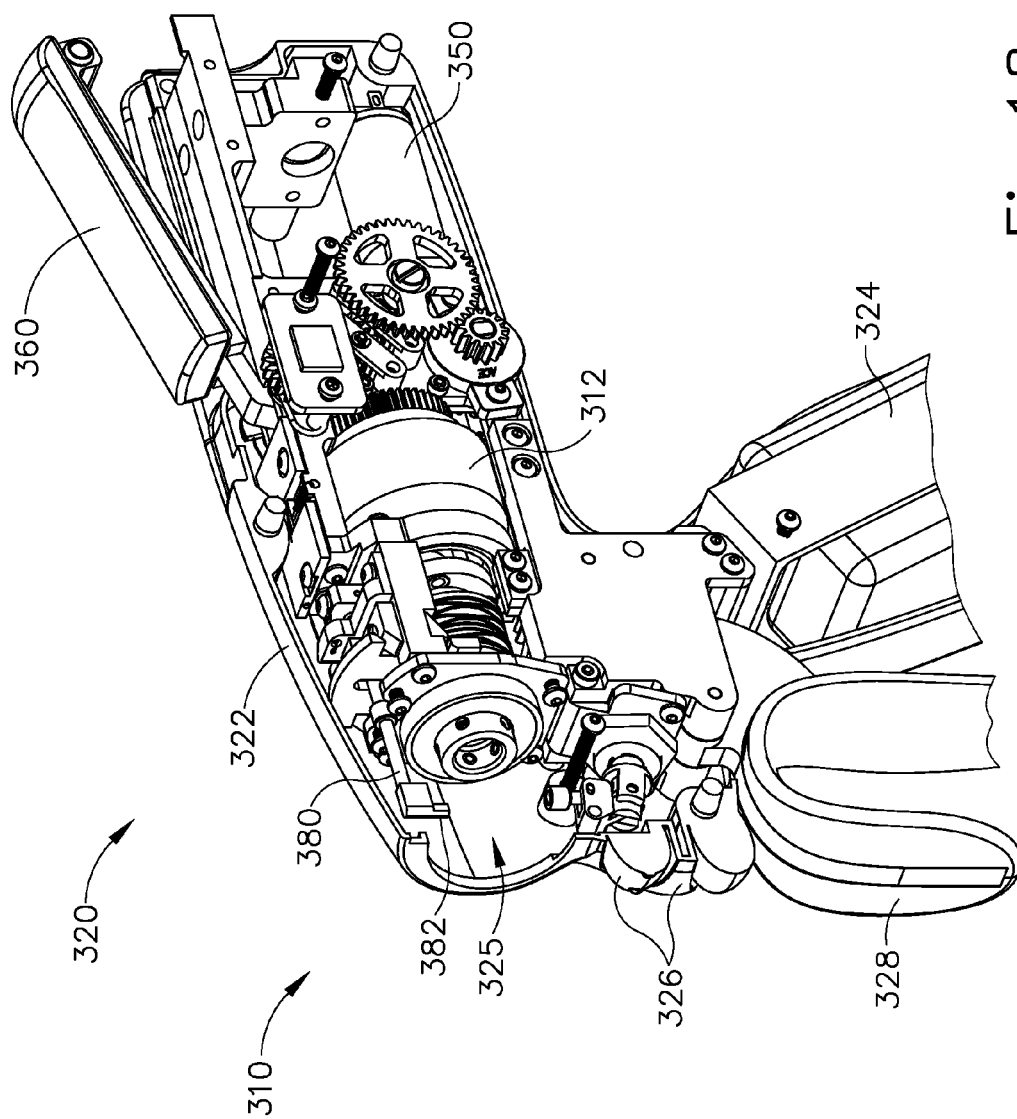
FIG. 18 depicts a perspective view of the handle assembly of FIG. 16, with a portion of a handle assembly of the instrument removed to reveal internal components of the handle assembly, and with a shaft assembly omitted.
Figure 19:
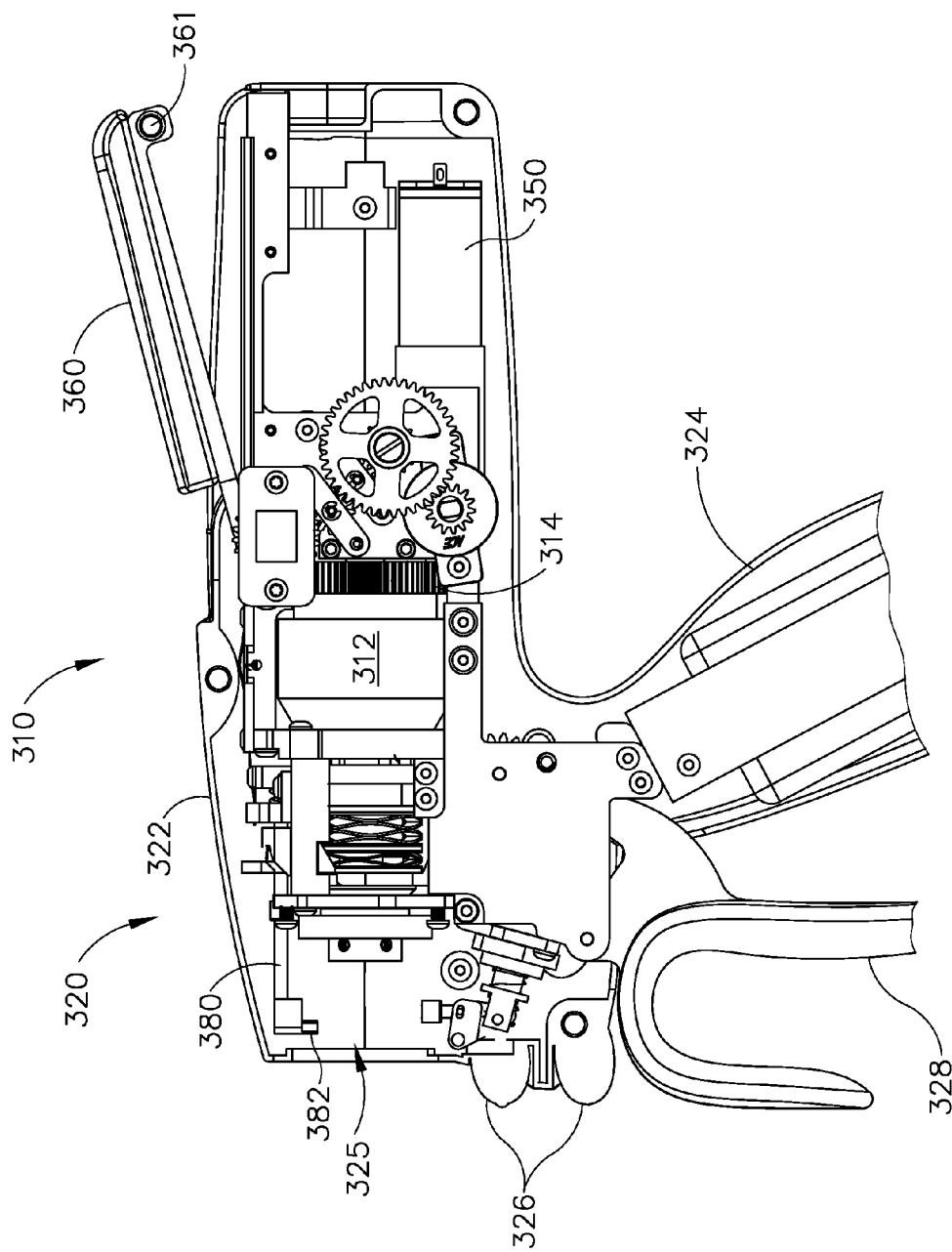
FIG. 19 depicts a side elevational view of the handle assembly of FIG. 16, with a portion of a handle assembly of the instrument removed to reveal internal components of the handle assembly, and with a shaft assembly omitted.
Figure 22A:
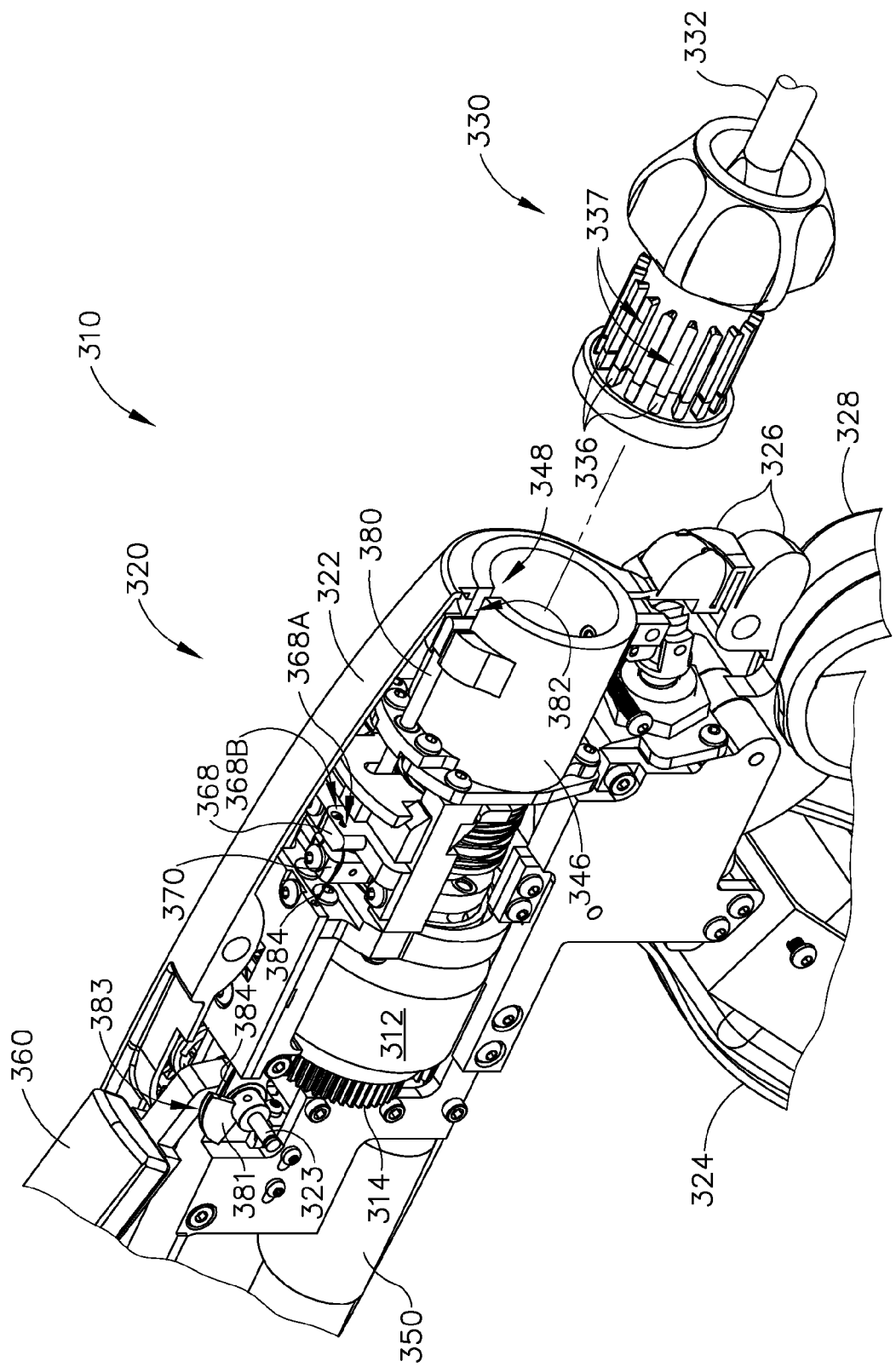
FIG. 22A depicts a perspective view of a distal portion of the handle assembly of FIG. 16, with a portion of a handle assembly of the instrument removed to reveal internal components of the handle assembly, and with a shaft assembly decoupled from the handle assembly.
Figure 22B:
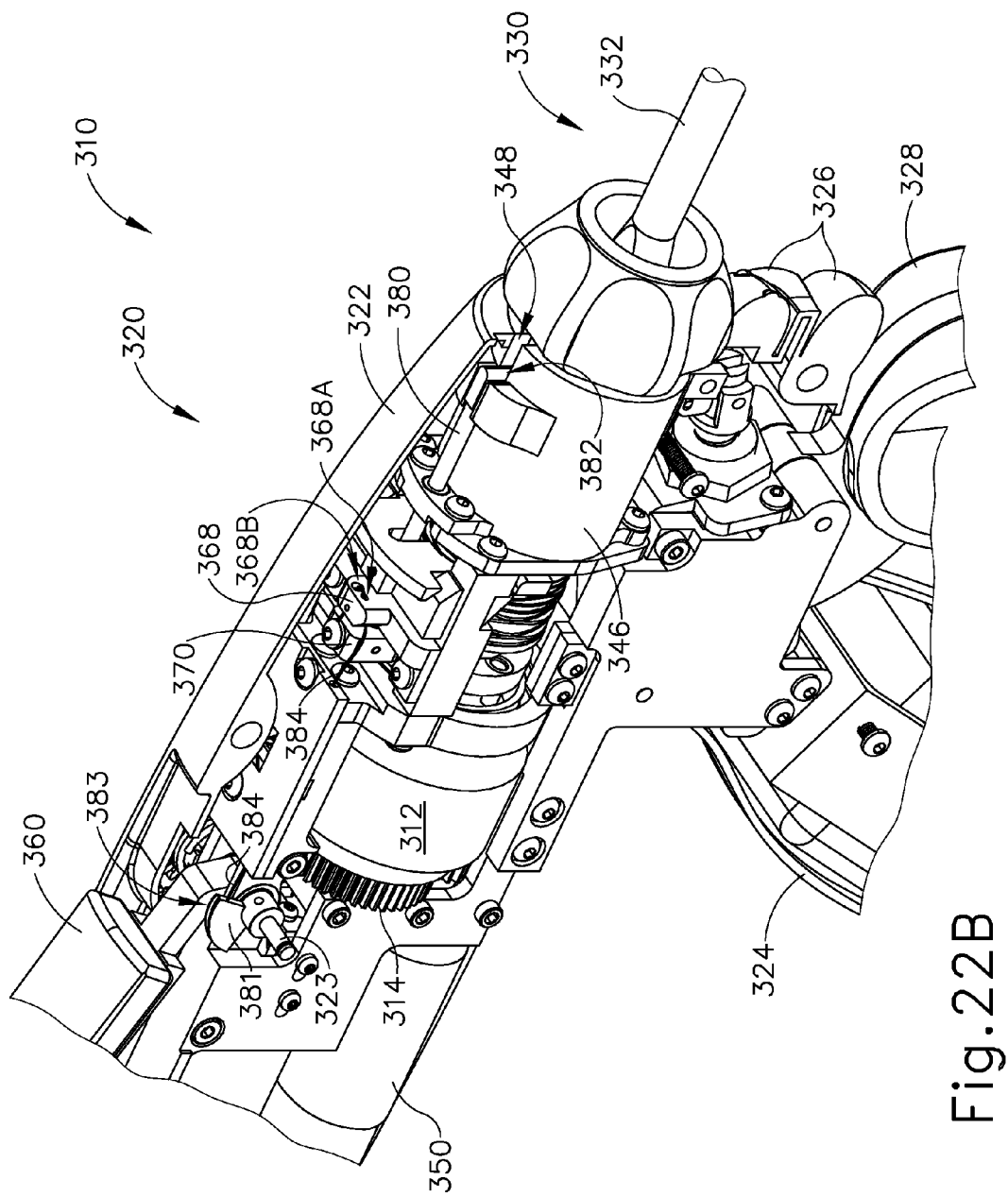
FIG. 22B depicts a perspective view of a distal portion of the handle assembly of FIG. 16, with a portion of a handle assembly of the instrument removed to reveal internal components of the handle assembly, and with the shaft assembly positioned within the handle assembly.

As will be discussed in more detail below, handle assembly (320) is configured to receive and selectively secure handle assembly (330) therein. As shown in FIGS. 18-19 distal end of body (322) of handle assembly (320) defines a circular bore (325) that is configured to receive a proximal portion (331) of shaft assembly (330). As shown in FIGS. 22A-22B, a socket housing (346) is positioned within circular bore (325). Socket housing (346) is configured to insertingly receive proximal portion (331) of shaft assembly (330). As shown in FIG. 17, proximal portion (331) of shaft assembly (330) comprises a plurality of longitudinal splines (336) extending from an exterior surface of shaft assembly (230) and arranged in an angular array. Splines (336) define a plurality of longitudinal slots (337) between consecutive splines (336). As will be discussed in more detail below, a locking member (380) is configured to move into and out of slots (337) to engage adjacent splines (336), to thereby prevent rotation of shaft assembly (330) relative to handle assembly (320) during assembly of instrument (310).

A transducer assembly (not shown), which may be configured and operable like transducer assembly (12) described above, is secured within a transducer housing (312) in body (322) of handle assembly (320). Transducer housing (312) is configured to rotate within body (322) of handle assembly (320). The transducer is fixedly secured within transducer housing (312), such that the transducer rotates with transducer housing (312) relative to body (322) of handle assembly (320). A drive gear (314) is fixedly secured to the proximal end of transducer housing (312), such that drive gear (314) may be driven to rotate transducer housing (312)

relative to body (322) of handle assembly (320). It should be understood that the waveguide of shaft assembly (330) may include a threaded bore that is configured to receive a complementary threaded stud of the transducer assembly, similar to the relationships described elsewhere herein, to mechanically and acoustically couple the transducer assembly with the waveguide upon sufficient rotation of the transducer assembly relative to shaft assembly (330).

Figure 21:
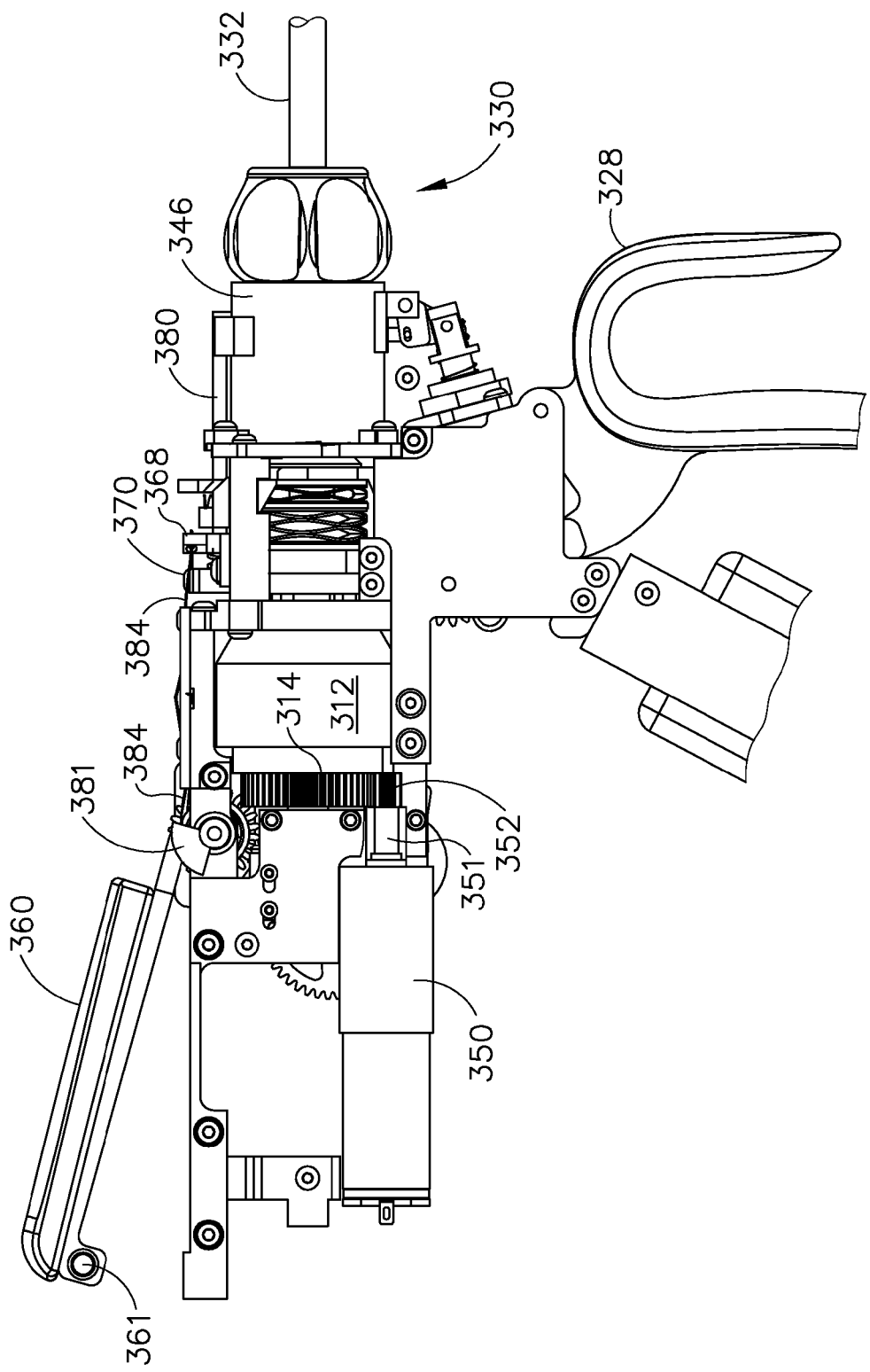
FIG. 21 depicts a side elevational view of the interior components of the handle assembly of FIG. 16.

Handle assembly (320) comprises a plurality of internal components configured to selectively secure the transducer assembly of handle assembly (320) with the waveguide of shaft assembly (330). In particular, handle assembly (320) comprises a motor (350) that is operable to secure the transducer assembly of handle assembly (320) with the waveguide of shaft assembly (330) in response to pivoting of a lever arm (360) relative to handle assembly (320). Motor (350) is operable to rotate a drive gear (352), which is coaxially aligned with and secured to the integral drive shaft (351) of motor (350) as best seen in FIG. 21. As also best seen in FIG. 21, the teeth of drive gear (352) mesh with the teeth of gear (314), such that motor (350) is operable to drive rotation of transducer housing (312) relative to body (322) of handle assembly (320) through meshing engagement of gears (352, 314).

As best seen in FIGS. 23A-23D, lever arm (360) is rotatably coupled with a chassis (321) in body (322) via a pin (323) such that lever arm (360) is rotatable relative to body (322) between a plurality of rotational positions. Lever arm (360) is also coupled to a gear (362) via pin (323) such that pivoting of lever arm (360) about pin (323) causes rotation of gear (362). Gear (362) is rotatably supported by chassis (321) and meshes with another gear (363), which is also rotatably supported by chassis (321). Gear (363) meshes with another gear (364), which is also rotatably supported by chassis (321). Gear (364) meshes with another gear (365), which is also rotatably supported by chassis (321). Gear (365) is secured to an axle (366) with another gear (367), such that gears (365, 367) rotate together with axle (366) relative to chassis (321). A portion of gear (367) is omitted in FIG. 23B to better depict gear (365) and the meshing engagement between gears (364, 365). Gear (367) meshes with another gear (369), which is secured to an oblong pin (369A) of a rotary damper (369B). Rotary damper (369B) is fixedly secured to chassis (321). Rotary damper (369B) comprises a conventional rotary damper that is configured to slow the actuation of lever arm (360), reducing the angular velocity at which lever arm (360) pivots and providing some degree of tactile resistance to pivoting of lever arm (360).

While not shown, a conventional sensor is used to track pivotal movement of lever arm (360). A control module is in communication with this sensor and motor (350), and is thus configured to activate motor (350) based on the pivotal position of lever arm (360) relative to body (322). By way of example only, such a sensor may comprise an encoder assembly with an encoder wheel coaxially positioned about pin (323) or about the shaft of any one of gears (362, 363, 364, 365, 367, 369). In addition or in the alternative, the sensor may include one or more hall effect sensors, one or more reed switches, and/or various other kinds of components. Various suitable kinds of components that may be used as one or more sensors to sense pivotal movement of lever arm (360) relative to body (322) will be apparent to those of ordinary skill in the art in view of the teachings herein. It should also be understood that a control module may activate motor (350) in response to one or more sensors detecting pivotal movement of lever arm (360) relative to body (322); and de-activate motor (350) upon lever arm (360) reaching a predetermined pivotal position relative to body (322).

It should also be understood that one or more features may be provided to ensure that an appropriate amount of torque (e.g., between approximately 5 inch-pounds and approximately 10 inch-pounds, etc.) is applied to the coupling of the ultrasonic transducer assembly with the acoustic waveguide. For instance, an encoder, one or more hall effect sensors, one or more reed switches, and/or various other kinds of components may be used to track the turns of the transducer assembly; and a control logic may stop motor (350) when the transducer assembly as turned through an angular range associated with an appropriate torque value. As another merely illustrative example, a control module may further track a back electromotive force (EMF) associated with motor (350); and de-activate motor (350) in response to the back EMF reaching a value associated with an appropriate torque value at the coupling of the threaded stud of the transducer and the waveguide. As yet another merely illustrative example, a clutch feature such as a ratcheting assembly described below, a one-way bearing assembly, and/or some other feature may provide slipping of drive features when an appropriate torque value is achieved at the coupling of the threaded stud of the transducer and the waveguide. This slipping may cause a sudden drop in the back EMF associated with motor (350), a sudden increase in the rotation speed of a now "freewheeling" drive component, and/or some other detectable condition. This drop in the back EMF, increase in rotation speed, or other change in condition may be detected by a control module to trigger deactivation of motor (350). Other suitable ways in which one or more sensors may be used, as well as other suitable ways in which motor (350) may be controlled (e.g., to deactivate motor (350) upon a certain torque value being achieved, etc.), will be apparent to those of ordinary skill in the art in view of the teachings herein.

Figure 20:
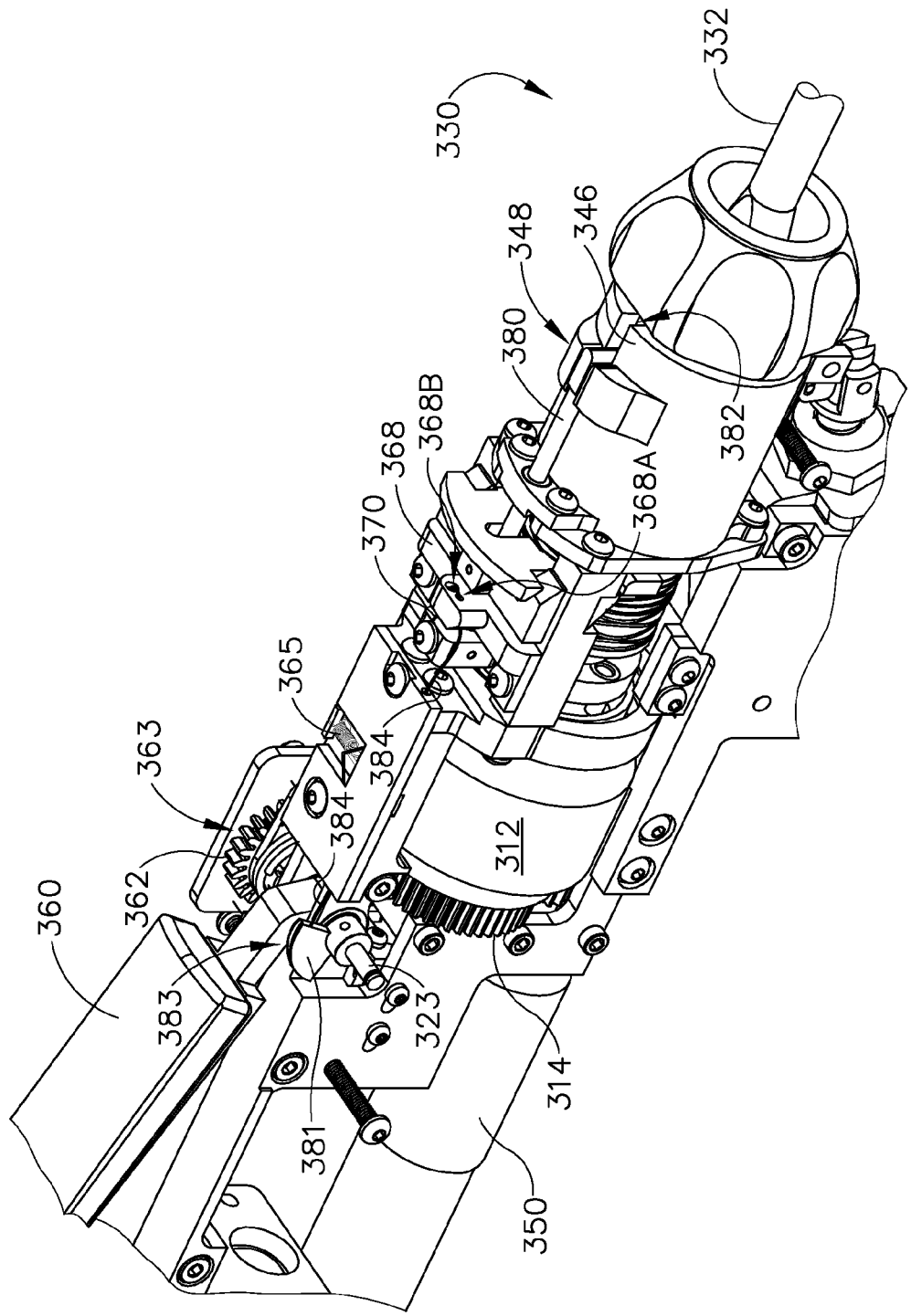
FIG. 20 depicts a perspective view of interior components of the handle assembly of FIG. 16.

As best seen in FIGS. 20 and 21, lever arm (360) is also coupled with a pulley member (381) via pin (323) such that rotation of lever arm (360) causes rotation of pulley member (381). Pulley member (381) defines an arcuate channel (383). A cable (384) is disposed within channel (383) of pulley member (381) such that rotation of pulley member (381) causes longitudinal translation of cable (384). As will be discussed in more detail below, longitudinal translation of cable (384) is selectively locks and unlocks rotation of shaft assembly (330) relative to handle assembly (320) via locking member (380). A distal portion of cable (384) slidably passes through a pair of through bores (368A, 368B) formed in a housing (368), such that cable (384) redirects by 180° through housing (368). A distal end of cable (384) is coupled to a longitudinally translatable member (370), which is proximal to housing (368), such that proximal longitudinal translation of cable (384) causes distal longitudinal translation of member (370). It should be understood that member (370) may be proximally biased such that cable (384) is distally biased as well. As best seen in FIG. 20, cable (384) is coupled with a tensioning spring (365) to thereby take up slack within cable (384). In particular, tensioning spring (365) pulls cable (384) laterally to resiliently shorten the effective length of cable (384) while cable (384) is laterally deformed by tensioning spring (365).

Member (370) is coupled to a proximal end of locking member (380) such that longitudinal translation of member (370) causes concurrent longitudinal translation of locking member (380). A distal end of locking member (380) comprises a downwardly extending tab (382). The distal end of locking member (380), including tab (382), is slidably disposed within a longitudinal slot (348) of a socket housing (346) positioned within a distal portion of handle assembly (320). (Housing (346) has been omitted from FIGS. 17-19, 24B, and 24D for the sake of clarity.) Tab (382) is configured to fit within slots (337) of shaft assembly (330) to thereby selectively lock and unlock shaft assembly (330). In particular, tab (382) is positioned within slots (337) of shaft assembly (330) when member (380) is in a proximal position, thereby preventing shaft assembly (330) from rotating relative to handle assembly (320). When member (380) is in a distal position, tab (382) is spaced distally of slots (337) and splines (336), thereby permitting shaft assembly (330) to rotate relative to handle assembly (320).

FIGS. 22A-24D show exemplary steps of securing shaft assembly (330) within handle assembly (320). As shown in the transition from FIG. 22A to FIG. 22B, a proximal portion of shaft assembly (320) is first inserted proximally into socket housing (346). As shown in FIG. 23A, lever arm (360) is at a first pivotal position relative to body (322) of handle assembly (320) at this stage. Also at this stage, locking member (380) is proximally positioned such that tab (382) is disposed in a slot (337) between adjacent splines (336), preventing shaft assembly (330) from rotating relative to handle assembly (320). The operator then begins to pivot lever arm (360) toward body (322), from the position shown in FIG. 23A to the position shown in FIG. 23B. This pivotal movement of lever arm (360) activates motor (350) to rotate gear (352) which in turn rotates the transducer assembly via gear (314) and transducer housing (312). As noted above, an encoder and/or other kind of sensor may detect pivotal movement of lever arm (360) from the position from the position shown in FIG. 23A to the position shown in FIG. 23B, with motor (350) being responsive to a signal from the encoder and/or other kind of sensor. In the present example, once lever arm (360) reaches the position shown in FIG. 23B, the transducer has been treaded into the threaded bore at the proximal end of the waveguide, but has not yet been fully tightened. In some instances, gear (362) is substituted with a sector gear with teeth arranged such that gear (362) does not engage gear (363) during the transition from the configuration shown in FIG. 23A to the configuration shown in FIG. 23B.

Figure 23A:
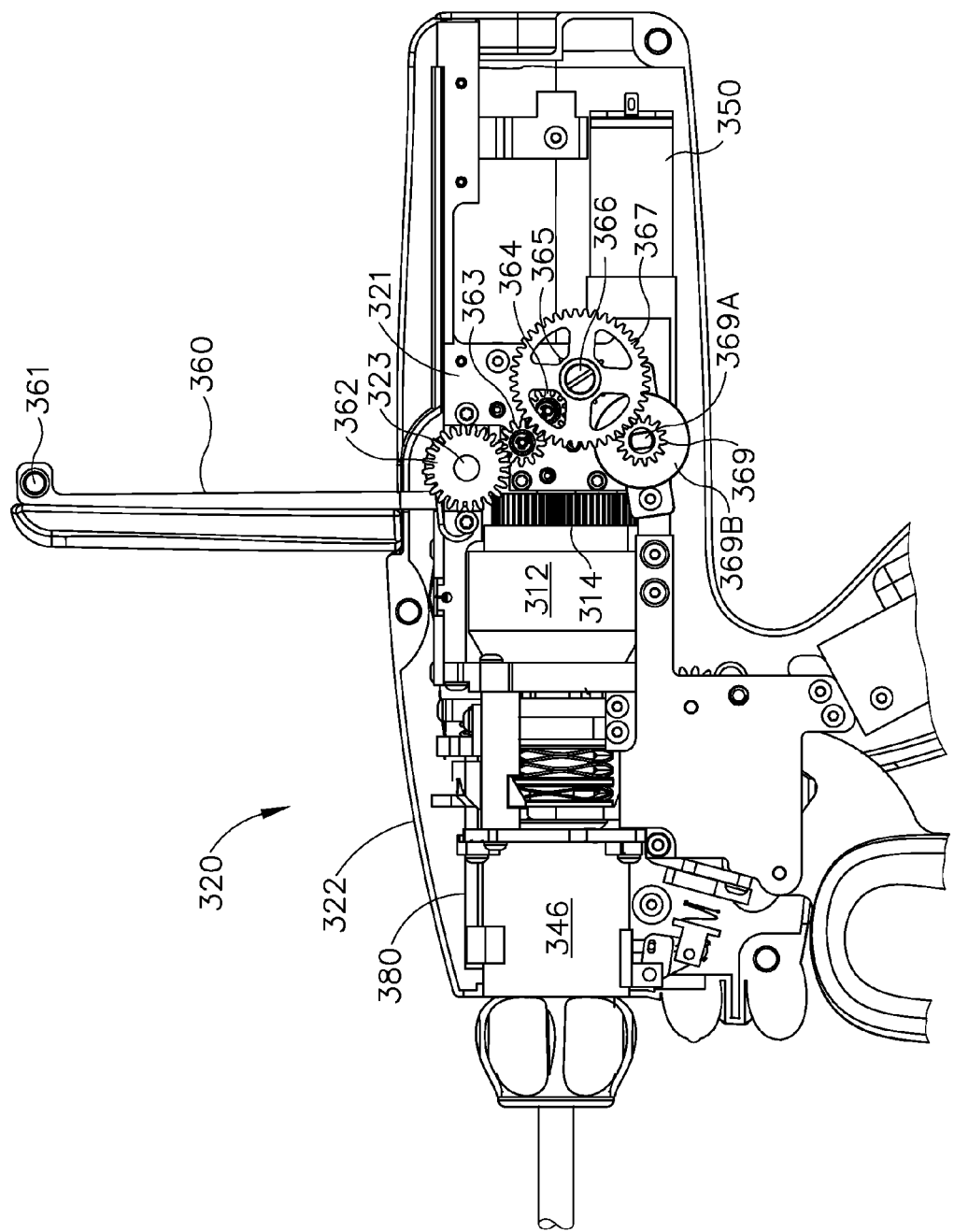
FIG. 23A depicts a side elevational view of a lever arm of the handle assembly of FIG. 16 in a first rotational position.
Figure 23B:
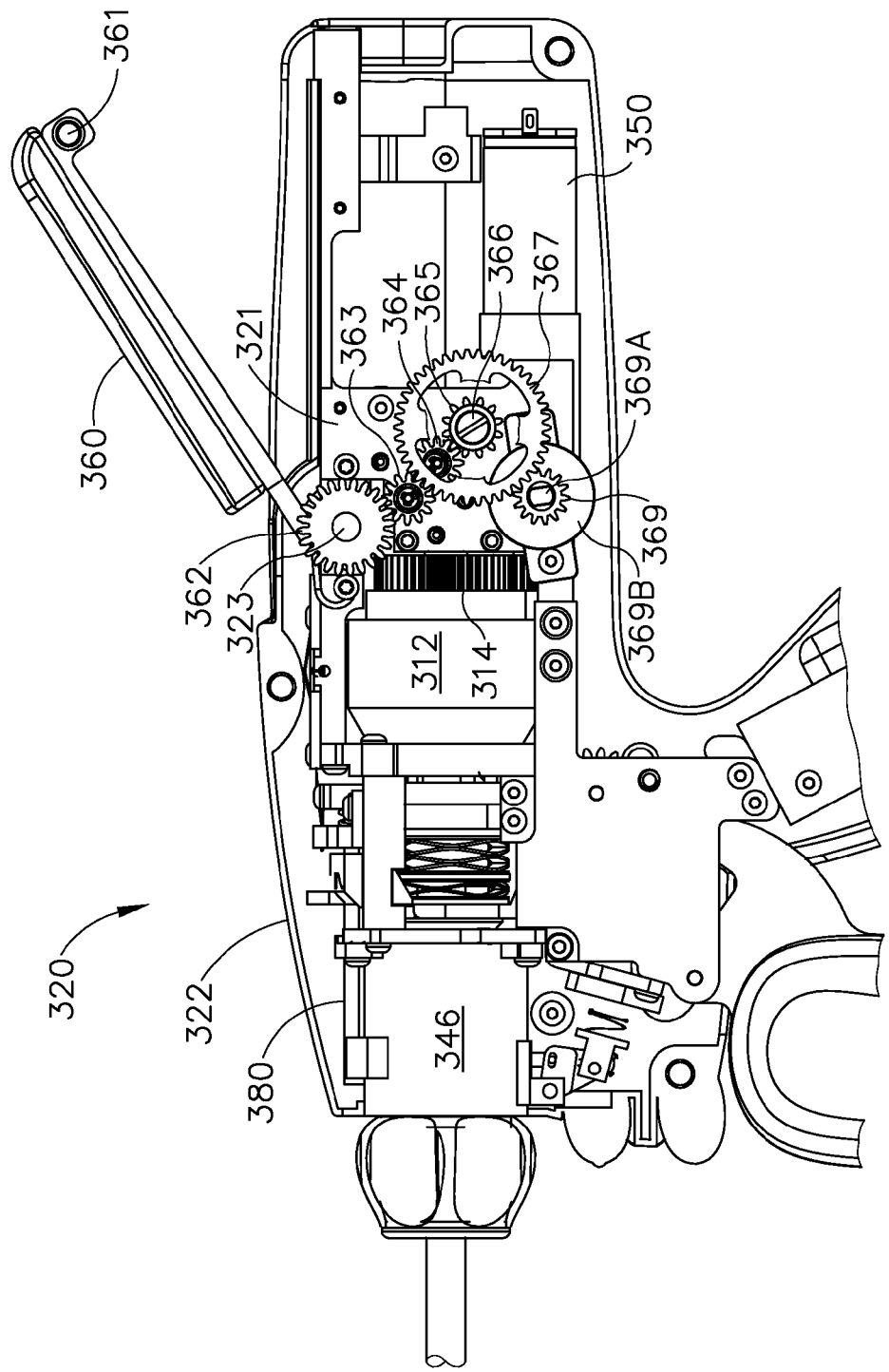
FIG. 23B depicts a side elevational view of the lever arm of the handle assembly of FIG. 16 moved into a second rotational position.
Figure 23C:
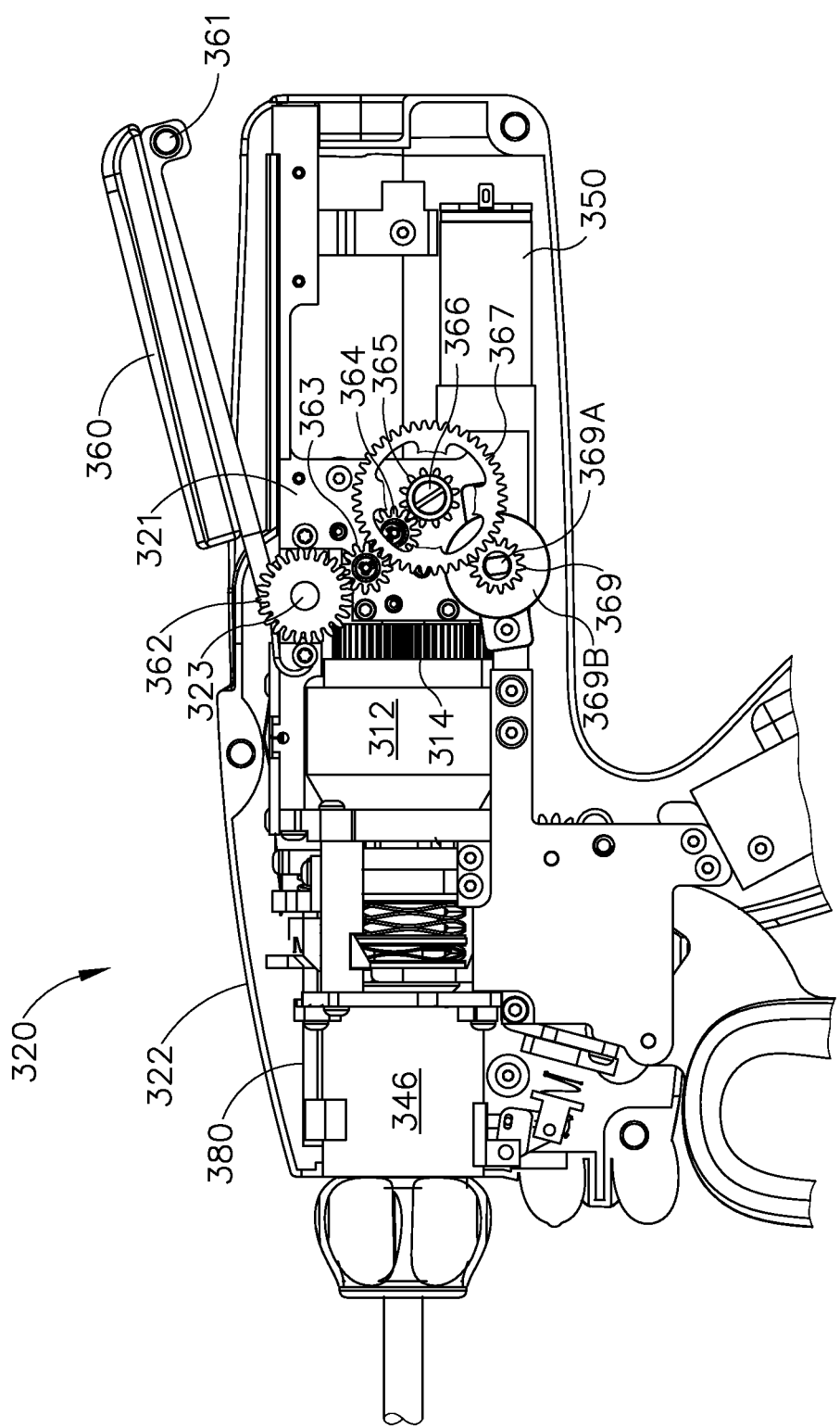
FIG. 23C depicts a side elevational view of the lever arm of the handle assembly of FIG. 16 moved into a third rotational position.

After reaching the stage shown in FIG. 23B, the operator continues to pivot lever arm (360) toward body (322) to the position shown in FIG. 23C. As lever arm (360) is pivoted from the position shown in FIG. 23B to the position shown in FIG. 23C, lever arm (360) drives gears (362, 363, 364, 365, 367, 369) such that rotary damper (369B) dampens the pivotal movement of lever arm (360) relative to body (322). Motor (350) continues to rotate transducer housing (312), thereby further threading the stud of the transducer into the threaded recess of the waveguide until a suitable level of torque is achieved at the coupling of the threaded stud with the waveguide. Thus, upon reaching the position shown in FIG. 23C, motor (350) has provided a predetermined amount of torque to suitably couple the transducer assembly with the waveguide mechanically and acoustically. Motor (350) is then deactivated, even as lever arm (360) continues to pivot toward body (322).

Figure 23D:
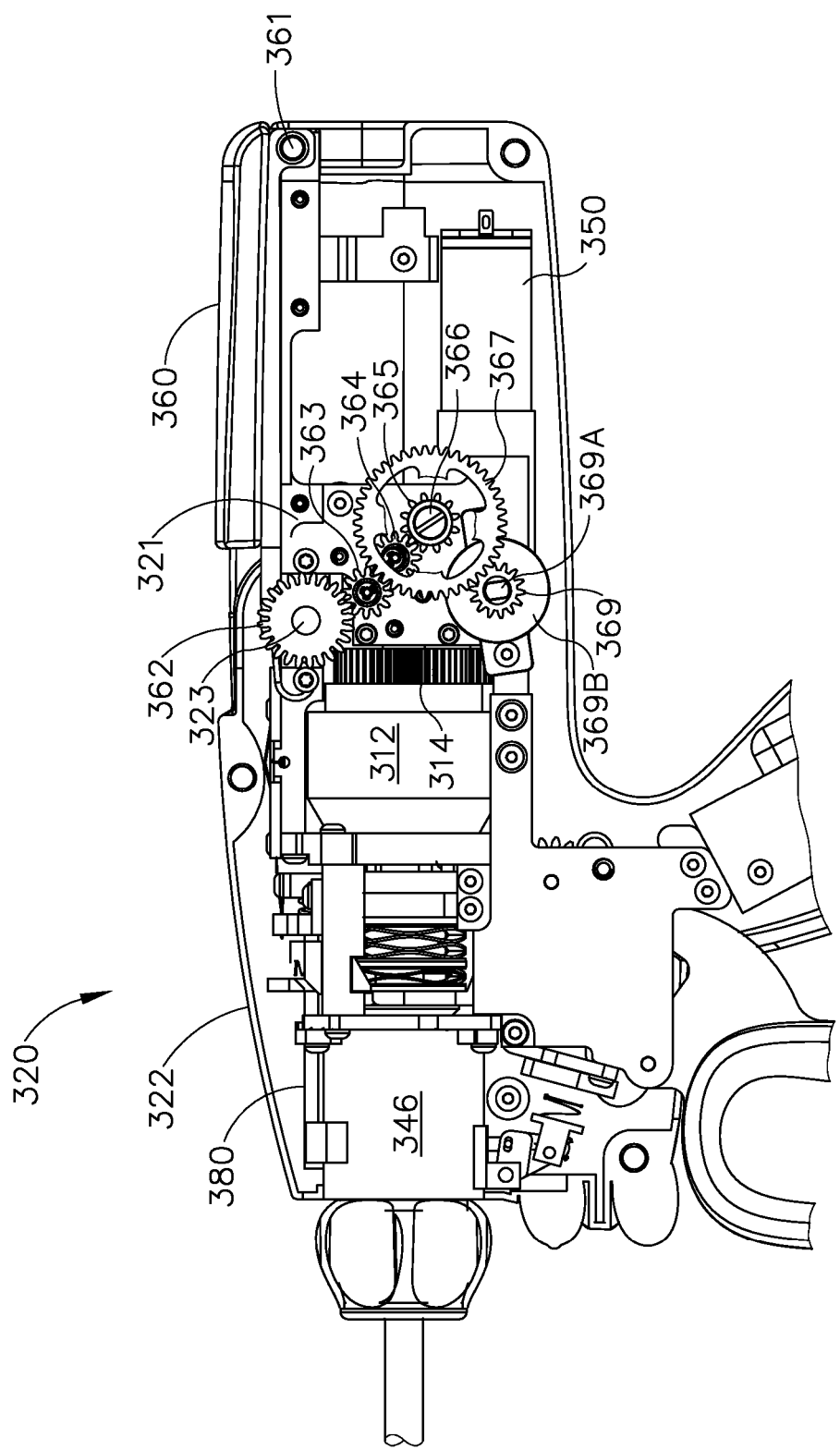
FIG. 23D depicts a side elevational view of the lever arm of the handle assembly of FIG. 16 moved into a fourth rotational position.
Figure 24B:
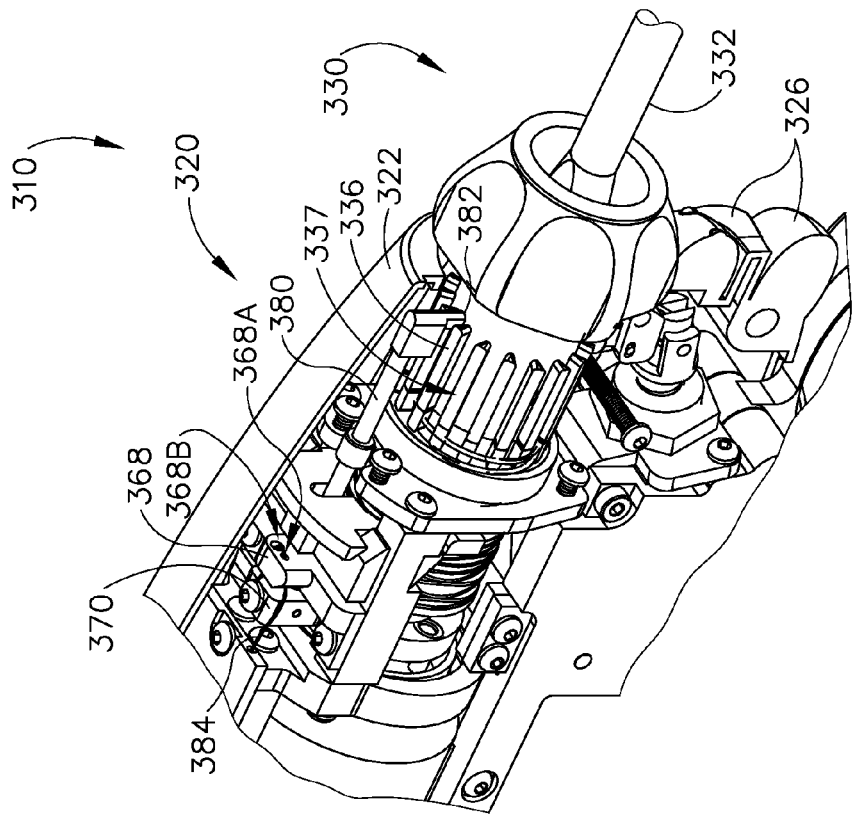
FIG. 24B depicts a perspective view of a locking mechanism of the handle assembly of FIG. 16 in a first longitudinal position correlating to the lever arm of the handle assembly in the third rotational position.
Figure 24A:
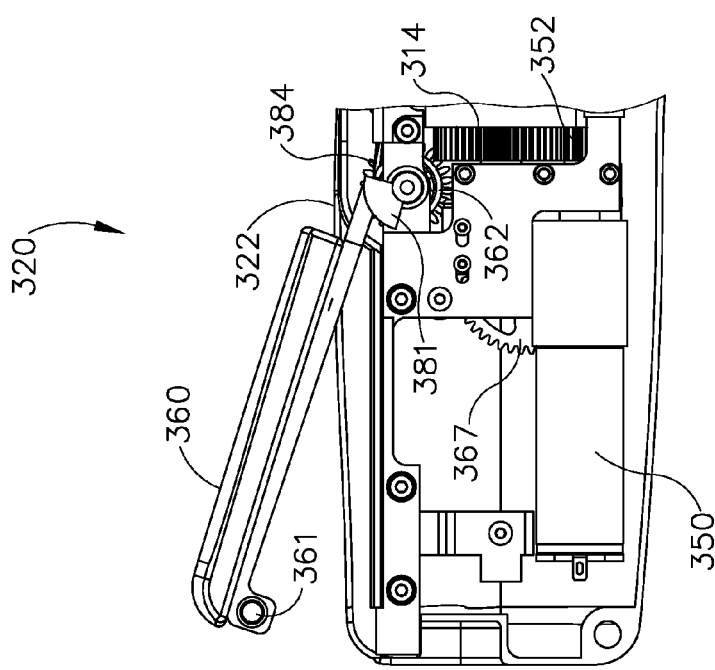
FIG. 24A depicts a side elevational view of the lever arm of the handle assembly of FIG. 16 in the third rotational position.

After reaching the stage shown in FIG. 23C, the operator continues to pivot lever arm (360) toward body (322) to the position shown in FIG. 23D. During this range of motion, cable (384) advances locking member (380) distally from the position shown in FIG. 24B to the position shown in FIG. 24D. This distal movement of locking member (280) disengages tab (382) from splines (336), thereby allowing shaft assembly (330) to rotate relative to handle assembly (320). It should be understood that tab (382) prevents shaft assembly (330) from rotating relative to handle assembly (320) during the stages shown in FIGS. 22A-22C, and up until lever arm (360) reaches the position shown in FIGS. 22D and 24C. It should also be understood that cable (384) retracts proximally during the stages shown in FIGS. 22A-22C, and up until lever arm (360) reaches the position shown in FIGS. 22D and 24C, yet cable (384) does not advance locking member (380) during this proximal movement of cable (384). Instead, cable (384) extends tensioning spring (365) during this proximal movement of cable (384). By the time lever arm (360) reaches the position shown in FIGS. 22D and 24C, tensioning spring (365) is fully extended and is no longer laterally deflecting cable (384), such that further proximal movement of cable (384) will provide the distal advancement of locking member (380).

After instrument (310) has reached the configuration shown in FIGS. 22D, 24C, and 24D, instrument (310) may be ready for operation. In the present example, the proximal end of lever arm (360) includes a resiliently biased ball detent feature (361) that is configured to engage a complementary recess formed in body (322) of handle assembly (320), to thereby assist in maintaining lever arm (360) in the position shown in FIGS. 22D and 24C. Of course, a variety of alternative features may be used in addition to or in lieu of ball detent feature (361).

Figure 55:
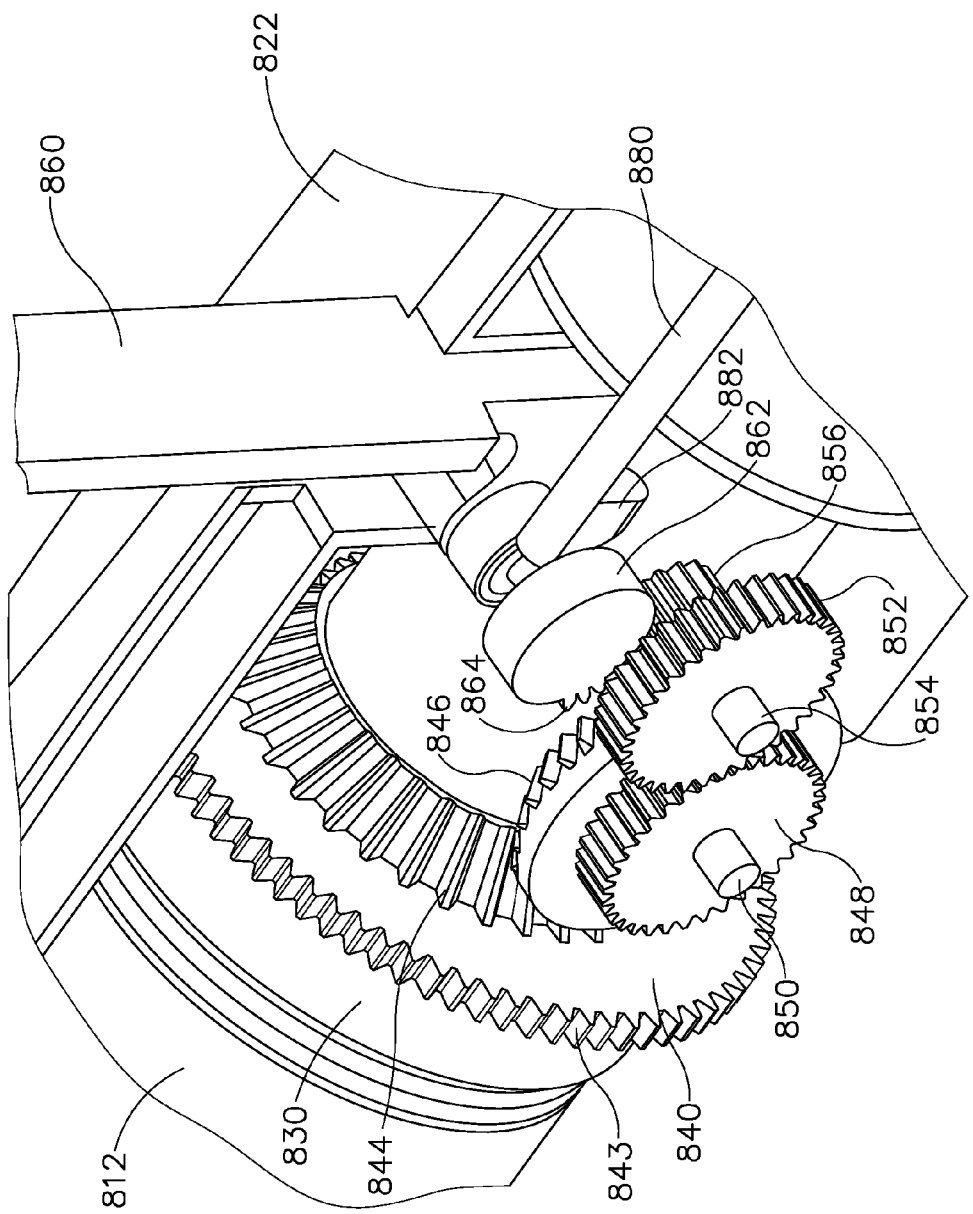
FIG. 55 depicts another perspective view of the assembly of FIG. 54.

FIGS. 54-56C show exemplary alternative features that may be incorporated into instrument (310) to couple a transducer with an acoustic waveguide. In particular, FIGS. 54-55 show a transducer housing (812), which is rotatably supported within a body (822) of a handle assembly. An ultrasonic transducer assembly is secured within transducer housing (812), such that the ultrasonic transducer assembly rotates with transducer housing (812) relative to body (822). A clutch ring (830) is fixedly secured to the exterior of body (822) and is coaxially disposed in relation to the ultrasonic transducer assembly. Clutch ring (830) includes a set of obliquely angled, distally facing teeth (830). Teeth (830) are engaged with obliquely angled, proximally facing teeth (842) of a clutch drive gear (840), which is also coaxially aligned with the ultrasonic transducer assembly. Clutch drive gear (840) is resiliently biased in the proximal direction, such that teeth (842) are biased into engagement with teeth (832). As will be described in greater detail below, clutch drive gear (840) is operable to drive clutch ring (830) and transducer housing (812) in a first rotational direction until a certain torque threshold is reached, at which point teeth (842) begin to slip against teeth (832) such that clutch drive gear (840) no longer drives clutch ring (830) and transducer housing (812) in the first rotational direction after the certain torque threshold is reached. However, clutch drive gear (840) is operable to drive clutch ring (830) and transducer housing (812) in a second rotational direction regardless of the torque.

Clutch drive gear (840) includes an angularly spaced array of outwardly extending teeth (843). Teeth (843) are configured to mesh with a gear (not shown) of a drive shaft (not shown) of a motor (not shown). The motor may thus be operable to drive rotation of clutch drive gear (840), thereby driving rotation of clutch ring (830) and transducer housing (812) within body (822). By way of example only, teeth (843) may mesh with a gear like drive gear (352) described above, which is secured to drive shaft (351) of motor (350). Other suitable arrangements will be apparent to those of ordinary skill in the art in view of the teachings herein.

A lever arm (860) is pivotally coupled with body (822). Lever arm (860) includes an integral sector gear (832) that rotates relative to body (822) as lever arm (860) pivots relative to body (822). Sector gear (832) includes a set of teeth (864) extending along only a portion of an angular range of the circumferential perimeter of sector gear (832). As will be described in greater detail below, these teeth (864) are positioned to mesh with complementary teeth of a gear (856) as lever arm (860) is pivoted through a certain range of motion relative to body (822). Gear (856) is unitarily coupled with another gear (852) along a pin (854), which is rotatably supported in body (822). Gear (852) meshes with another gear (848), which is unitarily coupled with a bevel gear (846) along a pin (850). Pin (850) is also rotatably supported in body (822). As best seen in FIG. 55, bevel gear (846) is engaged with another bevel gear (844), which is integrally disposed on the distal face of clutch drive gear (840). It should be understood from the foregoing that, as lever arm (860) is pivoted relative to body (822) through the range of motion where teeth (864) engage gear (856), the drivetrain formed by gears (862, 856, 852, 848, 846, 844) will rotate clutch drive gear (840) in body (822), thereby rotating clutch ring (830) and transducer housing (812) within body (822).

Figure 56A:
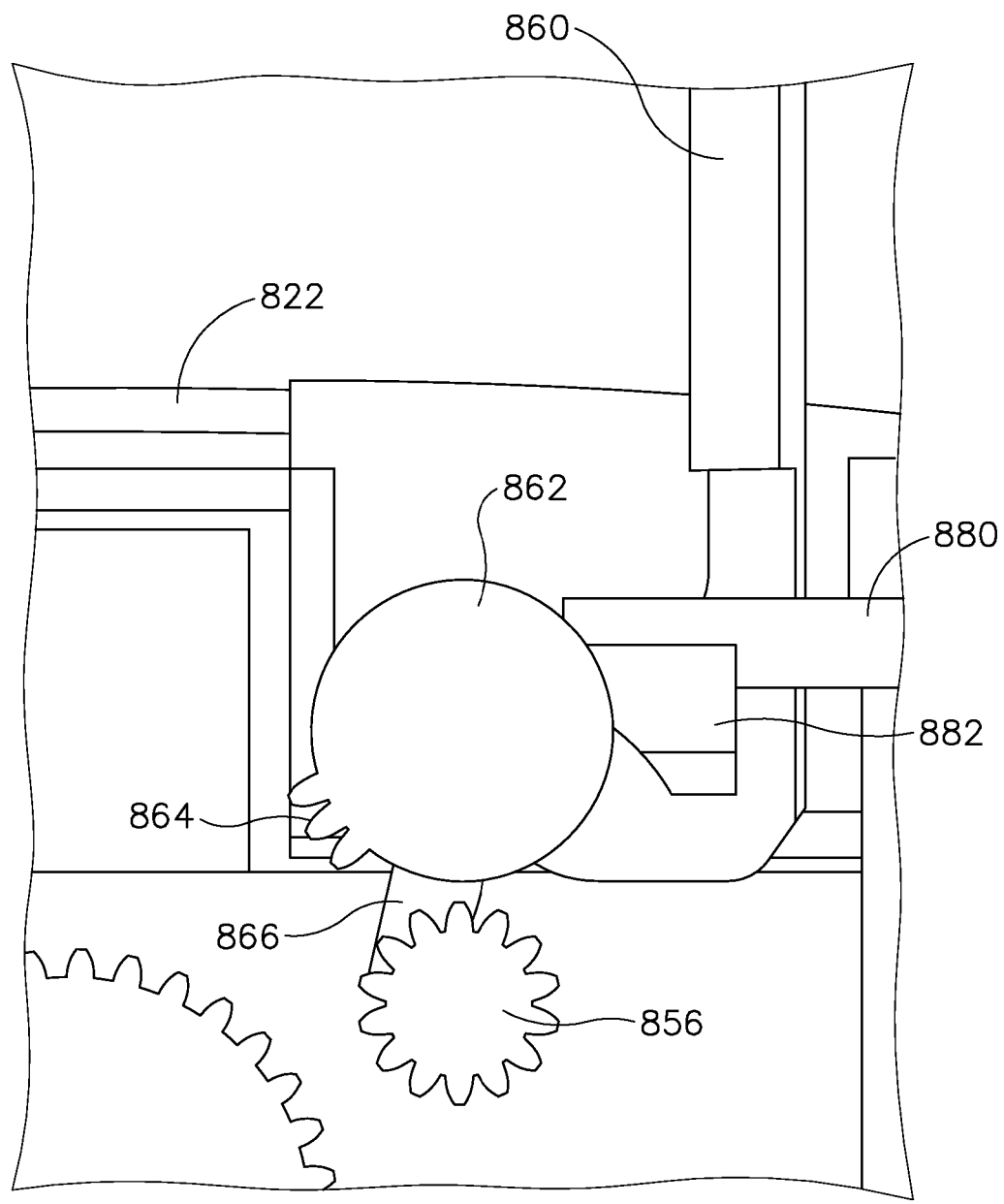
FIG. 56A depicts a side elevational view of a lever, sector gear, and driven gear of the assembly of FIG. 54, in a first configuration.
Figure 56B:
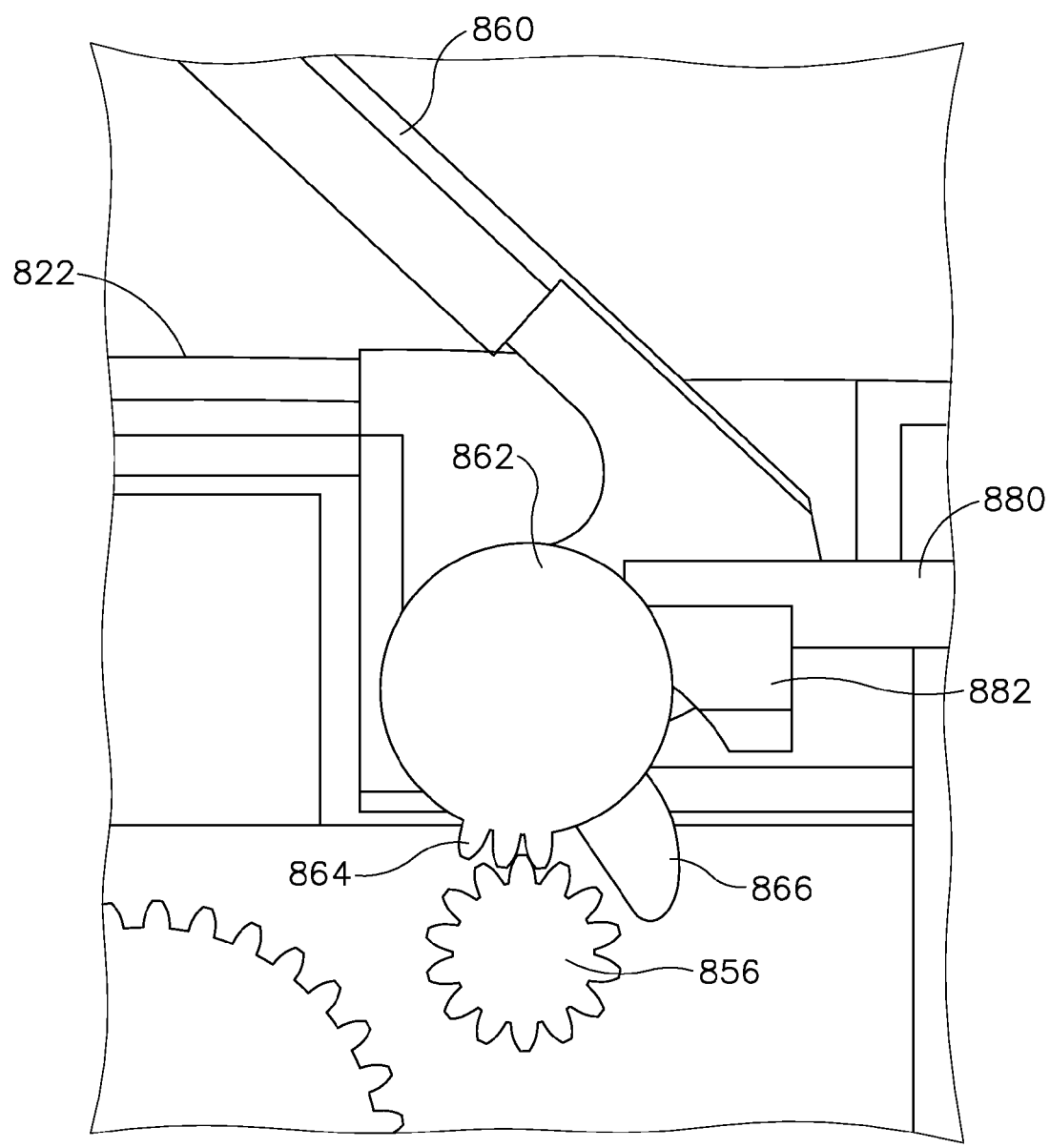
FIG. 56B depicts a side elevational view of the lever, sector gear, and driven gear of the assembly of FIG. 54, in a second configuration.
Figure 56C:
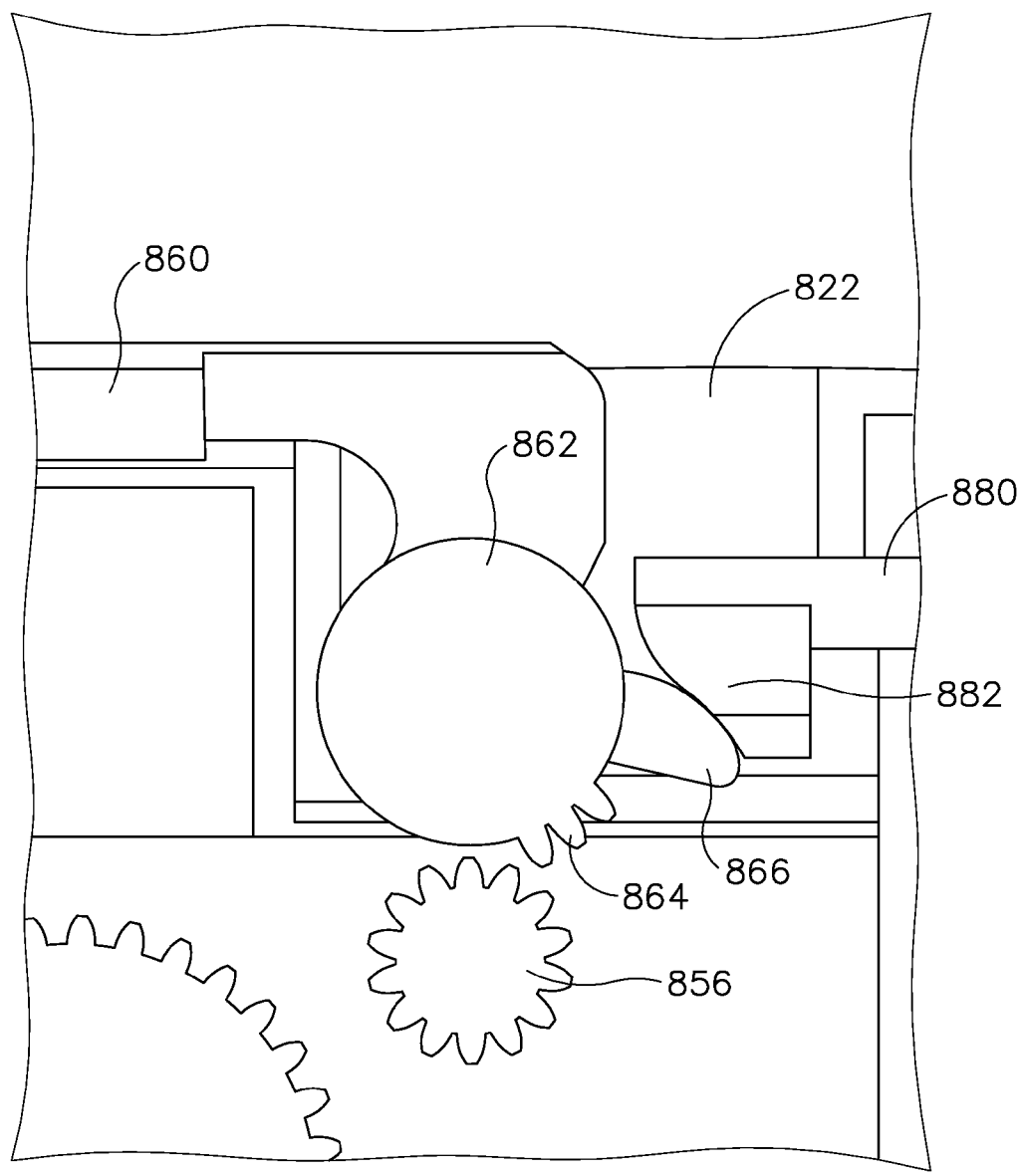
FIG. 56C depicts a side elevational view of the lever, sector gear, and driven gear of the assembly of FIG. 54, in a third configuration.

A locking member (880) is slidably disposed in body (822), such that locking member (880) is configured to translate longitudinally within body (822). The proximal end of locking member (880) includes a downwardly extending integral cam feature (882). The distal end of locking member is configured to selectively engage features of a shaft assembly, to thereby selectively lock the rotational position of the shaft assembly relative to body (822). By way of example only, the distal end of locking member may include a feature similar to tab (382) as described above, which may be configured to engage splines of a shaft assembly similar to splines (336) as also described above. As best seen in FIGS. 56A-56C, lever arm (860) includes an integral cam feature (866) that is configured to rotate about the same axis as lever arm (860) and sector gear (862) as lever arm (860) is pivoted relative to body (822). As will be described in greater detail below, cam feature (866) of lever arm (860) is configured to engage cam feature (882) of locking member (880), thereby driving locking member (880) distally relative to body (822), as lever arm (860) is pivoted through a certain range of motion relative to body (822).

FIGS. 56A-56B depict exemplary stages of operation. In particular, FIG. 56A depicts lever arm (860) in an initial pivotal position. At this stage, the proximal end of a shaft assembly may be inserted into the distal end of body (822). Locking member (880) is in a proximal position, where the distal end of locking member (880) prevents rotation of the shaft assembly relative to body (822). It should be understood that locking member (880) may be resiliently biased to the proximal position by a coil spring, leaf spring, and/or some other resilient feature. The operator then pivots lever arm (860) from the position shown in FIG. 56A toward the position shown in FIG. 56B. During this transition, a sensor (e.g., encoder, etc.) senses the pivotal movement of lever arm (860) and activates the motor to rotate clutch drive gear (840) in body (822), thereby rotating clutch ring (830) and transducer housing (812) within body (822). This provides an initial threading of the threaded stud of the ultrasonic transducer into the proximal threaded recess of an acoustic waveguide as described elsewhere herein. It should be understood that, during the initial stages of the transition from the configuration shown in FIG. 56A to the configuration shown in FIG. 56B, sector gear (862) does not engage gear (856). Clutch ring (830) and transducer housing (812) are thus driven solely by the motor during the initial stages of the transition from the configuration shown in FIG. 56A to the configuration shown in FIG. 56B.

As shown in FIG. 56B, as lever arm (860) is pivoted relative to body (822), sector gear (862) eventually reaches a position where teeth (864) engage gear (856). In the present example, once lever arm (860) reaches the angular position where teeth (864) engage gear (856), the sensor that senses the pivotal movement of lever arm (860) detects this angular position and triggers the deactivation of the motor. The motor is thus deactivated when teeth (864) engage gear (856). As the operator continues to pivot lever arm (860) relative to body (822), the drivetrain formed by gears (862, 856, 852, 848, 846, 844) will rotate clutch drive gear (840) in body (822), thereby rotating clutch ring (830) and transducer housing (812) within body (822). It should therefore be understood that the motor provides an initial, electrically powered coupling of the transducer assembly with the waveguide; while lever arm (860) provides a final, manually powered coupling of the transducer assembly with the waveguide. Once a suitable level of torque is achieved at the coupling of the transducer assembly with the waveguide, teeth (842) begin to slip against teeth (832) such that clutch drive gear (840) no longer drives clutch ring (830) and transducer housing (812). In other words, clutch drive gear (840) and clutch ring (830) cooperate to prevent the transducer assembly from being over-torqued with respect to the waveguide.

After the transducer assembly has been suitably coupled with the acoustic waveguide, the operator may continue to pivot lever arm (860) relative to body (822), to the position shown in FIG. 56C. Upon reaching this stage, cam feature (866) of lever arm (860) has engaged cam feature (882) of locking member (880), driving locking member (880) distally relative to body (822). This distal movement of locking member (880) disengages the distal end of locking member (880) from the shaft assembly, thereby enabling the shaft assembly to rotate relative to body (822). Also at this stage, teeth (864) of sector gear (862) have cleared gear (856). If the operator wishes to thereafter rotate the shaft assembly and transducer housing (812) within body (822) (e.g., to reposition an end effector at the distal end of the shaft assembly, etc.), the shaft assembly and transducer housing (812) may be free to rotate within body (822). Gears (856, 852, 848, 846, 844) may simply rotate freely within body (822).

In another merely illustrative variation, the ratcheting clutch provided by teeth (832, 842) is replaced with an assembly formed by a one-way bearing and a smooth clutch plate. Other suitable variations of instrument (310) will be apparent to those of ordinary skill in the art in view of the teachings herein.

Figure 25:
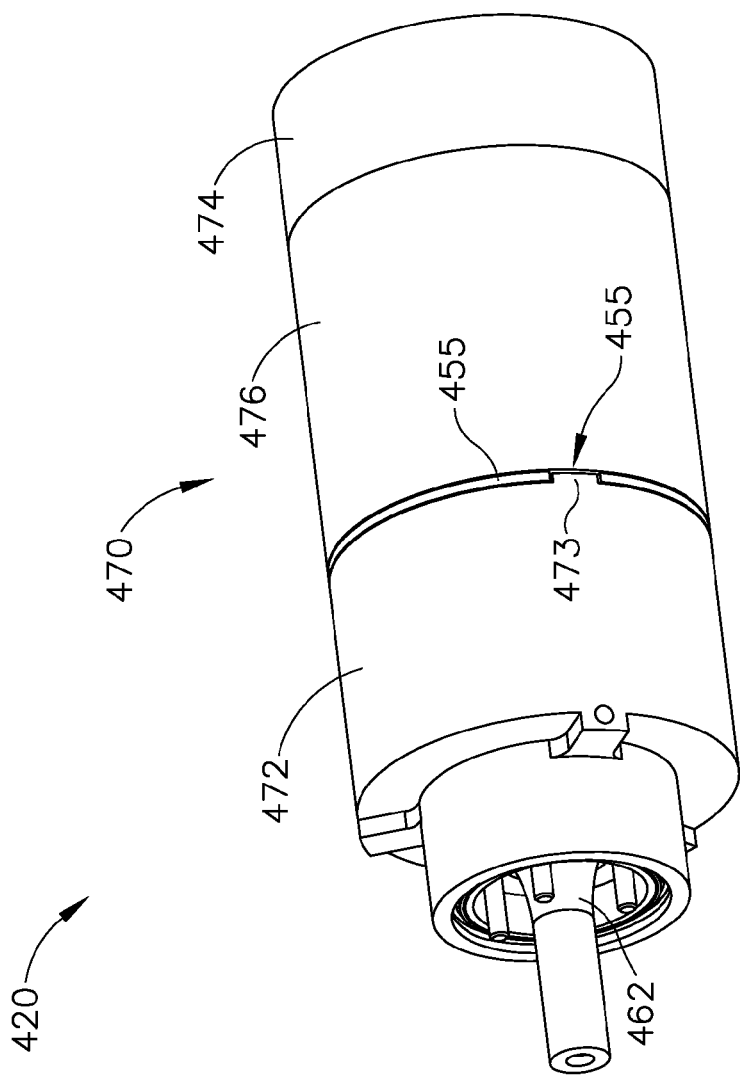
FIG. 25 depicts a perspective view of an exemplary motor and ultrasonic transducer assembly.
Figure 26:
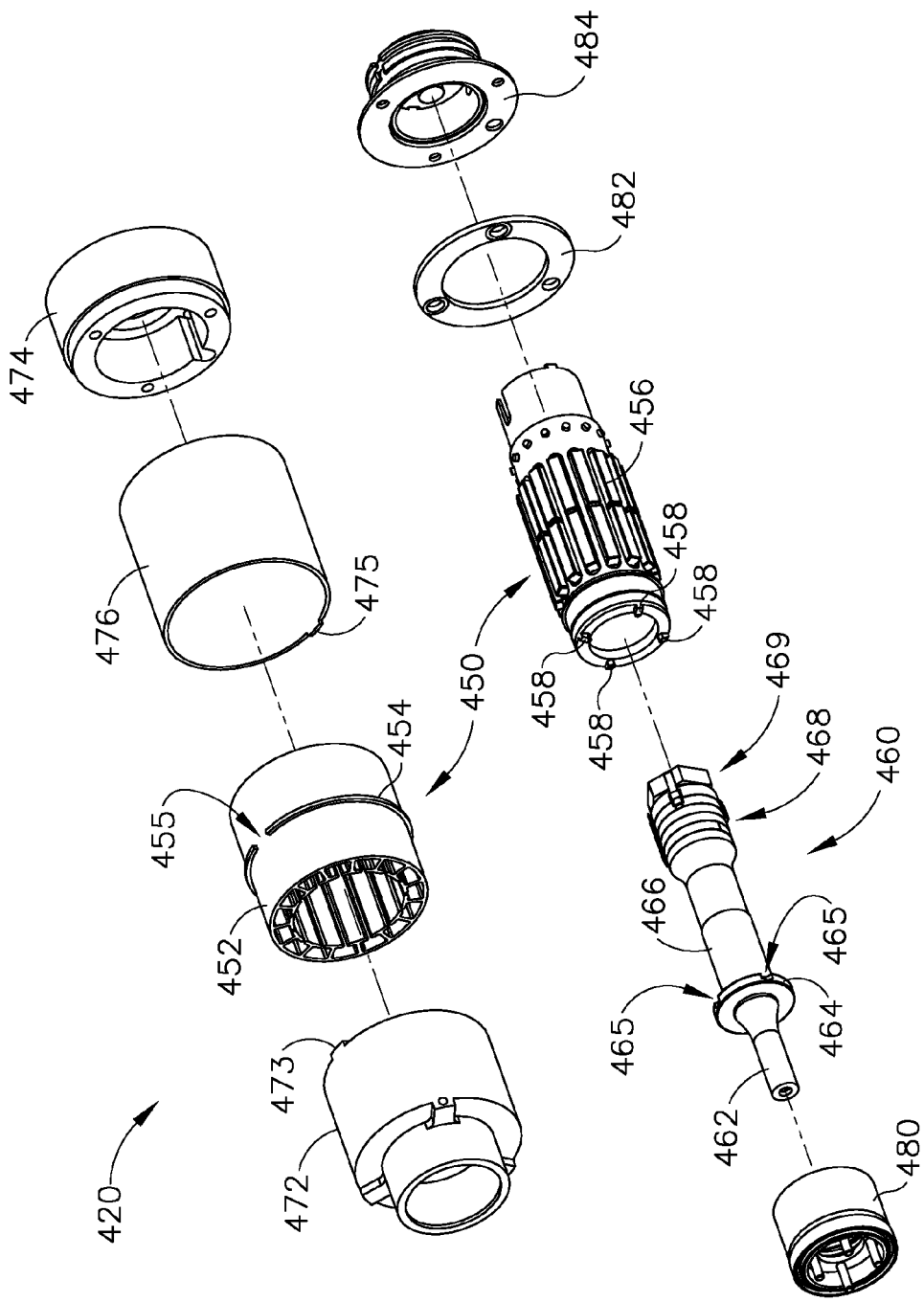
FIG. 26 depicts an exploded perspective view of the assembly of FIG. 25.
Figure 27:
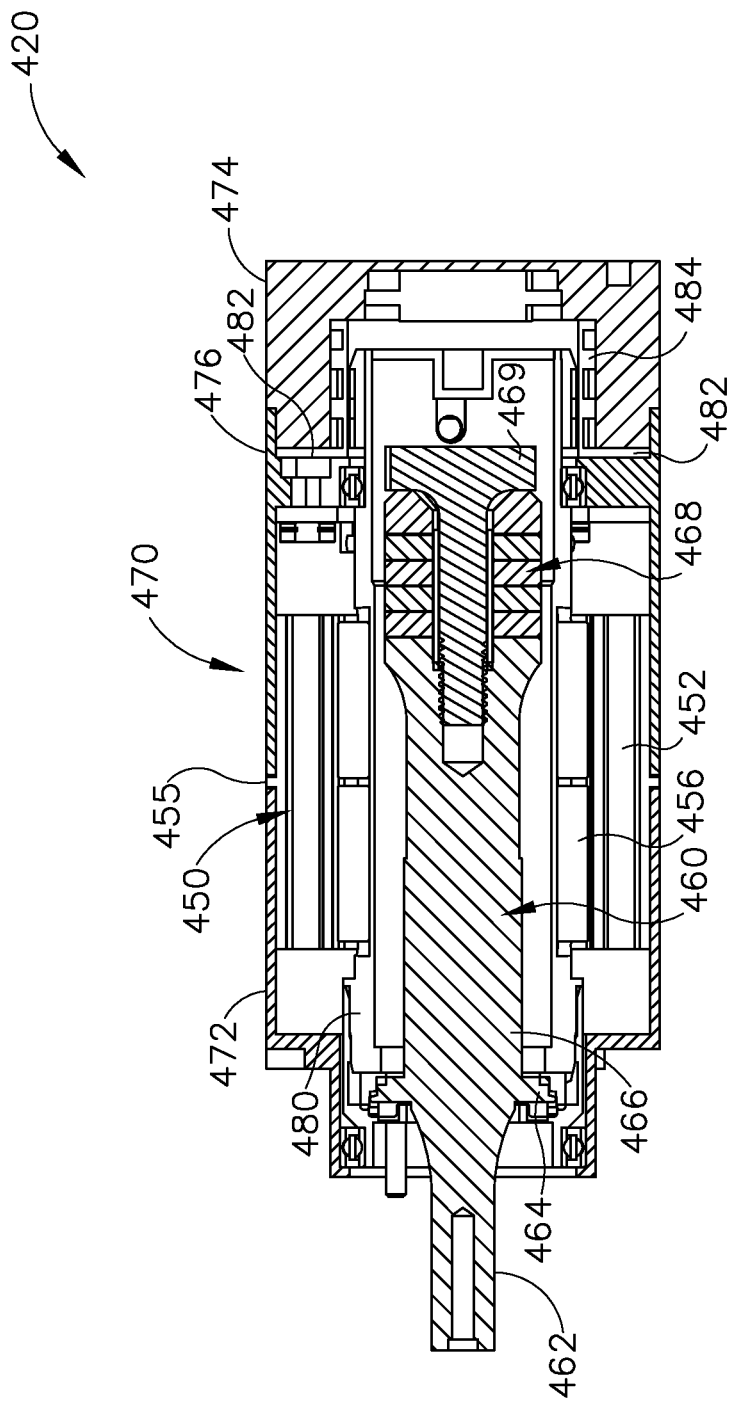
FIG. 27 depicts a cross-sectional view of the assembly of FIG. 25.

C. Exemplary Ultrasonic Surgical Instrument with Coupling Via Integral Coaxial Motor In some versions of instrument (10) discussed above, it may be desirable to provide a version of transducer assembly (12) that has an integral motor. FIGS. 25-27 show an exemplary assembly (420) that integrates a motor (450) and an ultrasonic transducer (460) in a coaxial relationship. Assembly (420) may be readily incorporated into instrument (10), to provide a motorized coupling between a transducer and a waveguide. Motor (450) of the present example comprises a stator (452) and a rotor (456). Stator (452) includes a flange (454) that defines diametrically opposing gaps (455) (only one gap (455) is shown in FIG. 26). Rotor (456) is coaxially and rotatably disposed within stator (452).

In some versions, motor (450) is a brushless motor. By way of example only, stator (452) may include windings that are selectively commutated while rotor (456) includes an angularly spaced array of permanent magnets, such that electromagnetic forces urge rotor (456) to rotate within stator (452) as the windings of stator (452) are selectively commutated. Other suitable components, features, and configurations that may be provided for stator (452) and rotor (456) will be apparent to those of ordinary skill in the art in view of the teachings herein.

Ultrasonic transducer (460) is secured within rotor (456). As shown in FIG. 26, ultrasonic transducer (460) of the present example comprises a horn (462), a mounting flange (464), a body (466), a stack of piezoelectric discs (468), and a bolt (469) that longitudinally compresses discs (468) against body (466). The compressed discs (468) are operable to convert electrical power into ultrasonic vibrations, which are communicated through body (466) to horn (462). Horn (462) may include a threaded stud or other coupling feature to mechanically and acoustically couple transducer (460) with a waveguide as described above. Flange (464) is located at a position corresponding to a node associated with ultrasonic vibrations generated by transducer (460).

Motor (450) and transducer assembly (460) are disposed within an external housing (470). Housing (470) comprises a distal portion (472), a proximal portion (474), and an intermediate portion (476) which together define canister-like shroud. As best seen in FIG. 26, a proximal face of distal portion (472) includes a proximally extending tab (473). A distal face of intermediate portion (476) includes a distally extending tab (475). Tabs (473, 475) engage respective gaps (455) in flange (454) of stator (452), such that housing (470) and stator (452) are both rotationally secured relative to each other. It should also be understood that housing (470) may be rotationally secured within the body of a handle assembly or other kind of body.

Transducer (460) is secured to rotor (456) via flange (464). In particular, the distal face of rotor (456) includes an angular array of distally facing projections (458) that are configured to fit in complementary recesses (465) that are formed in the proximal face of flange (464). Thus, with projections (458) disposed in recesses (465), transducer (460) and rotor (456) rotate together. Rotor (456) is further secured to a bushing (480), which provides a rotatable support between rotor (456) and stator (452). In particular, bushing (480) is positioned in distal portion (472) of housing (470) and thereby provides structural support to rotor (456) and transducer (460) while also permitting rotor (456) and transducer (460) to rotate within distal portion (472) of housing (470). An intermediate mounting feature (482) is disposed about rotor (456) and within intermediate portion (476) of housing. Intermediate mounting feature (482) provides support to rotor (456) and transducer (460) while also permitting rotor (456) and transducer to rotate within intermediate portion (476) of housing (470). A proximal mounting feature (484) is disposed about rotor (456) and within proximal portion (474) of housing. Intermediate mounting feature (482) provides support to rotor (456) and transducer (460) while also permitting rotor (456) and transducer to rotate within proximal portion (474) of housing (470).

In view of the foregoing, it should be understood that motor (450) may be activated to rotate transducer (460) relative to the body of a handle assembly or other kind of body. Motor (450) may thus be activated to rotatably drive a threaded stud extending distally from horn (462) into a threaded recess of a waveguide. Motor (450) may also be activated in reverse to decouple the waveguide from horn (462). Various suitable ways in which assembly (420) may be integrated into instrument (10) and variations thereof will be apparent to those of ordinary skill in the art in view of the teachings herein.

D. Exemplary Ultrasonic Surgical Instrument with Coupling Via Integral Coaxial Motor and Gear Assembly In some versions of instrument (10) discussed above, it may be desirable to provide a gear assembly in addition to a version of transducer assembly (12) that has an integral motor. By way of example only, the addition of a gear assembly may enable selected gear ratios that provide a desired balance between motor size, power consumption, and torque. A gear assembly may also compound the relative rotation between a rotor and stator of a motor. FIGS. 28-37 show an exemplary assembly (500) that integrates a motor (550) with an ultrasonic transducer (560) and a set of gears (510). Assembly (500) may be readily incorporated into instrument (10), to provide a motorized coupling between a transducer and a waveguide. Motor (550) of the present example comprises a stator (570) and a rotor (576). Rotor (576) is coaxially and rotatably disposed within stator (570). In some versions, motor (550) is a brushless motor. By way of example only, stator (570) may include windings that are selectively commutated while rotor (576) includes an angularly spaced array of permanent magnets, such that electromagnetic forces urge rotor (576) to rotate within stator (570) as the windings of stator (570) are selectively commutated. Other suitable components, features, and configurations that may be provided for stator (570) and rotor (576) will be apparent to those of ordinary skill in the art in view of the teachings herein.

Figure 29:
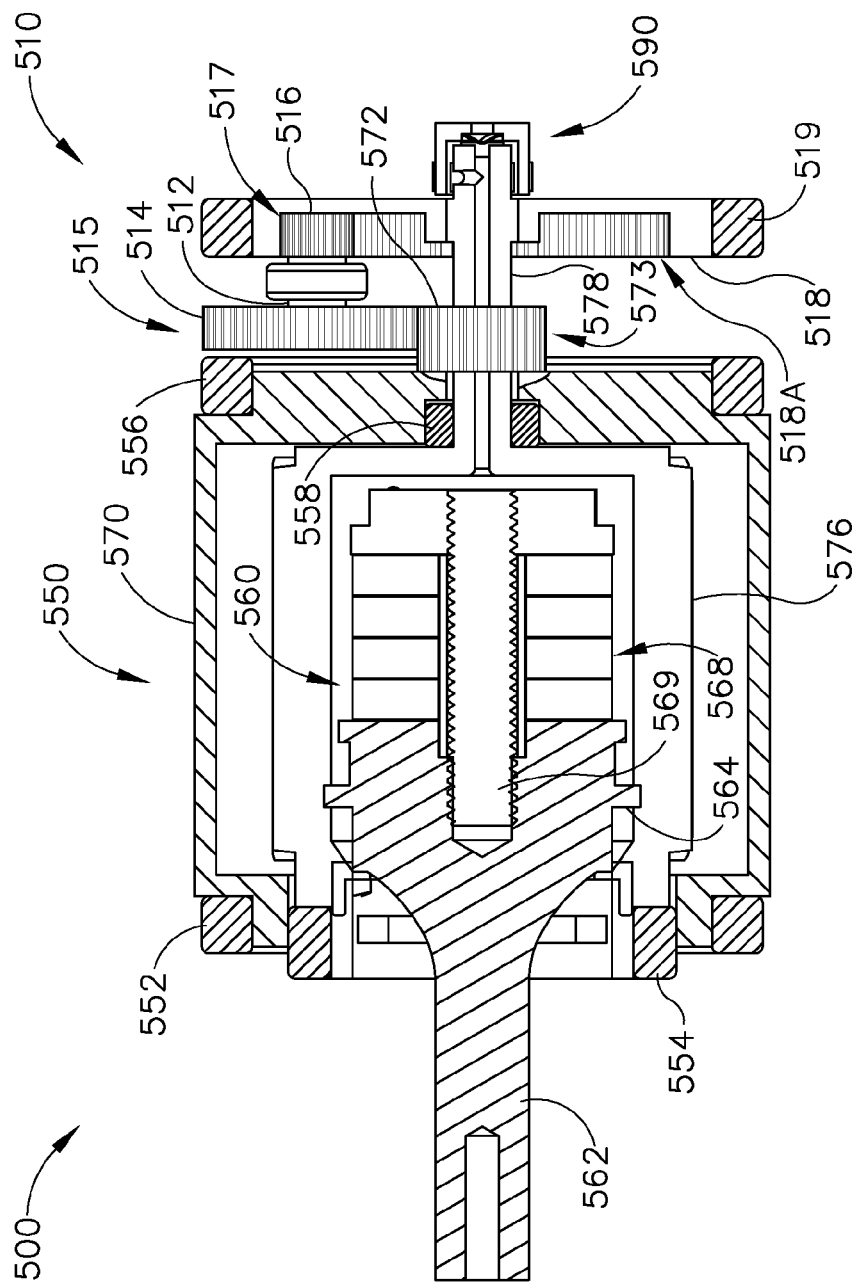
FIG. 29 depicts a cross-sectional view of the assembly of FIG. 28, taken along line 29-29 of FIG. 30.
Figure 34:
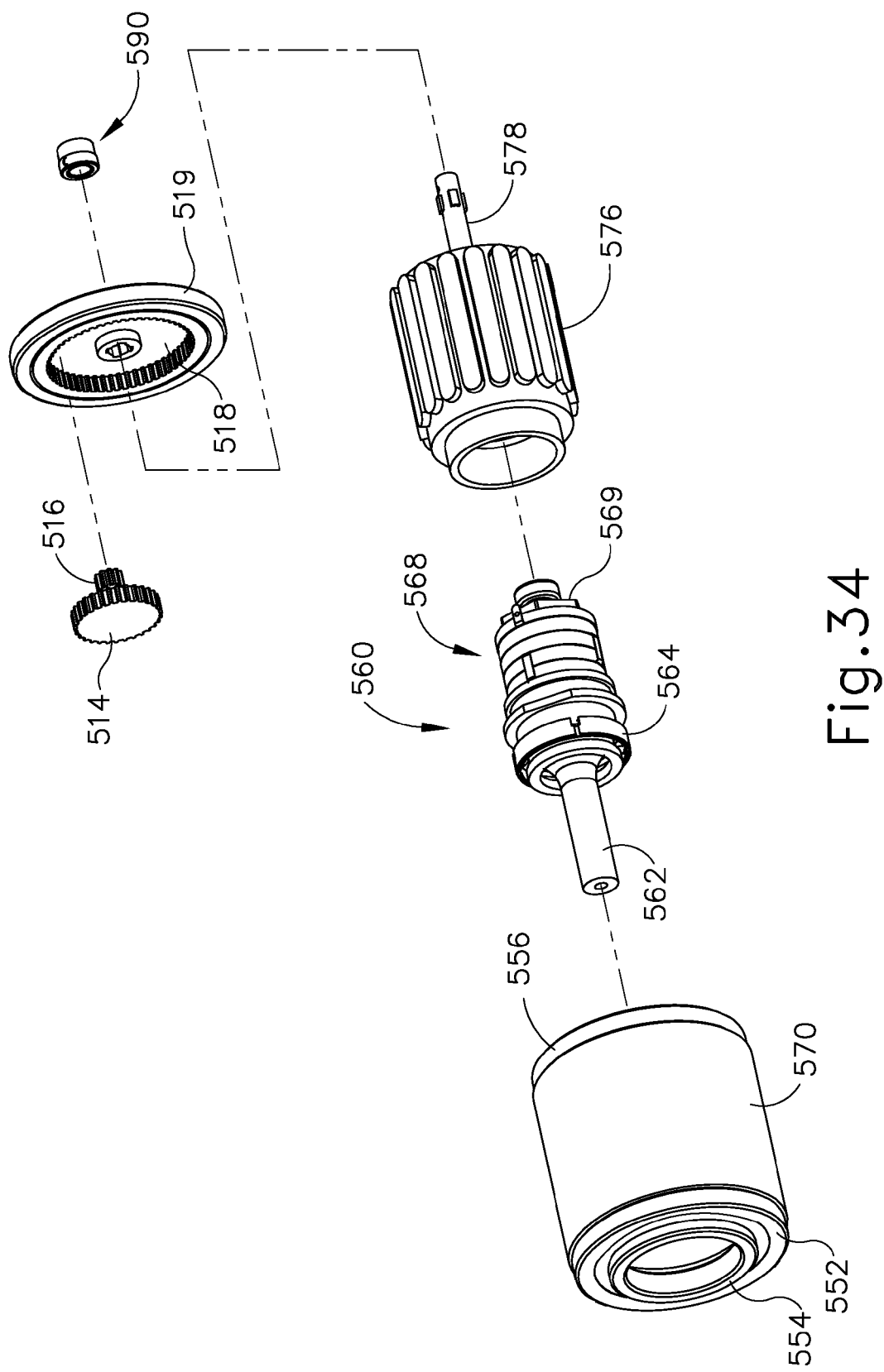
FIG. 34 depicts an exploded view of the assembly of FIG. 28.

Ultrasonic transducer (560) is secured within rotor (576). As shown in FIGS. 29 and 34, ultrasonic transducer (560) of the present example comprises a horn (562), a mounting flange (564), a stack of piezoelectric discs (568), and a bolt (569) that longitudinally compresses discs (568). The compressed discs (568) are operable to convert electrical power into ultrasonic vibrations, which are communicated through horn (562). Horn (562) may include a threaded stud or other coupling feature to mechanically and acoustically couple transducer (560) with a waveguide as described above. Flange (564) is located at a position corresponding to a node associated with ultrasonic vibrations generated by transducer (560). Transducer (560) is secured to an interior portion of rotor (576) via flange (564), such that transducer (560) and rotor (576) rotate together. Rotor (576) is rotatably supported within stator (570) by a bushing (558), as best seen in FIG. 29. Rotor (576) is also rotatably supported within the body of a handle assembly or some other instrument body by a distal bushing (554). Stator (570) is rotatably supported within the body of a handle assembly or some other instrument body by a pair of bushings (552, 556). Thus, stator (570) and rotor (576) may both rotate within the body of a handle assembly or some other instrument body.

Figure 28:
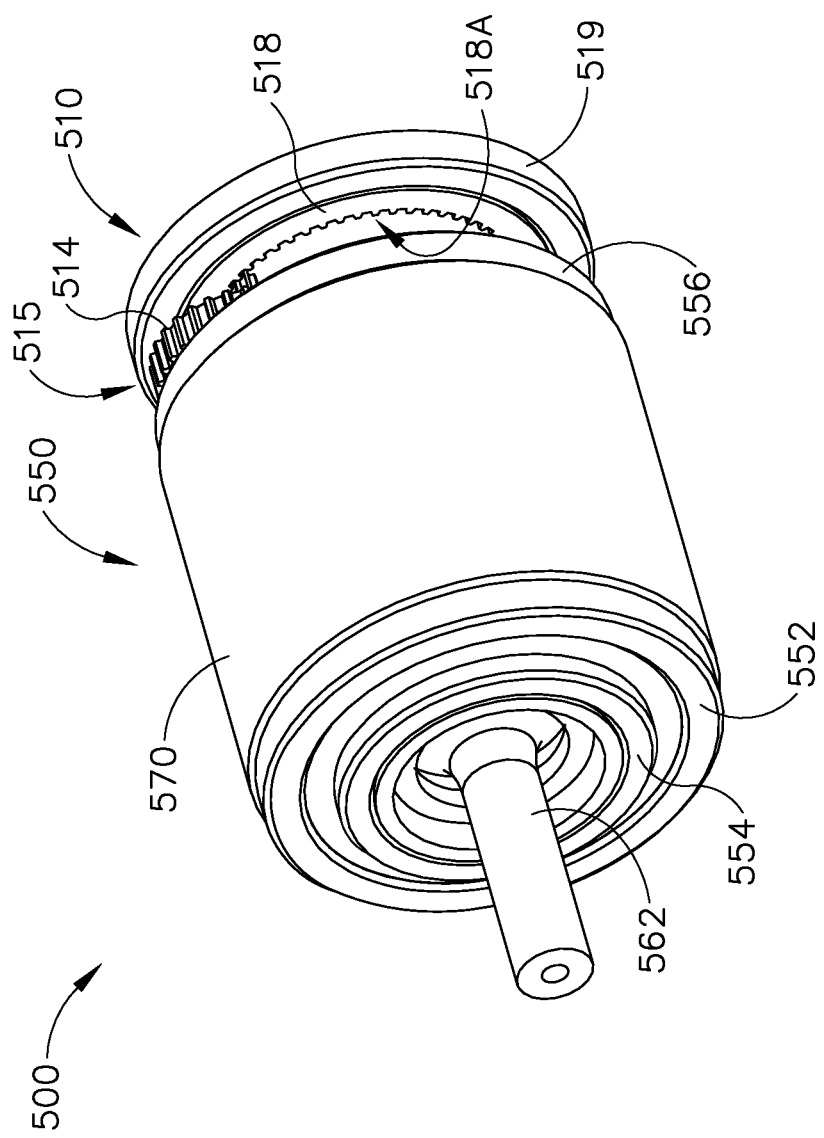
FIG. 28 depicts a perspective view of an exemplary motor, gear, and transducer assembly.
Figure 30:
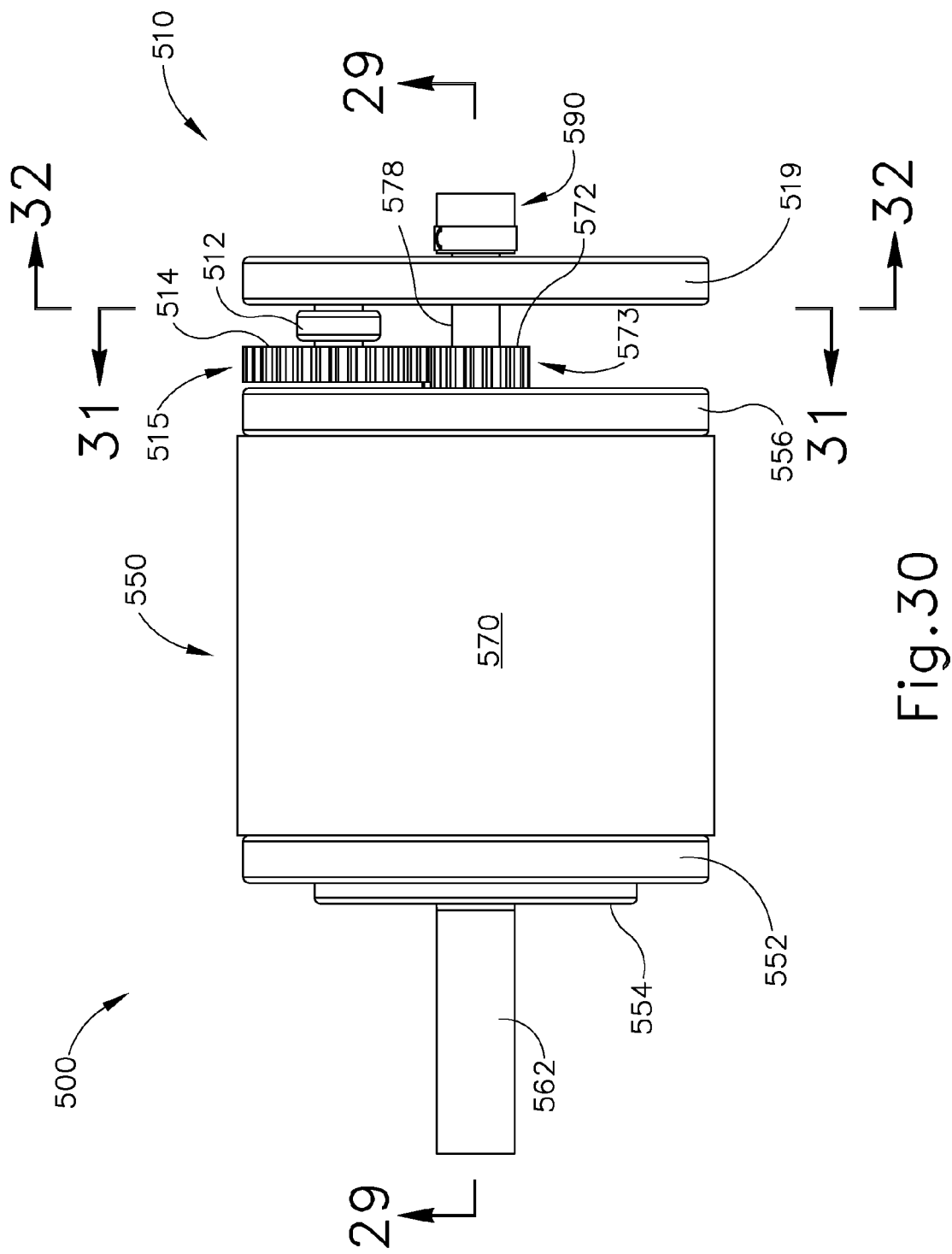
FIG. 30 depicts a side elevational view of the assembly of FIG. 28.

As best seen in FIGS. 29 and 34, rotor (576) includes a stem (578) that extends proximally from rotor (576) through stator (570). Stem (578) provides a passageway for wires (not shown) that are electrically coupled with piezoelectric discs (568) of transducer (560), such that stem (578) serves as a pathway for electrical power delivery to piezoelectric discs (568) as will be described in greater detail below. As best seen in FIGS. 28-30, horn (562) protrudes distally from stator (570), enabling horn (562) to be coupled with a waveguide as described herein.

Figure 31:
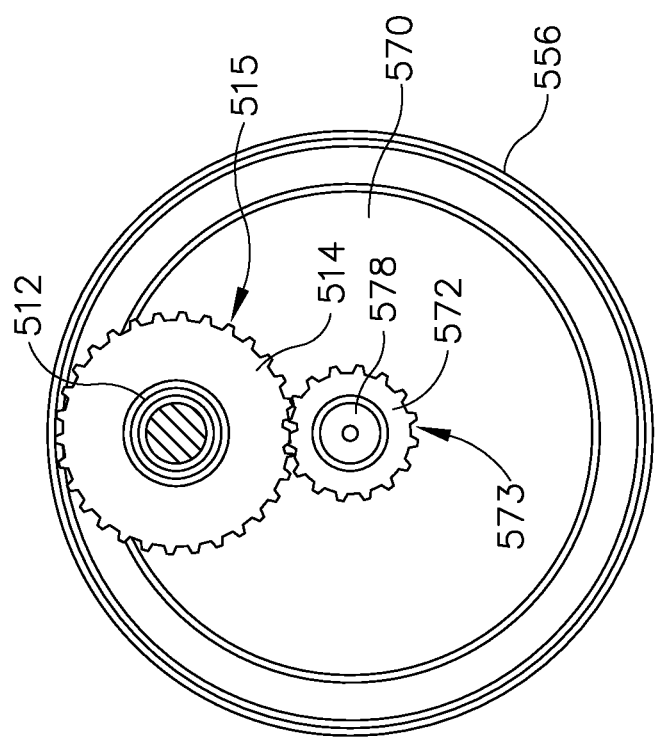
FIG. 31 depicts a cross-sectional view of the assembly FIG. 28, taken along line 31-31 of FIG. 30.
Figure 32:
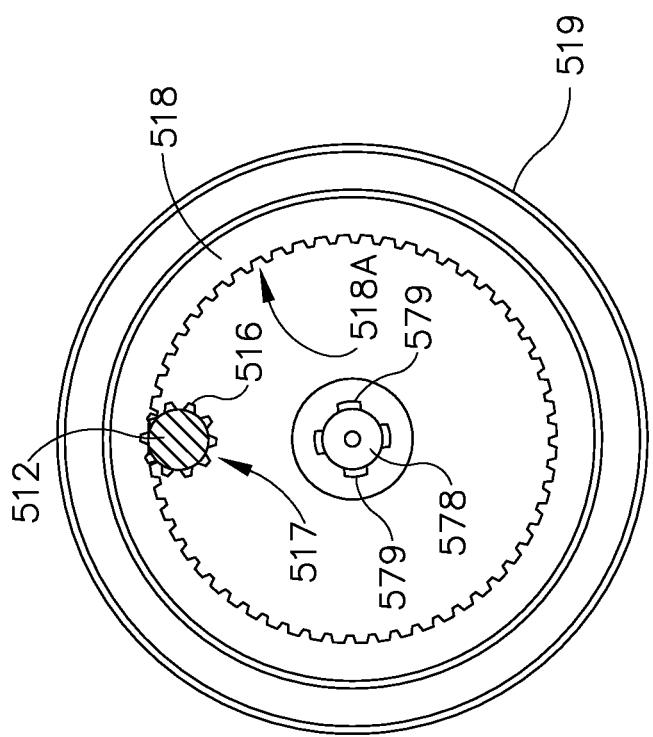
FIG. 32 depicts a cross-sectional view of the assembly of FIG. 28, taken along line 32-32 of FIG. 30.
Figure 33:
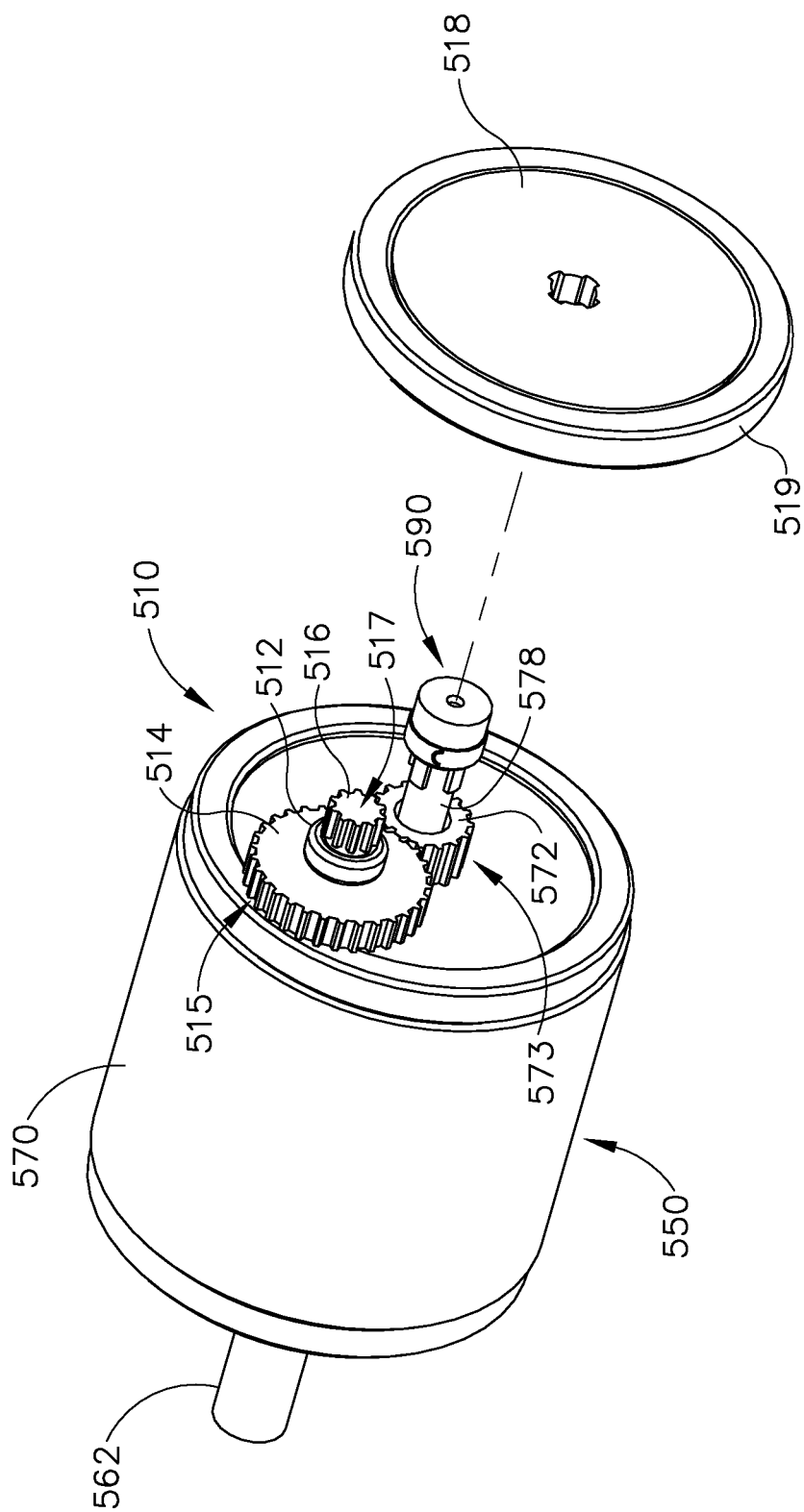
FIG. 33 depicts a partial exploded perspective view of the assembly of FIG. 28.

As best seen in FIGS. 29-31, the proximal face of stator (570) includes an integral gear (572). Stem (578) passes through a bore formed through the axis of gear (572). Gear (572) has external teeth (573) that mesh with external teeth (515) of another gear (515). Gear (515) is secured to an axle (512) with another gear (516). Gear (516) has external teeth (517) that mesh with external teeth (518A) of a ring gear (518). Ring gear (518) is rotatably supported by a bushing (519), which may be secured to the body of a handle assembly or some other instrument body. Ring gear (518) is fixedly secured to stem (578). Thus, when rotor (576) rotates when motor (550) is activated, ring gear (518) rotates unitarily with rotor (576) due to the coupling via stem (578). Rotation of ring gear (518) in a first direction causes rotation of gear (516) in the first direction, due to meshing of teeth (518A, 517). Rotation of gear (516) in the first direction causes rotation of gear (514) in the first direction, due to gears (514, 516) being secured to the same axle (512). Rotation of gear (514) in the first direction causes rotation of gear (572) in a second direction, due to meshing of teeth (515, 573). Rotation of gear (572) in the second direction causes rotation of stator (570) in the second direction, due to the unitary construction of stator (570) and gear (572). It should therefore be understood that activation of motor (550) to rotate rotor (576) in a first direction will also cause stator (570) to rotate in a second direction, due to mechanical communication provided through gear assembly (510). In other words, gear assembly (510) may compound the relative rotation between stator (570) and rotor (576). In some versions, gear assembly (510) provides a gear ratio of 13:1.

Figure 35:
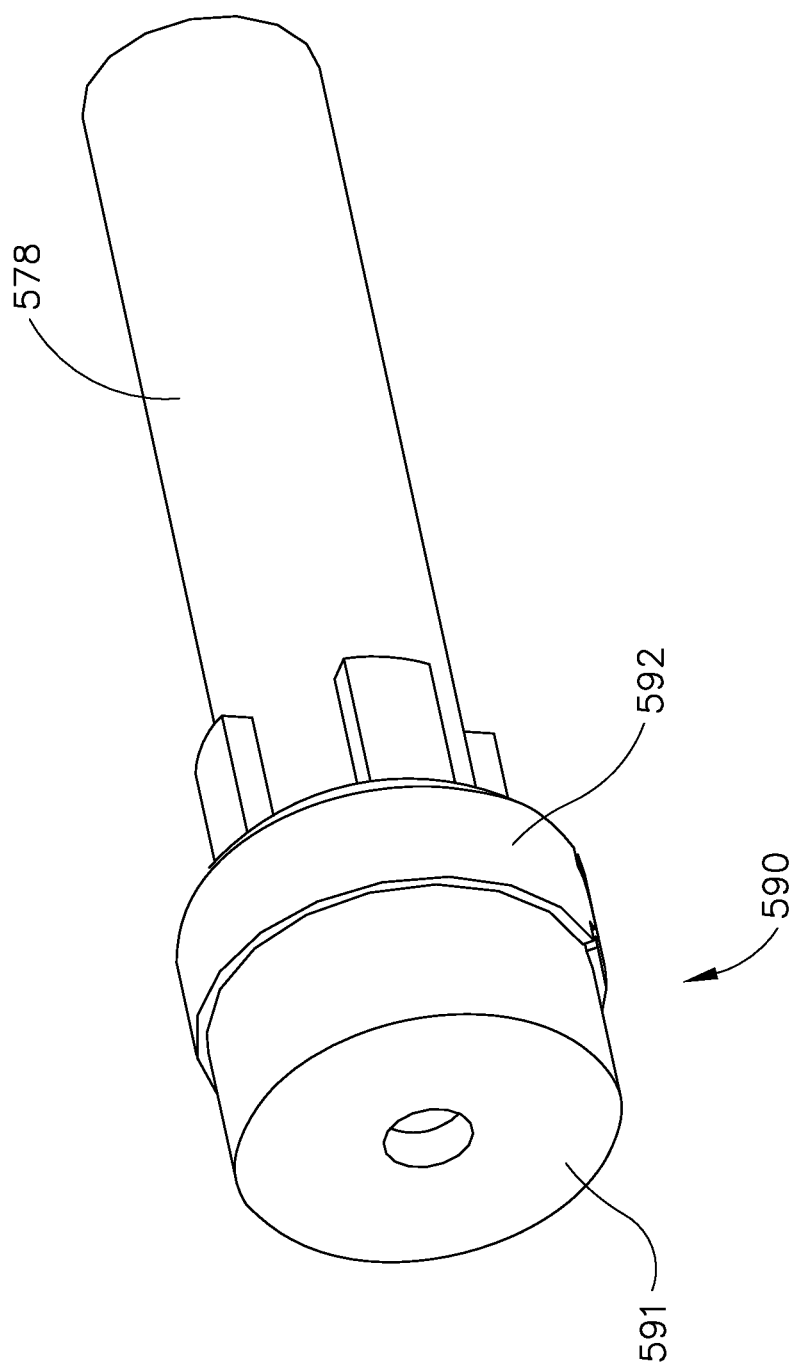
FIG. 35 depicts a perspective view of a clip ring of the assembly of FIG. 28.
Figure 36:
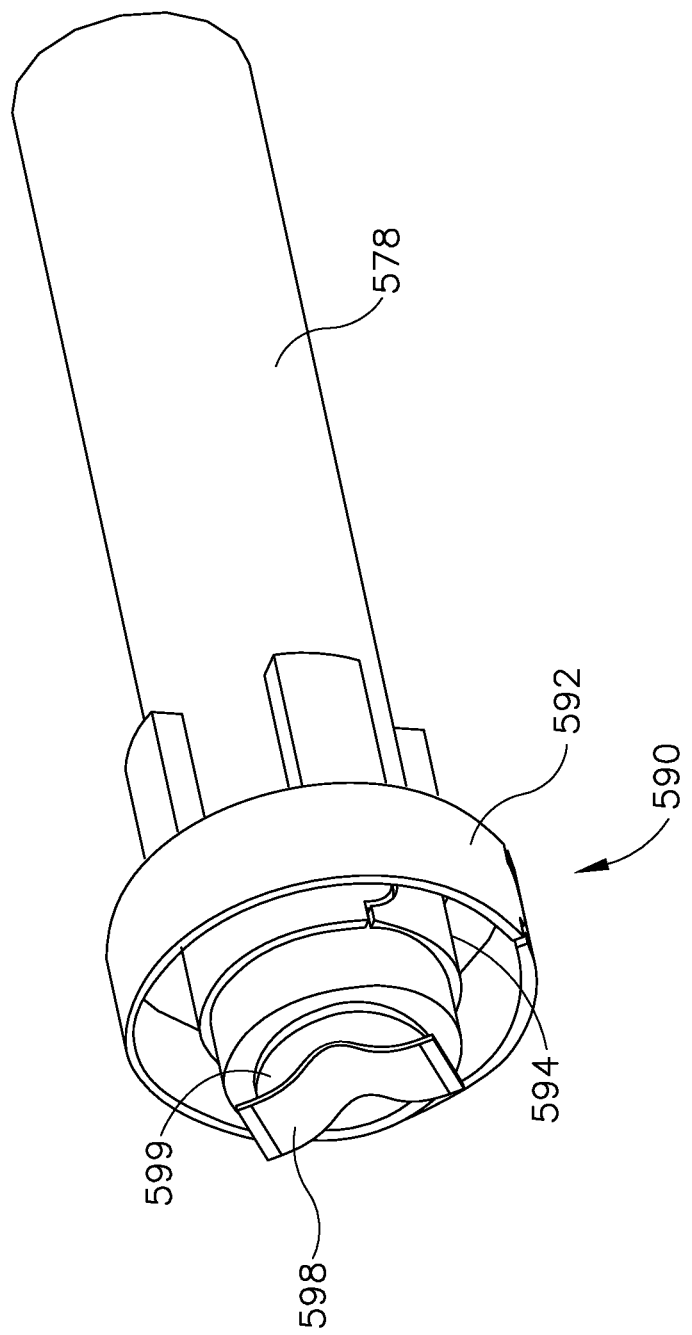
FIG. 36 depicts a perspective view of the clip ring of FIG. 35, with a cap of the clip ring omitted.
Figure 37:
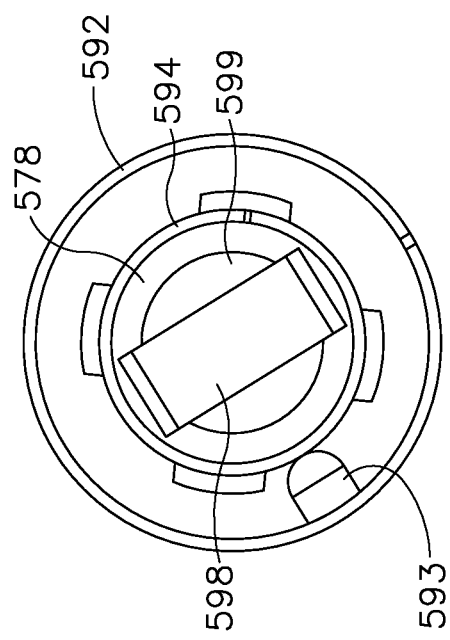
FIG. 37 depicts an end view of the clip ring of FIG. 35, with the cap omitted.

As best seen in FIGS. 35-37, a slip ring assembly (590) is positioned at the proximal end of stem (578) to provide electrical continuity between fixed wires and the wires passing through the interior of stem (578) to power transducer (560) while allowing stem (578) and transducer (560) to rotate relative to the fixed wires. Slip ring assembly (590) comprises a cap (591) and a first ring (592), which are electrically isolated from each other. Cap (591) provides a path for coupling a first fixed wire associated with a first electrical polarity; while ring (592) is coupled with a second fixed wire associated with a second electrical polarity. Cap (591) is engaged with a conductive leaf spring (598), which resiliently bears against a conductive plate (599) located at the proximal end of stem (578). Plate (599) is coupled with one or more wires in stem (578) associated with the first electrical polarity. It should be understood that leaf spring (598) and plate (599) together provide a path for electrical continuity between the first fixed wire and the one or more wires in stem (578) that are associated with the first electrical polarity; and that leaf spring (598) and plate (599) together maintain this electrical continuity while stem (578) rotates relative to the first fixed wire.

A conductive projection (593) projects inwardly from ring (592) into engagement with another ring (594). Ring (594) is fixedly secured to the exterior of stem (578) and is electrically coupled with one or more wires in stem (578) that are associated with the second electrical polarity. Ring (592) resiliently biases projection (593) into engagement with ring (594), such that projection (593) slides against ring (594) while maintaining contact with ring (594). It should be understood that rings (592, 594) and projection (593) together provide a path for electrical continuity between the second fixed wire and the one or more wires in stem (578) that are associated with the second electrical polarity; and that rings (592, 594) and projection (593) together maintain this electrical continuity while stem (578) rotates relative to the second fixed wire.

In view of the foregoing, it should be understood that motor (550) may be activated to rotate transducer (560) relative to the body of a handle assembly or other kind of body. Motor (550) may thus be activated to rotatably drive a threaded stud extending distally from horn (562) into a threaded recess of a waveguide. Motor (550) may also be activated in reverse to decouple the waveguide from horn (562). Various suitable ways in which assembly (500) may be integrated into instrument (10) and variations thereof will be apparent to those of ordinary skill in the art in view of the teachings herein.

III. Exemplary Alternative Features for Simultaneous Coupling of Acoustic Components and Clamp Arm Drive Components As noted above, it may be desirable to provide modularity whereby shaft assemblies (30) may be readily coupled with and decoupled from transducer assembly (12) and handle assembly (20) with relative ease. In some instances, such coupling and decoupling of shaft assembly (30) may include coupling waveguide (102) with transducer assembly (12) and coupling inner tube (34) with coupling assembly (35) of yoke (25). It may be desirable to provide such coupling of waveguide (102) and such coupling of inner tube (34) simultaneously. In particular, it may be desirable to provide coupling of waveguide (102) and coupling of inner tube (34) simultaneously through set of coaxially arranged and radially spaced apart threaded features. Such features may provide simultaneous coupling of waveguide (102) and coupling of inner tube (34) in a single rotational motion. FIGS. 38-49C show examples of various features that may provide such simultaneous coupling of waveguide (102) and coupling of inner tube (34) in a single rotational motion.

Figure 38:
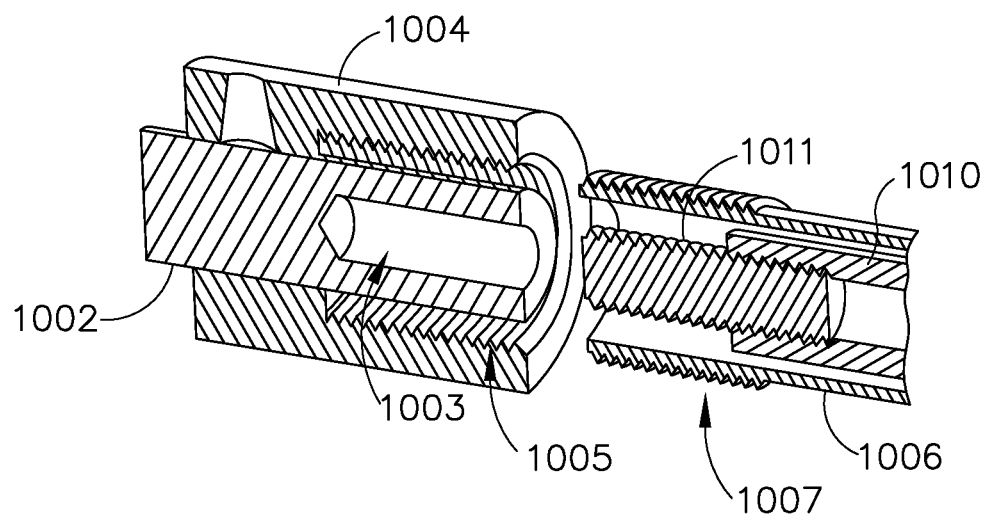
FIG. 38 depicts a perspective view of an exemplary coupling mechanism.

FIG. 38 shows an exemplary waveguide (1002) coaxially disposed within an inner tube (1004). FIG. 38 also shows an exemplary horn (1010) coaxially disposed within a tube driver (1006). It should be understood that waveguide (1002) may be used in place of waveguide (102), inner tube (1004) may be used in place of inner tube (34), horn (1010) may be a feature of transducer assembly (12), and tube driver (1006) may be a feature of coupling assembly (35) of yoke (25). In this example, the proximal end of waveguide (1002) includes a threaded bore (1003). The proximal end of tube (1004) also includes a threaded bore (1005). A stud (1011) with external threading extends distally from horn (1010). Threaded bore (1003) is configured to receive stud (1011) through a threaded engagement. Tube driver (1006) includes external threading (1007). Threaded bore (1005) is configured to receive external threading (1007) through a threaded engagement. It should therefore be understood that waveguide (1002) may be coupled with horn (1010) simultaneously as inner tube (1004) is coupled with tube driver (1006) through a single rotational motion. Once waveguide (1002) is coupled with horn (1010), ultrasonic vibrations generated by transducer assembly (12) may be communicated to waveguide (1002) via horn (1010). Once inner tube (1004) is coupled with tube driver (1006), pivotal movement of trigger (28) may provide longitudinal translation of inner tube (1004) via tube driver (1006).

Figure 39:
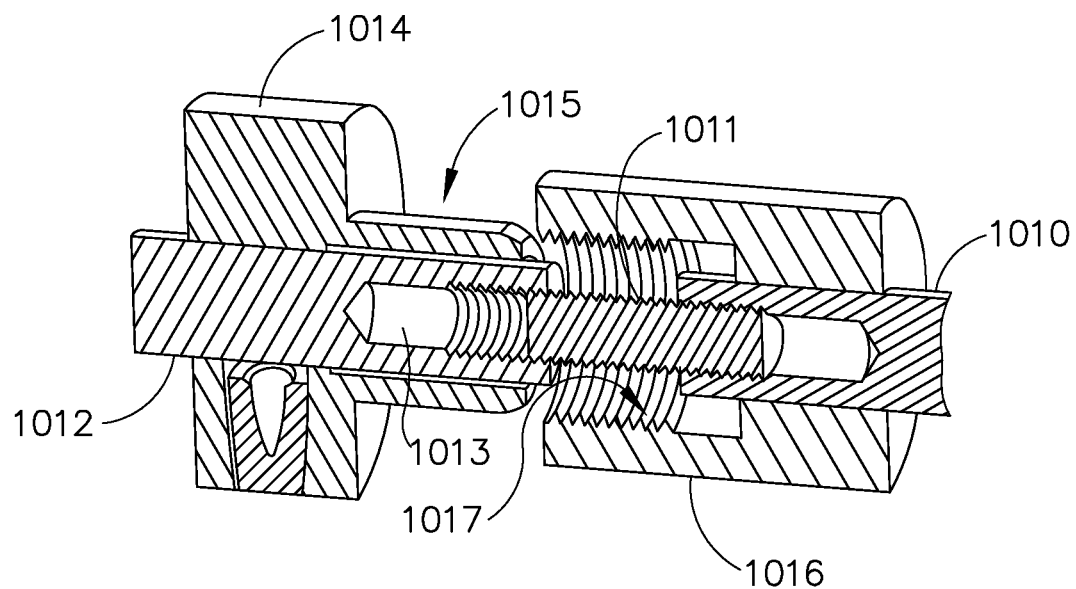
FIG. 39 depicts a perspective view of another exemplary coupling mechanism.

FIG. 39 shows an exemplary waveguide (1012) coaxially disposed within an inner tube (1014). FIG. 39 also shows an exemplary horn (1010) coaxially disposed within a tube driver (1016). It should be understood that waveguide (1012) may be used in place of waveguide (102), inner tube (1014) may be used in place of inner tube (34), horn (1010) may be a feature of transducer assembly (12), and tube driver (1016) may be a feature of coupling assembly (35) of yoke (25). In this example, the proximal end of waveguide (1012) includes a threaded bore (1013). The proximal end of tube (1014) includes a coupling sleeve (1015). A stud (1011)

with external threading extends distally from horn (1010). Threaded bore (1013) is configured to receive stud (1011) through a threaded engagement. Tube driver (1016) includes internal threading (1017). Internal threading (1017) is configured to act as a self-tapping nut over sleeve (1015), such that threading (1017) may provide threaded engagement over sleeve (1015). In some other versions, sleeve (1015) includes pre-formed external threading that complements threading (1017). It should therefore be understood that waveguide (1012) may be coupled with horn (1010) simultaneously as inner tube (1014) is coupled with tube driver (1016) through a single rotational motion. Once waveguide (1012) is coupled with horn (1010), ultrasonic vibrations generated by transducer assembly (12) may be communicated to waveguide (1012) via horn (1010). Once inner tube (1014) is coupled with tube driver (1016), pivotal movement of trigger (28) may provide longitudinal translation of inner tube (1014) via tube driver (1016).

Figure 40:
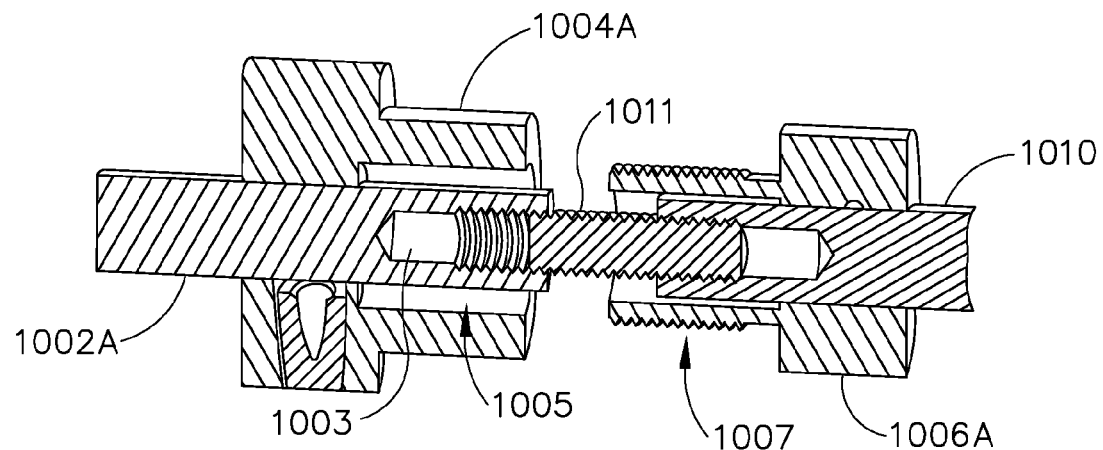
FIG. 40 depicts a perspective view of yet another exemplary coupling mechanism.

FIG. 40 shows an exemplary waveguide (1002A) coaxially disposed within an inner tube (1004A). FIG. 40 also shows an exemplary horn (1010) coaxially disposed within a tube driver (1006A). It should be understood that waveguide (1002A) may be used in place of waveguide (102), inner tube (1004A) may be used in place of inner tube (34), horn (1010) may be a feature of transducer assembly (12), and tube driver (1006A) may be a feature of coupling assembly (35) of yoke (25). In this example, the proximal end of waveguide (1002A) includes a threaded bore (1003). The proximal end of tube (1004A) includes a non-threaded bore (1005). A stud (1011) with external threading extends distally from horn (1010). Threaded bore (1003) is configured to receive stud (1011) through a threaded engagement. Tube driver (1006A) includes external threading (1007). External threading (1007) is configured to act as a self-tapping screw in bore (1005), such that threading (1007) may provide threaded engagement in bore (1005). It should therefore be understood that waveguide (1002A) may be coupled with horn (1010) simultaneously as inner tube (1004A) is coupled with tube driver (1006A) through a single rotational motion. Once waveguide (1002A) is coupled with horn (1010), ultrasonic vibrations generated by transducer assembly (12) may be communicated to waveguide (1002A) via horn (1010). Once inner tube (1004A) is coupled with tube driver (1006A), pivotal movement of trigger (28) may provide longitudinal translation of inner tube (1004A) via tube driver (1006A).

Figure 41:
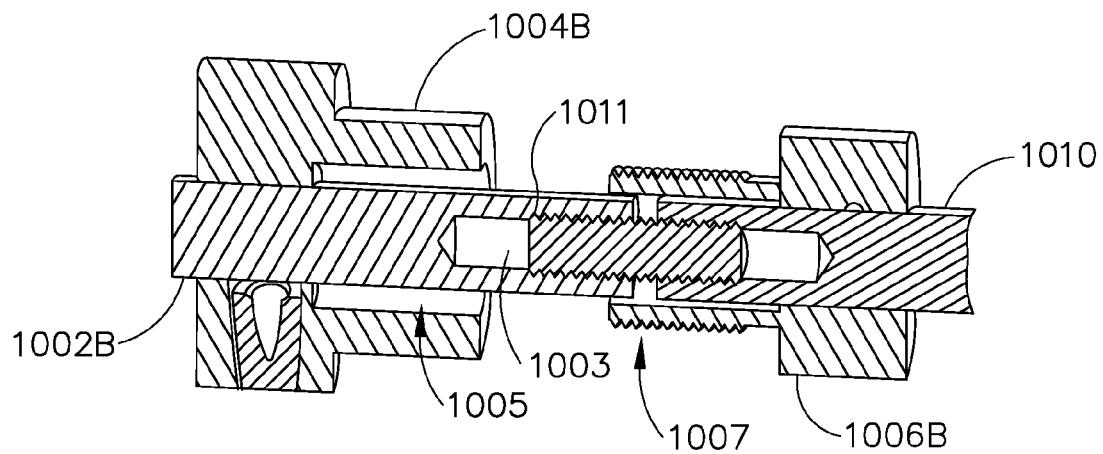
FIG. 41 depicts a perspective view of yet another exemplary coupling mechanism.

FIG. 41 shows an exemplary waveguide (1002B) coaxially disposed within an inner tube (1004B). Inner tube (1004B) of this example is substantially similar to inner tube (1004A) of the example shown in FIG. 40, except that the wall that defines bore (1005) in inner tube (1004B) is smaller than the same wall that defines bore (1005) in inner tube (1004A). FIG. 41 also shows an exemplary horn (1010) coaxially disposed within a tube driver (1006B). It should be understood that waveguide (1002B) may be used in place of waveguide (102), inner tube (1004B) may be used in place of inner tube (34), horn (1010) may be a feature of transducer assembly (12), and tube driver (1006B) may be a feature of coupling assembly (35) of yoke (25). In this example, the proximal end of waveguide (1002B) includes a threaded bore (1003). The proximal end of tube (1004B) includes a non-threaded bore (1005). A stud (1011) with external threading extends distally from horn (1010). Threaded bore (1003) is configured to receive stud (1011) through a threaded engagement. Tube driver (1006B) includes external threading (1007). External threading (1007) is configured to act as a self-tapping screw in bore (1005), such that threading (1007) may provide threaded engagement in bore (1005). It should therefore be understood that waveguide (1002B) may be coupled with horn (1010) simultaneously as inner tube (1004B) is coupled with tube driver (1006B) through a single rotational motion. Once waveguide (1002B) is coupled with horn (1010), ultrasonic vibrations generated by transducer assembly (12) may be communicated to waveguide (1002B) via horn (1010). Once inner tube (1004B) is coupled with tube driver (1006B), pivotal movement of trigger (28) may provide longitudinal translation of inner tube (1004B) via tube driver (1006B).

Figure 42:
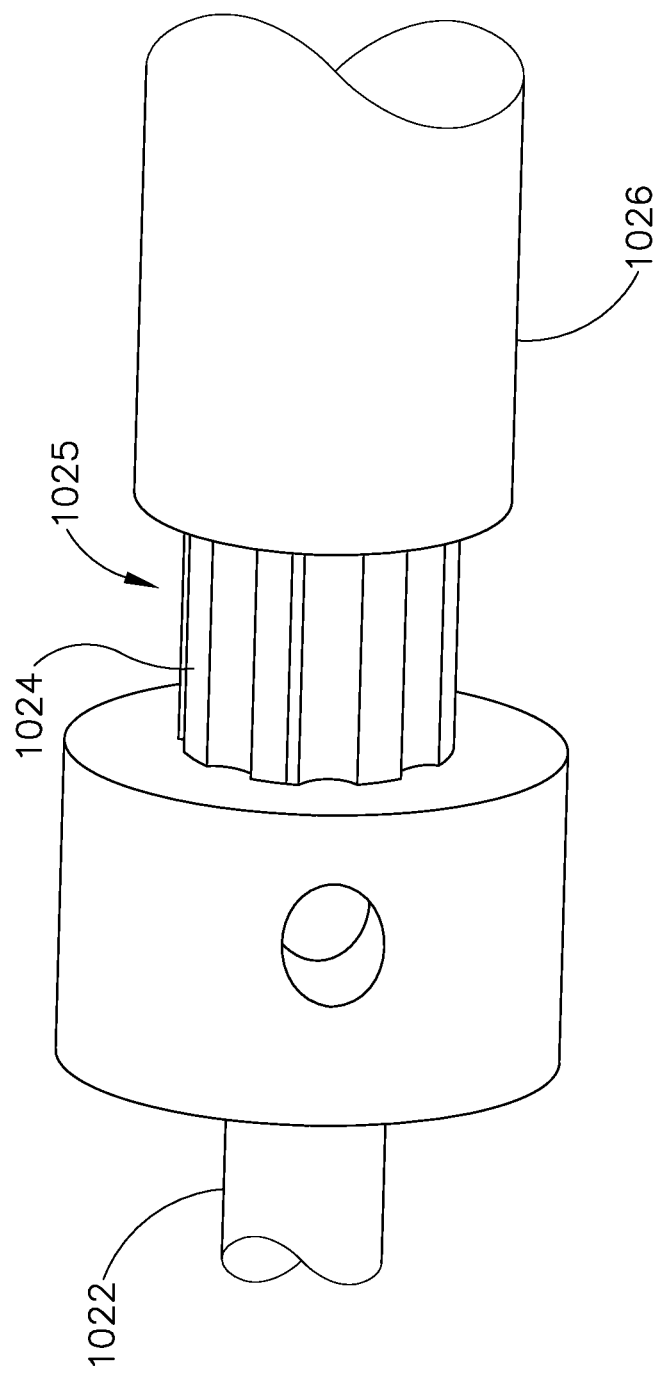
FIG. 42 depicts a perspective view of yet another exemplary coupling mechanism.
Figure 43:
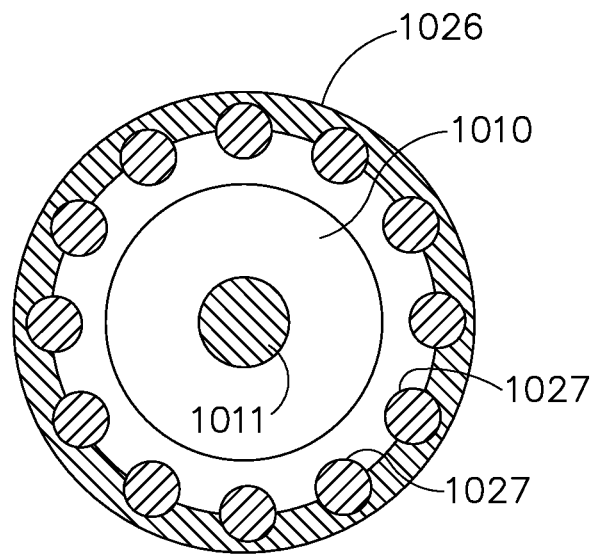
FIG. 43 depicts a cross-sectional view the coupling mechanism of FIG. 42.
Figure 44:
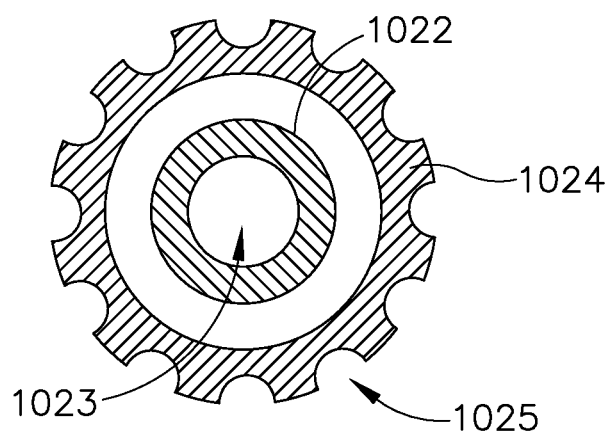
FIG. 44 depicts another cross-sectional view of the coupling mechanism of FIG. 42.

FIGS. 42-44 show a waveguide (1022) and an inner tube (1024). Waveguide (1022) comprises an internal threaded region (1023). Threaded stud (1011) of a horn (1010) is configured to be threaded into threaded region (1023) of waveguide (1022). An exterior surface of inner tube (1024) defines a plurality of longitudinal recesses (1025) disposed in an angularly spaced array about inner tube (1024). Horn (1010) extends coaxially through a keyed member (1026). Keyed member (1026) comprises a plurality of inwardly extending projections (1027) configured to fit within longitudinal recesses (1025) of inner tube (1024). It should be appreciated that either keyed member (1026) or inner tube (1024) may be made of a flexible material and that keyed member (1026) and inner tube (1024) may engage one another in such a manner to deform and cause friction between them such that longitudinal translation of keyed member (1026) is communicated to inner tube (1024). Keyed member (1026) is mechanically coupled with the triggering mechanism such that pivotal movement of trigger (28) causes longitudinal translation of inner tube (1024). As waveguide (1022) is threaded onto threaded stud (1011) of horn (1010), waveguide (1022) and inner tube (1024) will be drawn toward transducer assembly (12) and keyed member (1026) such that projections (1027) of keyed member (1026) will further engage longitudinal recesses (1025) of inner tube (1024). It should also be understood that waveguide (1022) and inner tube (1024) may be simultaneously coupled with transducer assembly (12) and the internal triggering mechanism.

Figure 45:
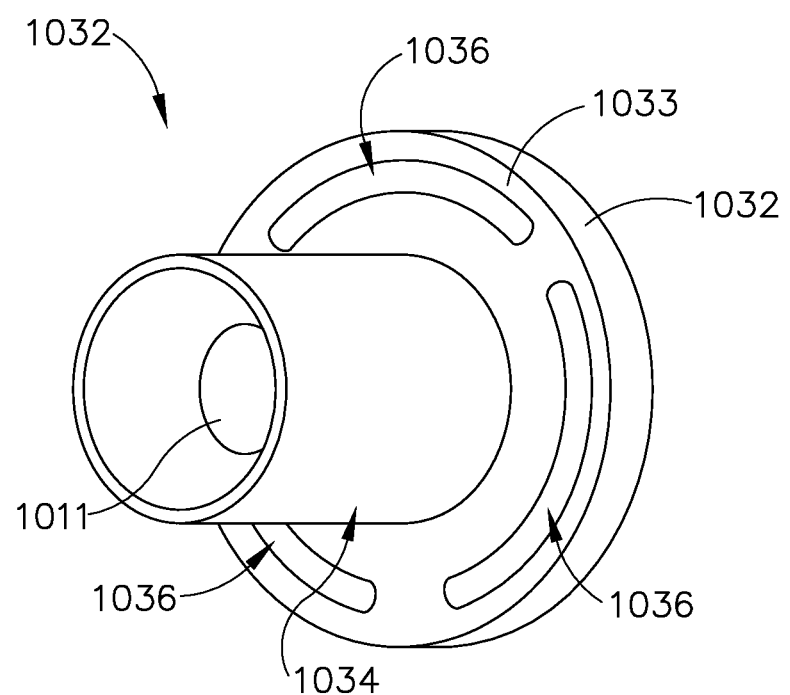
FIG. 45 depicts a perspective view of yet another exemplary coupling mechanism.
Figure 46:
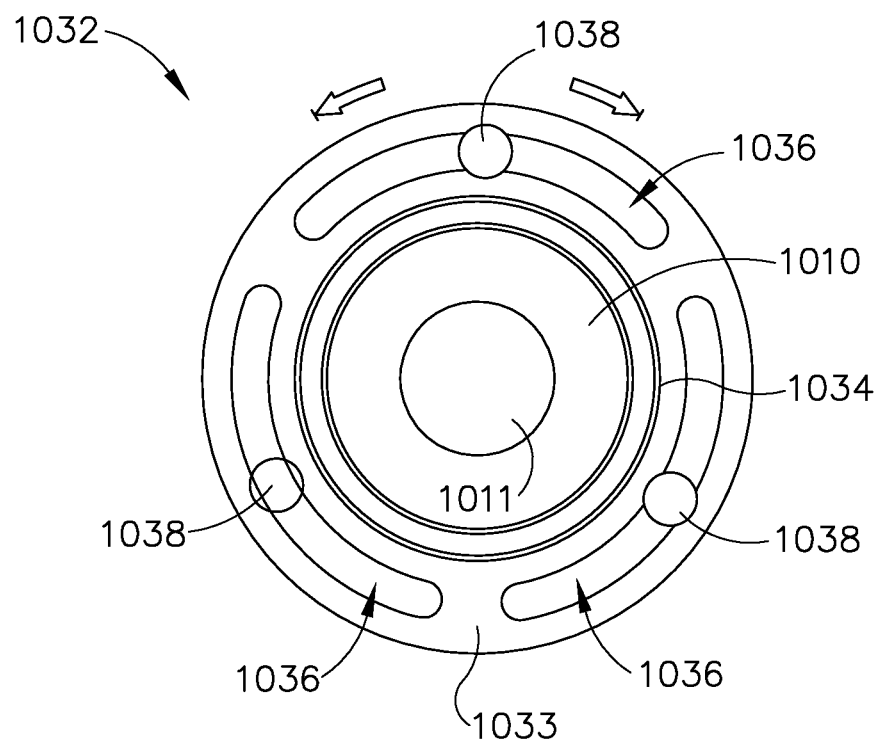
FIG. 46 depicts an end view the coupling mechanism of FIG. 45.
Figure 47:
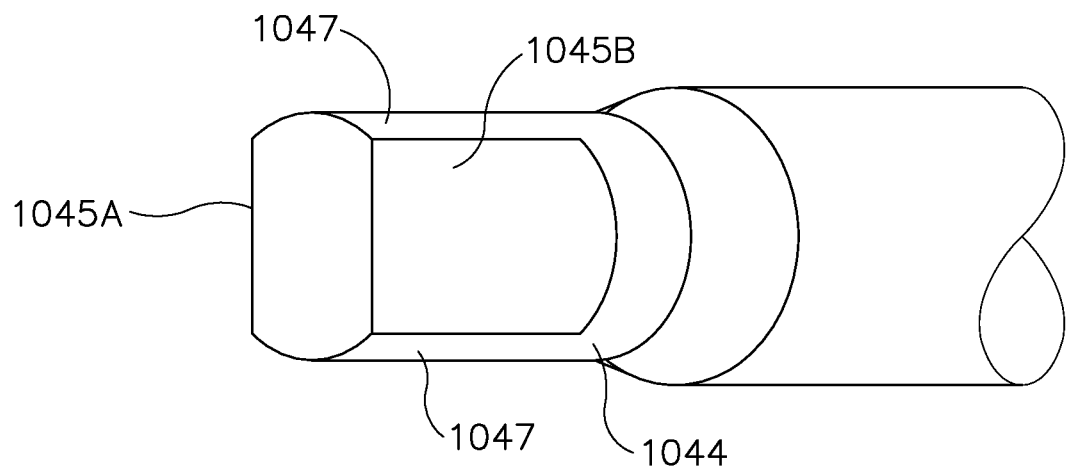
FIG. 47 depicts a perspective view of a coupling mechanism of an exemplary quarter-turn waveguide.
Figure 48:
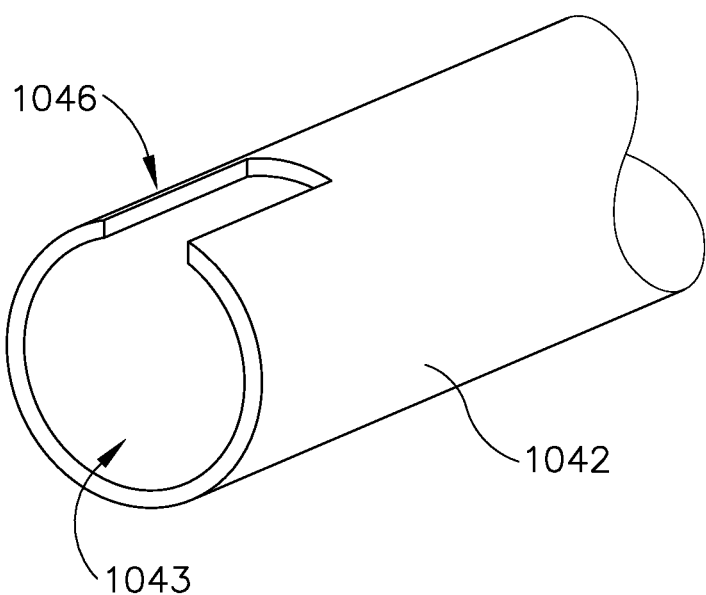
FIG. 48 depicts a perspective view of a coupling mechanism of an exemplary quarter-turn transducer.

FIGS. 45 and 46 show an adjustable member (1032) through which horn (1010) may pass. Adjustable member (1032) may comprise an internal or an external threaded region along a sleeve portion (1034) of adjustable member (1032). These threaded regions may be configured to be threadably coupled with a threaded region of inner tube (34). Adjustable member (1036) is mechanically coupled with the triggering mechanism such that pivotal movement of trigger (28) causes longitudinal translation of inner tube (34) via adjustable member (1032). Adjustable member (1032) comprises a plurality of arcuate slots (1036) formed in a flange (1033) of adjustable member (1038). Adjustable member (1032) is coupled with the triggering mechanism via a plurality of pins (1038). Pins (1038) are slidably disposed within arcuate slots (1036). As will be best appreciated from FIG. 46, adjustable member (1032) may be partially rotated by allowing pins (1038) to slide within arcuate slots (1036). Such angular adjustment may be desirable to align the threaded region of adjustable member (1032) with the threaded region of inner tube (34) and to align threaded stud (1011) of horn (1010) and the threaded bore (103) of waveguide (102).

Figure 49A:
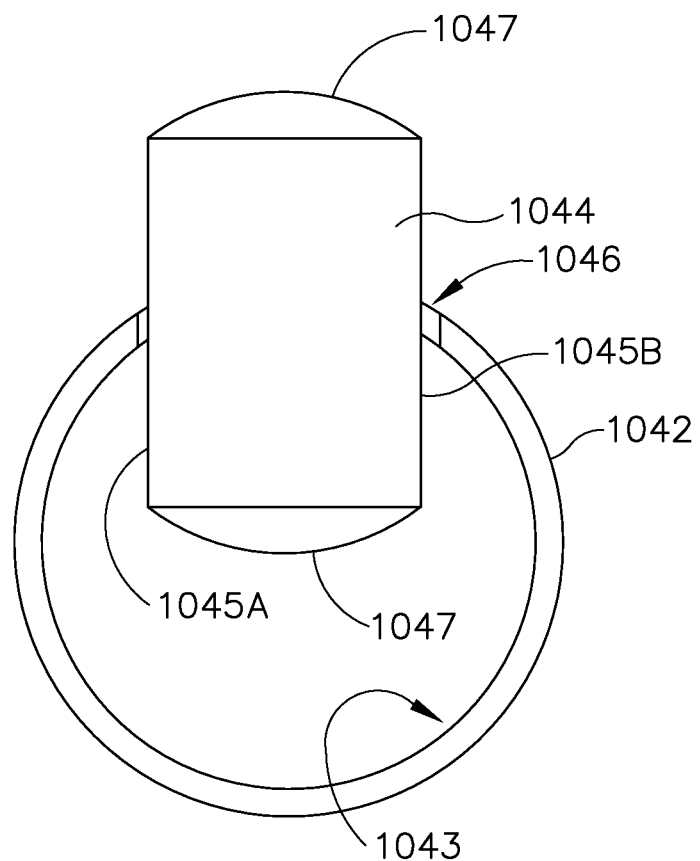
FIG. 49A depicts an elevational view of the waveguide of FIG. 47 partially disposed within the transducer of FIG. 48.
Figure 49B:
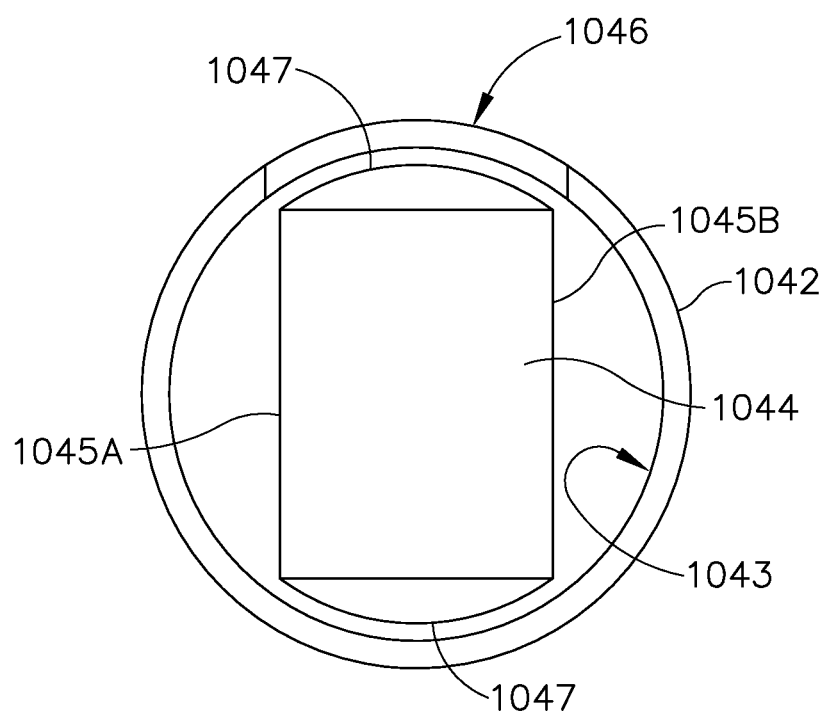
FIG. 49B depicts an elevational view of the waveguide of FIG. 47 completely disposed within the transducer of FIG. 48 and in a first rotational position.
Figure 49C:
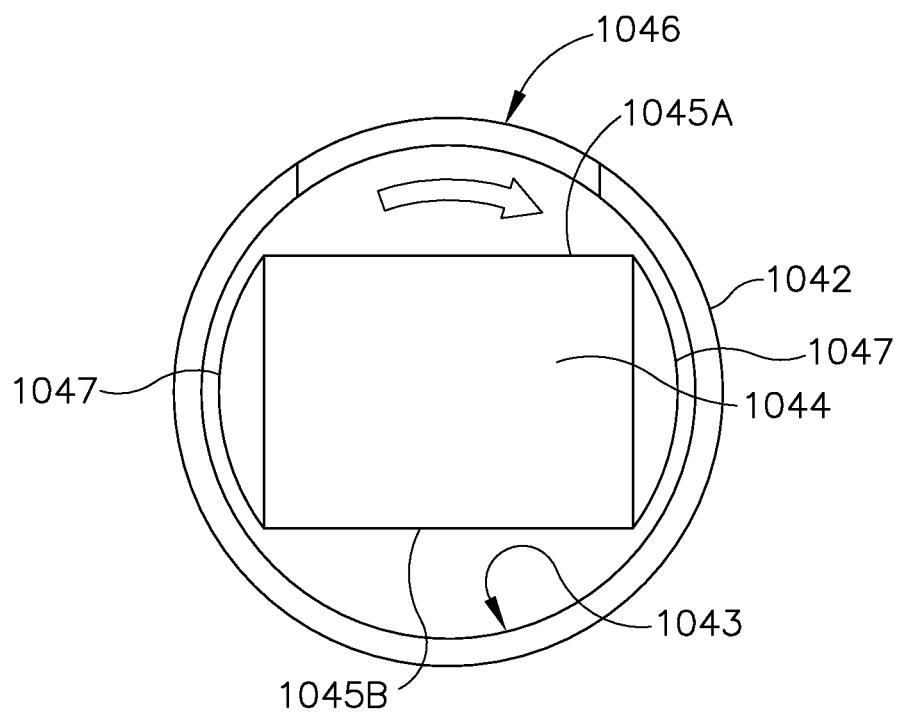
FIG. 49C depicts an elevational view of the waveguide of FIG. 47 completely disposed within the transducer of FIG. 48 and rotated into a second rotational position.

FIGS. 47-49C show an exemplary threaded stud (1044) of transducer assembly (12) and a waveguide (1042). Threaded stud (1044) and waveguide (1042) are configured to threadably engage one another by a quarter-turn of threaded stud (1044) or waveguide (1042). Threaded stud (1044) comprises a pair of flat surfaces (1045A, 1045B) and a pair of arcuate threaded regions (1047). Waveguide (1042) comprises an internal threaded region (1043) and a rectangular notch (1046) passing through a surface of waveguide (1042) and providing access to internal threaded region (1043). Notch (1046) is configured to allow threaded stud (1044) to pass through and into the internal threaded region (1043) when threaded stud (1044) is oriented as shown in FIG. 49A. In other words, notch (1046) allows waveguide (1042) to move along a transverse path relative to threaded stud (1044) in order to achieve axial alignment between waveguide (1042) and threaded stud (1044). This would enable a shaft assembly (30) incorporating waveguide (1042) to be side-loaded, top-loaded, or otherwise loaded relative to handle assembly (20) along a path that is transverse to the longitudinal axis of threaded stud (1044). Once threaded stud (1044) is completely passed through recess (1046) and into axial alignment with waveguide (1042), as shown in FIG. 49B, threaded stud (1044) or waveguide (1042) may be rotated a quarter-turn to thereby threadably couple threaded stud (1044) and waveguide (1042) as shown in FIG. 49C. In particular, threaded regions (1047) of stud (1044) engage threaded region (1043) of waveguide (1042).

IV. Exemplary Alternative Ultrasonic Surgical Instrument with Modified Trigger

Figure 50:
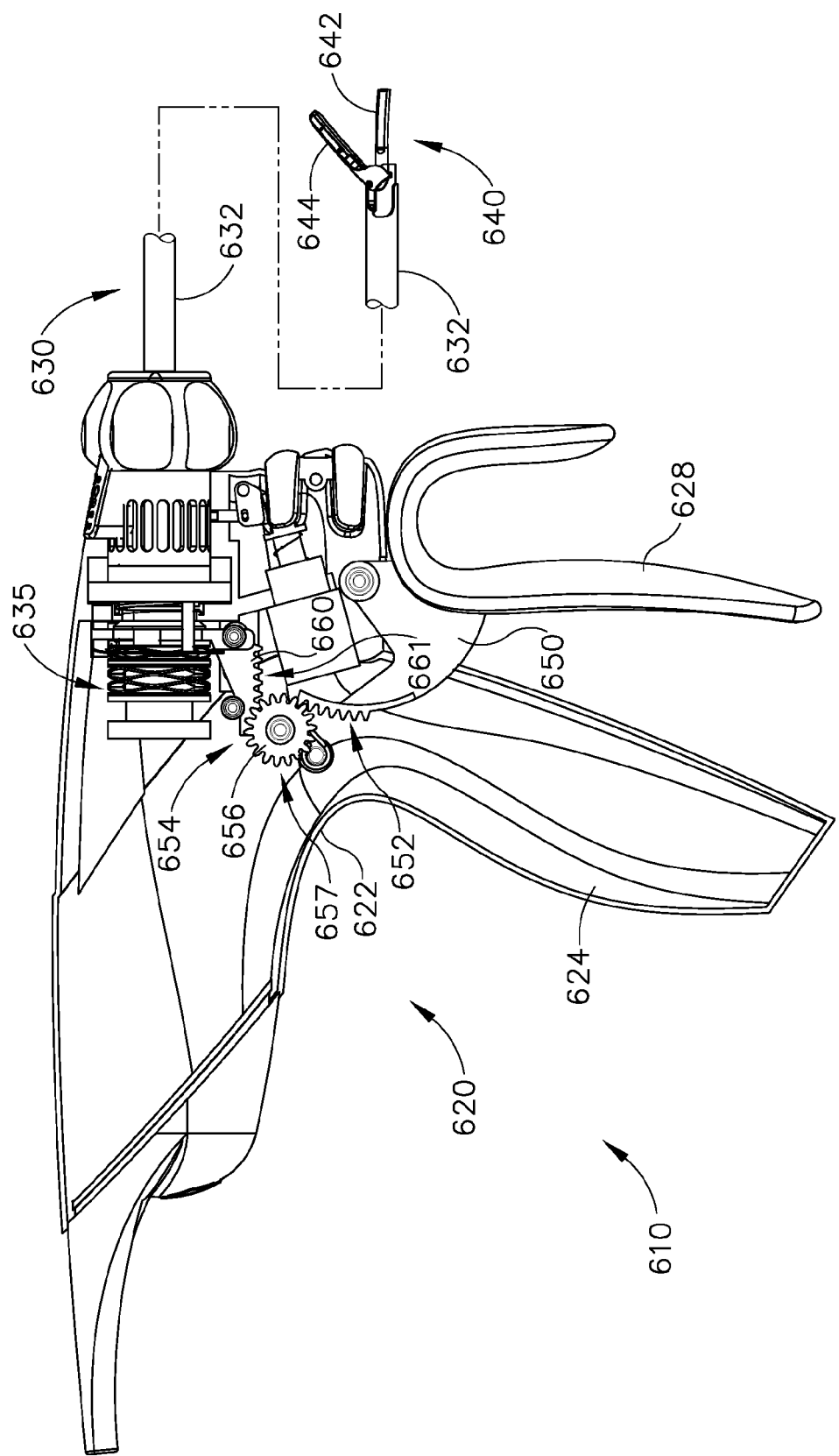
FIG. 50 depicts a side elevational view of yet another exemplary alternative surgical instrument.
Figure 51:
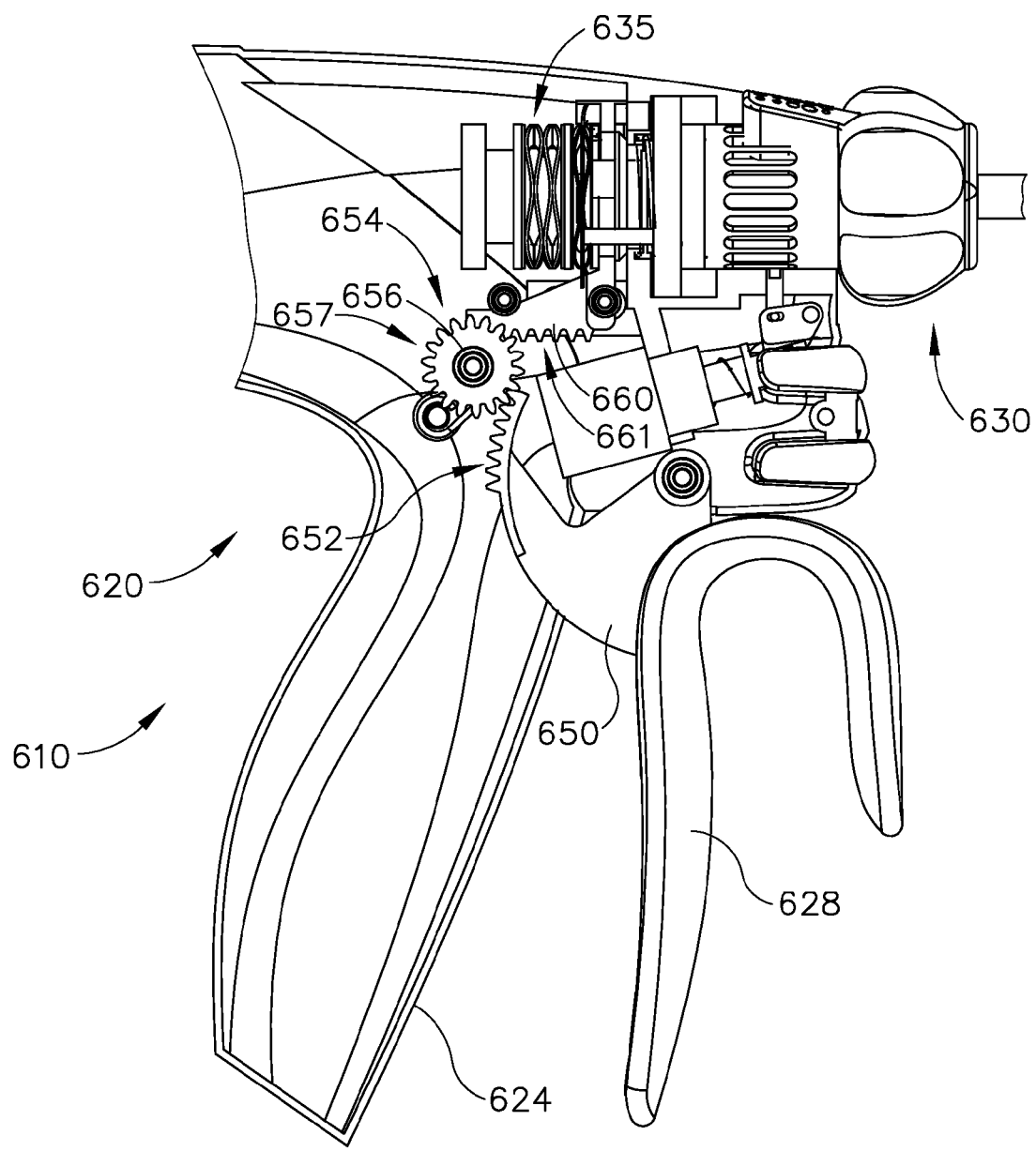
FIG. 51 depicts a side elevational view of a triggering mechanism of the instrument of FIG. 50.
Figure 52:
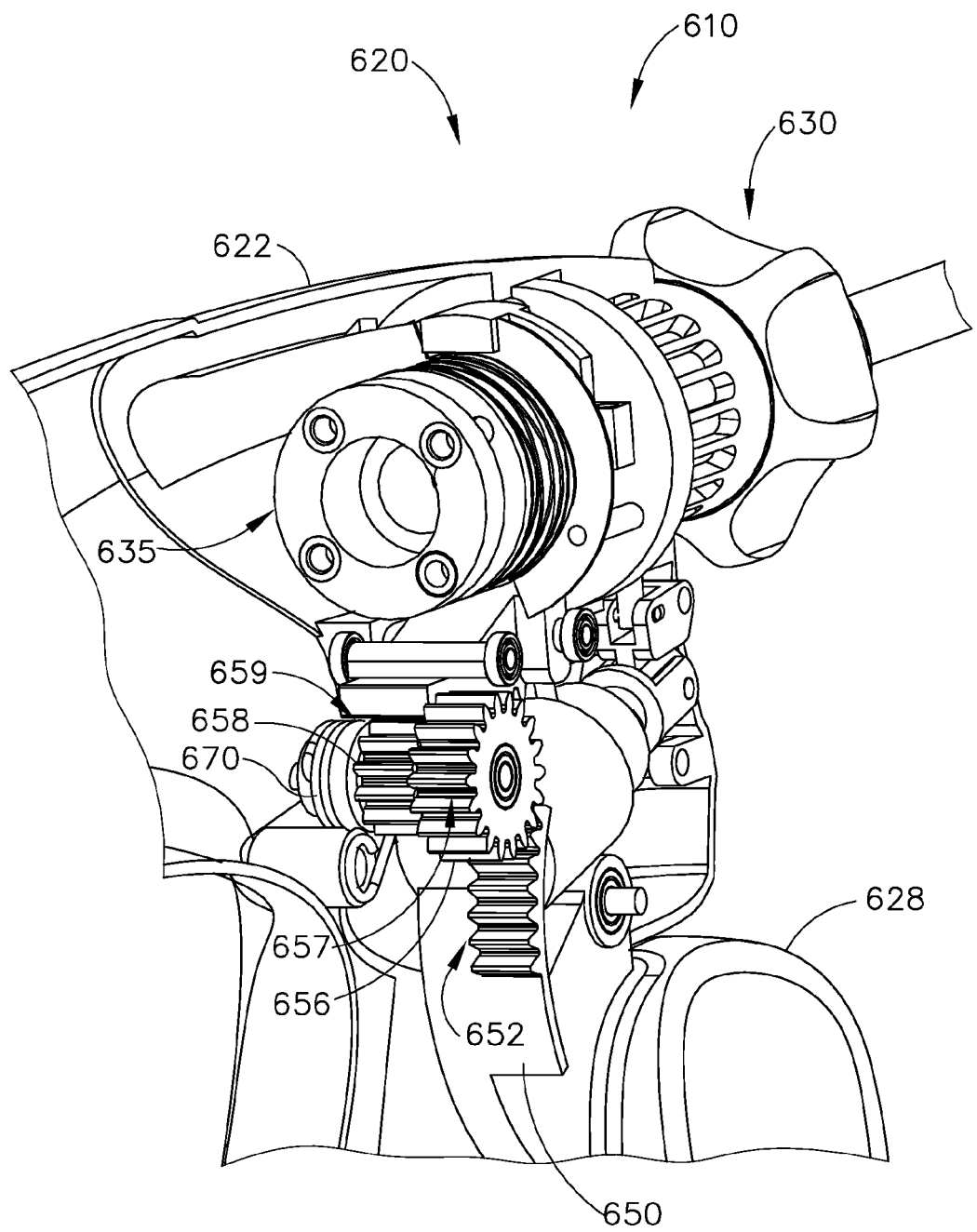
FIG. 52 depicts a perspective view of the triggering mechanism of FIG. 51.

FIG. 50-52 show an exemplary alternative surgical instrument (610). Instrument (610) of the present example is configured to operate substantially similar to instrument (10) discussed above except for the differences discussed below. Instrument (610) of the present example comprises a handle assembly (620), a shaft assembly (630), and an end effector (640). Shaft assembly (630) comprises an outer sheath (632), an inner tube (not shown) slidably disposed within outer sheath (632), and a waveguide (602) disposed within the inner tube. As with inner tube (34) of instrument (10) discussed above, longitudinal translation of the inner tube of the present example causes actuation of a clamp arm (644) of end effector (640) toward and away from an ultrasonic blade (642). Handle assembly (620) comprises a body (622) including a pistol grip (624). Handle assembly (620) also includes a trigger (628) that is pivotable toward and away from pistol grip (624). Trigger (628) is pivotably coupled to handle assembly (620). As will be discussed in more detail below, pivotal movement of trigger (628) causes longitudinal translation of inner tube (634) to thereby cause pivotal movement of clamp arm (644) toward and away from ultrasonic blade (642).

Trigger (628) is coupled with an arcuate rack member (650), which is disposed within handle assembly (620). Arcuate rack member (650) comprises a plurality of teeth (652). A rotatable member (654) having a first gear (656) and a second gear (658) is also disposed within handle assembly (620). First gear (656) comprises a plurality of external teeth (657). Second gear (658) also comprises a plurality of external teeth (659). First gear (656) and second gear (658) have different diameters, with first gear (656) having a larger diameter than second gear (658). Teeth (657) of first gear (656) of rotatable member (654) are configured to mesh with teeth (652) of arcuate rack member (650) of trigger (628) such that pivotal movement of trigger (628) toward and away from pistol grip (624) causes rotation of first gear (656), rotatable member (654), and second gear (658).

Handle assembly (620) further comprises a rack member (660) coupled with a coupling assembly (635) such that longitudinal translation of rack member (660) causes concurrent longitudinal translation of coupling assembly (635). Coupling assembly (635) is configured to couple with the inner tube such that longitudinal translation of coupling assembly (635) causes concurrent longitudinal translation of the inner tube. Rack member (660) comprises a plurality of rollers (662) that rest upon a pair of ledges formed in an interior surface of body (622) of handle assembly (620) and permit longitudinal translation of rack member (660) between an proximal longitudinal position and a distal longitudinal position. Rack member (660) comprises a plurality of teeth (661) extending downwardly from an exterior surface of rack member (660). Teeth (661) of rack member (660) are configured to engage teeth (659) of second gear (658) of rotatable member (654) such that rotation of rotatable member (654) causes longitudinal translation of rack member (660) via second gear (658). Thus, it should be understood that pivotal movement of trigger (628) toward and away from pistol grip (624) causes rotation of first gear (656), rotatable member (654), and second gear (658), which in turn causes longitudinal translation of coupling assembly (635) and the inner tube to thereby cause pivotal movement of clamp arm (644) toward and away from ultrasonic blade (642). As best seen in FIG. 52, a torsion spring (670) may be used to resiliently bias trigger (628) away from pistol grip (624), thereby resiliently urging clamp arm (644) away from ultrasonic blade (642). Alternatively, a resilient bias may be provided in any other suitable fashion, if at all.

V. Exemplary Alternative Shaft Assembly and Transducer Assembly with Bayonet Mount FIGS. 53A-53D show an exemplary shaft assembly (730) and transducer assembly (760) that may be readily incorporated into instrument (10). Transducer assembly (760) comprises an ultrasonic transducer (762) and a resilient shroud assembly (764). Ultrasonic transducer (762) of the present example is configured to operate substantially similar to ultrasonic transducer (12) discussed above except for the differences discussed below. For instance, transducer assembly (762) converts electrical power into ultrasonic vibrations through piezoelectric principles and communicates these vibrations along an acoustic waveguide (702), which extends through shaft assembly (730) to reach an ultrasonic blade (not shown). Shaft assembly (730) comprises an outer sheath (732), an inner tube (734) slidably disposed within outer sheath (732), and a waveguide (702) disposed within inner tube (734). As with inner tube (34) of instrument (10) discussed above, longitudinal translation of inner tube (734) of the present example causes actuation of a clamp arm (not shown) of an end effector (not shown) toward and away from the ultrasonic blade.

Resilient shroud assembly (764) of the present example comprises a first member (766) and a second member (768). Second member (768) is slidably disposed within first member (766) and is resiliently biased distally by a resilient member (not shown) that is disposed within first member (766) and bears distally against second member (768). Second member (768) may translate relative to first member (766) between a distal position and a proximal position. In some versions, second member (768) protrudes distally from a handle assembly (or other kind of body of a surgical instrument in which transducer assembly (760) is incorporated) when second member (768) is in the distal position.

First member (766) comprises a distal portion (766A), a proximal portion (766B), and an intermediate portion (766C). Intermediate portion (766C) is conical in shape, whereas distal portion (766A) and proximal portion (766B) are cylindraceous. Proximal portion (766B) is configured to fit about a distal portion of ultrasonic transducer (762) such that first member (766) may be coupled thereto. First member (766) and second member (768) each define an interior bore and thus provide access to a threaded stud (not shown) of ultrasonic transducer (762). Distal portion (766A) of first member (766) defines an L-shaped slot (767). Second member (768) defines a longitudinal slot (769). Second member (768) is oriented such that slot (769) of second member (768) is substantially aligned with a longitudinally extending portion of L-shaped slot (767). A proximal portion of shaft assembly (730) comprises an outwardly extending pin (731) configured to fit within slot (769) of second member (768) and L-shaped slot (767) of first member (766).

Figure 53A:
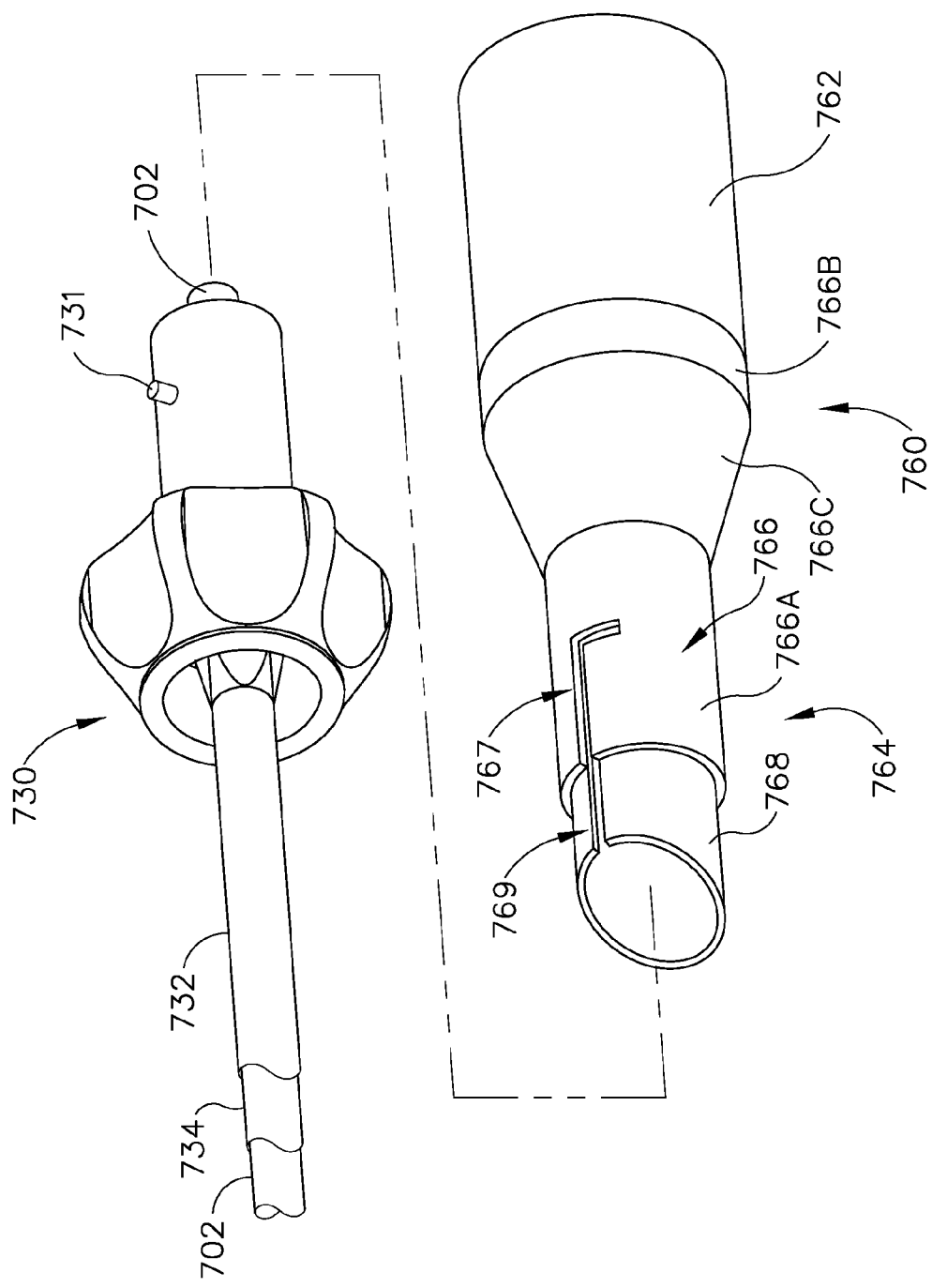
FIG. 53A depicts a perspective view of an exemplary shaft assembly and ultrasonic transducer suitable for incorporation into the instrument of FIG. 1.
Figure 53B:
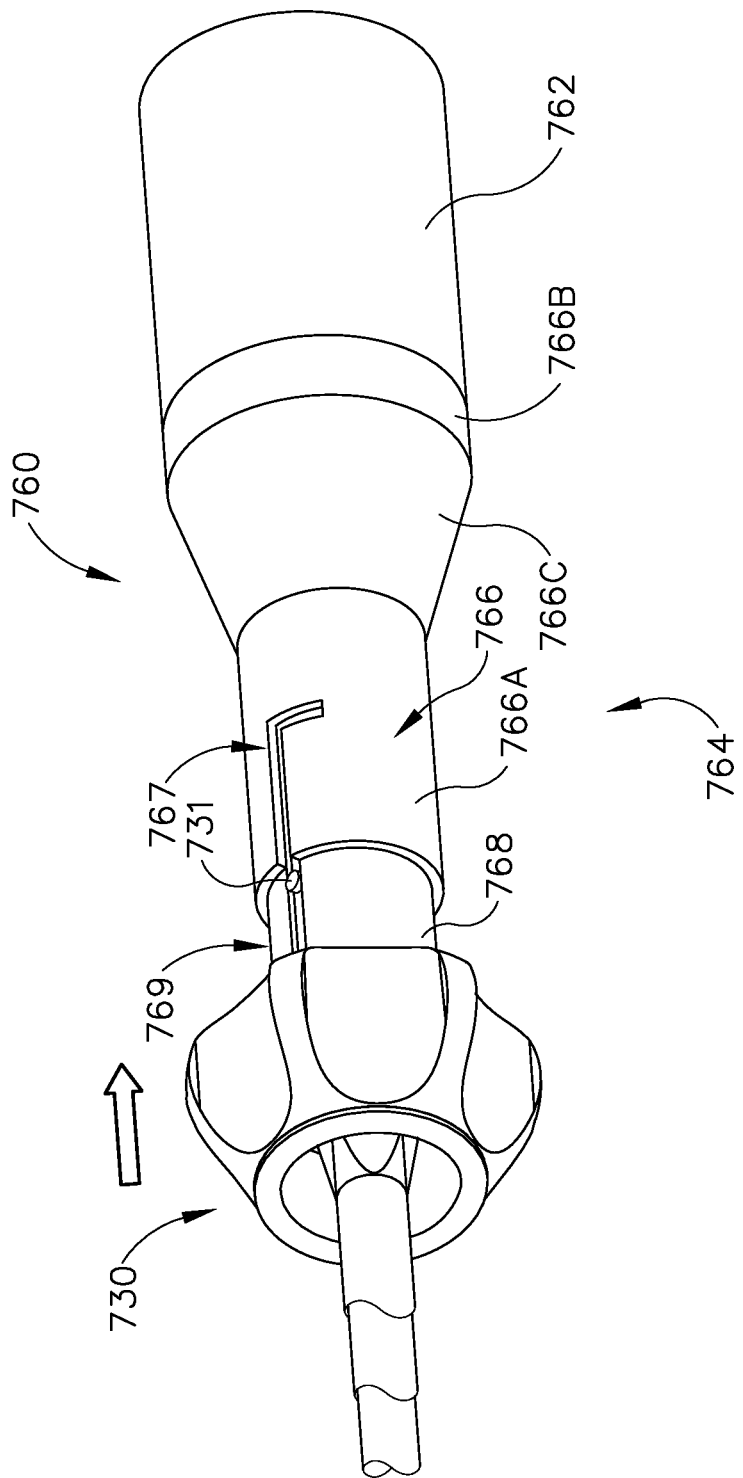
FIG. 53B depicts a perspective view of the shaft assembly and ultrasonic transducer of FIG. 53A with the shaft assembly positioned within the ultrasonic transducer.
Figure 53C:
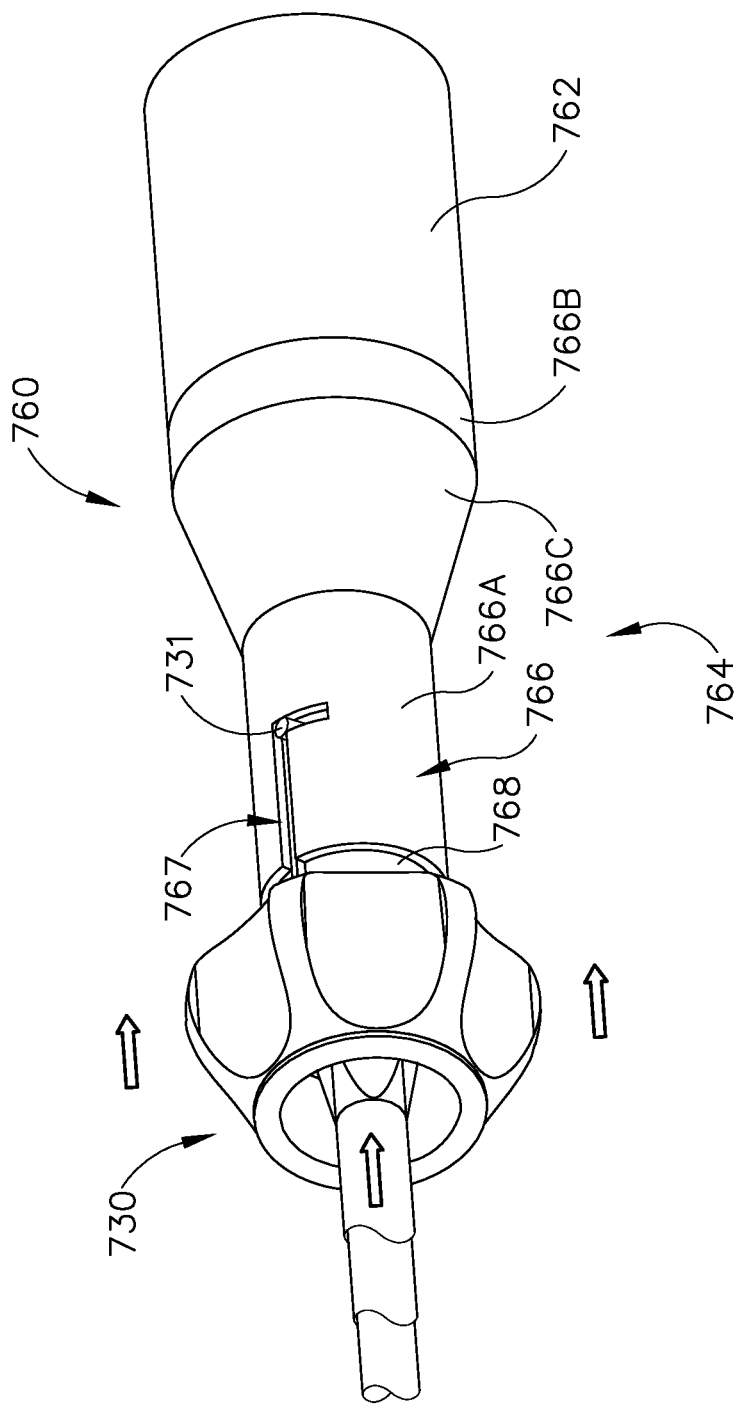
FIG. 53C depicts a perspective view of the shaft assembly and ultrasonic transducer of FIG. 53A with the shaft assembly positioned further within the ultrasonic transducer.
Figure 53D:
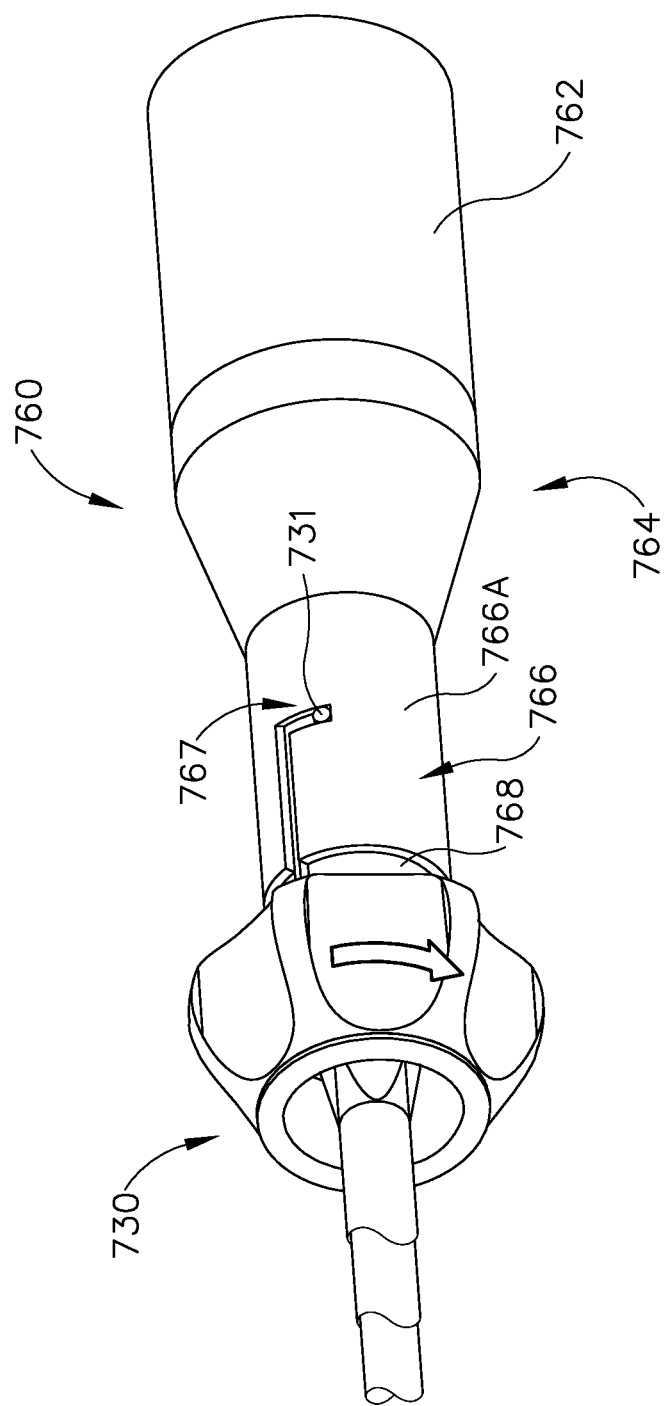
FIG. 53D depicts a perspective view of the shaft assembly and ultrasonic transducer of FIG. 53A with the shaft assembly threaded onto the ultrasonic transducer.

FIGS. 53A-53D show the steps of coupling shaft assembly (730) with ultrasonic transducer (762) of transducer assembly (760). Shaft assembly (730) is moved from a distal position, as shown in FIG. 53A, to a position where shaft assembly (730) is disposed within second member (766), as shown in FIG. 53B. In this position, pin (731) is disposed within slot (769) of second member (768). Shaft assembly (730) is then moved proximally by overcoming the distal bias of second member (768). As shaft assembly (730) and second member (768) are moved proximally, pin (731) moves longitudinally within slot (769) and the longitudinally extending portion of L-shaped slot (767) until pin (731) contacts a proximal surface of L-shaped slot (767) of first member (766) and can therefore be moved proximally no further, as shown in FIG. 53C. It should be understood that shaft assembly (730) drives second member (768) proximally further into first member (766) during the transition from the configuration shown in FIG. 53B to the configuration shown in FIG. 53C. At this point, shaft assembly (730) may be rotated within L-shaped slot (767) to thereby lock shaft assembly (730) and second member (768) in the proximal position, as shown in FIG. 53D. Thus, it should be understood that shaft assembly (730) is secured within transducer assembly (760) in a bayonet-like manner. In the present example, rotating shaft assembly (730) from the position shown FIG. 53C to the position shown in FIG. 53D, while transducer (762) remains stationary, is sufficient to mechanically and acoustically couple waveguide (702) with transducer (762). It should also be understood that the configuration of shroud assembly (764) and pin (731) may assist in ensuring proper axial and angular alignment between waveguide (702) and transducer (762) upon reaching the stage shown in FIG. 53C.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:

(a) a body;
(b) a translatable housing slidably housed within the body;
(c) an ultrasonic transducer;
(e) a shaft assembly configured to selectively couple with the translatable housing, wherein the shaft assembly defines a longitudinal axis; and
(f) a coupling assembly, wherein the coupling assembly comprises:
  (i) a motor, wherein the motor is operable to drive the translatable housing toward the ultrasonic transducer and rotate the ultrasonic transducer relative to the body to thereby couple the shaft assembly with the ultrasonic transducer, and
  (ii) a locking feature, wherein the locking feature is configured to selectively engage the shaft assembly to thereby prevent rotation of the shaft assembly relative to the body as the ultrasonic transducer is rotated to couple with the shaft assembly.

2. The apparatus of claim 1, wherein the locking feature comprises at least one longitudinal slot, wherein the shaft assembly comprises at least one longitudinal projection configured to be disposed within the at least one longitudinal slot.

3. The apparatus of claim 1, wherein the motor is further operable to cause longitudinal translation of the shaft assembly.

4. The apparatus of claim 1, wherein the body further comprises a trigger and a rotatable locking member, wherein the trigger is pivotable toward and away from the body to thereby cause the rotatable locking member to selectively engage and disengage the shaft assembly.

5. The apparatus of claim 1, wherein the shaft assembly comprises a plurality of longitudinal splines.

6. The apparatus of claim 5, wherein the coupling assembly comprises a longitudinally translatable locking member, wherein the longitudinally translatable locking member is configured to engage at least one spline of the plurality of splines to thereby prevent rotation of the shaft assembly.

7. The apparatus of claim 6, wherein the coupling assembly comprises a lever arm configured to pivot through a first range of motion and a second range of motion.

8. The apparatus of claim 7, wherein the motor is configured to activate to rotate the ultrasonic transducer during the first range of motion of the lever arm, wherein the motor is configured to deactivate during the second range of motion of the lever arm.

9. The apparatus of claim 7, wherein the lever arm is operable to translate the locking member after completing the first range of motion.

10. The apparatus of claim 9, wherein the lever arm is coupled with the locking member via a cable.

11. The apparatus of claim 1, wherein the coupling assembly further comprises:
  (i) a housing disposed about the transducer, and
  (ii) a ring gear disposed about the housing, wherein the motor is operable to rotate the ring gear, wherein the ring gear is operable to rotate the housing to thereby rotate the transducer, wherein the housing is configured to translate longitudinally within the ring gear.

12. The apparatus of claim 1, wherein the motor is coaxially disposed about the transducer.

13. The apparatus of claim 12, wherein the motor further comprises a rotor and a stator, wherein the rotor is secured to the transducer, wherein the stator is secured to the body.

14. The apparatus of claim 12, further comprising a gear assembly, wherein the motor comprises a rotor and a stator, wherein the gear assembly is operable to provide rotation of the rotor relative to the body and rotation of the stator relative to the body in response to activation of the motor.

15. The apparatus of claim 14, wherein the rotor further includes a stem passing through the gear assembly, wherein the stem includes slip ring feature configured to provide electrical continuity to the ultrasonic transducer.

16. The apparatus of claim 1, wherein the motor is operable to rotate an axle, wherein the axle includes a threaded section.

17. The apparatus of claim 1, wherein the motor is operable to rotate an axle to directly drive the translatable housing, wherein the axle includes a gear having teeth.

18. An apparatus for operating on tissue, the apparatus comprising:
  (a) a body;
  (b) an ultrasonic transducer, wherein the ultrasonic transducer comprises a threaded stud;
  (c) a translating driver, wherein the translating driver is coaxially disposed about the threaded stud, wherein the translating driver has threading; and
  (d) a shaft assembly, wherein the shaft assembly comprises:
    (i) a waveguide having a threaded bore, wherein the threaded bore is configured to threadably receive the threaded stud of the ultrasonic transducer, and
    (ii) a translating tubular member coaxially disposed about the waveguide, wherein the translating tubular member is translatable relative to the waveguide, wherein the translating tubular member has a coupling section coaxially disposed about the threaded bore of the waveguide, wherein the coupling section of the translating tubular member is configured to threadably engage the threading of the translating driver.

19. The apparatus of claim 18, further comprising a bayonet slot and pin configured to guide the waveguide into alignment with the threaded stud.

20. An apparatus for operating on tissue, the apparatus comprising:
  (a) a handle assembly, the handle assembly including a grip;
  (b) a shaft assembly, wherein a proximal end of the shaft assembly is removably coupled to the handle assembly, wherein the shaft assembly is configured to extend distally from the handle assembly when coupled to the handle assembly, wherein the shaft assembly comprises a longitudinally translatable member, wherein the shaft defines a longitudinal axis;
  (c) an end effector attached to a distal end of the shaft assembly comprising a pivotable clamp arm, wherein the translatable member is translatable relative to the handle assembly to thereby cause pivotal movement of the clamp arm;
  (d) an energizing element located proximal relative to the shaft assembly, wherein the energizing element is configured to power the end effector when the shaft assembly is coupled to the handle assembly; and
  (e) a coupling assembly configured to couple the shaft assembly with the energizing element, wherein the coupling assembly comprises:
    (i) a motor,
    (ii) a rotatable housing configured to be driven by the motor to couple the energizing element with the shaft assembly, and
    (iii) a translatable housing configured to receive the shaft assembly, wherein the translatable housing is configured to translate relative to the handle assembly in response to the motor in order to translate the shaft assembly toward the energizing element.

\* \* \* \* \*